US011040171B2

(12) United States Patent
Armour et al.

(10) Patent No.: US 11,040,171 B2
(45) Date of Patent: *Jun. 22, 2021

(54) MEDICAL DEVICE CURVING SYSTEM

(71) Applicant: Armour Technologies, Inc., Swarthmore, PA (US)

(72) Inventors: Andrew W. Armour, Swarthmore, PA (US); William Gallo, Newtown Square, PA (US); Karen L Haberland, Sewell, NJ (US); Cynthia L Waldie, Norwood, PA (US); Clayton W Waldie, Norwood, PA (US)

(73) Assignee: Armour Technologies, Inc., Swarthmore, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/880,116

(22) Filed: May 21, 2020

(65) Prior Publication Data

US 2020/0316337 A1     Oct. 8, 2020

Related U.S. Application Data

(60) Continuation of application No. 15/065,572, filed on Nov. 8, 2017, now Pat. No. 10,729,878, which is a
(Continued)

(51) Int. Cl.
  *B29C 53/08* (2006.01)
  *A61M 25/00* (2006.01)
  *B29L 31/00* (2006.01)

(52) U.S. Cl.
  CPC ........ *A61M 25/0009* (2013.01); *B29C 53/083* (2013.01); *A61M 2207/10* (2013.01); *B29L 2031/7542* (2013.01)

(58) Field of Classification Search
  CPC ......... B29C 57/00; B29C 57/04; B29C 57/10; B21D 7/00; B21D 7/08; B21D 7/12; B21D 7/14; B21D 7/162
  See application file for complete search history.

(56) References Cited

U.S. PATENT DOCUMENTS 3,719,737 A     3/1973 Vaillancourt et al.
3,839,841 A     10/1974 Amplatz
(Continued)

FOREIGN PATENT DOCUMENTS

EP     0417865 A1     3/1991
EP     0600676 A2     6/1994
(Continued)

OTHER PUBLICATIONS

International Preliminary Report on Patentability for International Application No. PCT/US2014/0278621, dated Sep. 15, 2015—10 Pages.
(Continued)

*Primary Examiner* — Joseph S Del Sole
*Assistant Examiner* — Thu Khanh T Nguyen
(74) *Attorney, Agent, or Firm* — RatnerPrestia

(57) ABSTRACT

System for curving an elongated medical device including a curving apparatus, and a curve database corresponding to at least one curve shape. The curving apparatus is configured to impart a permanent curve according to the curve shape on a distal portion of an elongated medical device that is greater than that on a proximal portion of the elongated medical device while maintaining sterility of the elongated medical device.

40 Claims, 45 Drawing Sheets

Related U.S. Application Data division of application No. 14/777,146, filed as application No. PCT/US2014/027864 on Mar. 14, 2014, now Pat. No. 9,901,705.

(60) Provisional application No. 61/790,900, filed on Mar. 15, 2013.

(56) References Cited

U.S. PATENT DOCUMENTS

| | | | |
|---|---|---|---|
| 3,866,458 A | 2/1975 | Wagner | |
| 4,292,270 A | 9/1981 | Hannahh et al. | |
| 4,368,023 A | 1/1983 | Hannah et al. | |
| 4,863,365 A | 9/1989 | Ledoux et al. | |
| 5,502,997 A | 4/1996 | Boettger et al. | |
| 5,593,708 A | 1/1997 | Schulte | |
| 5,598,729 A * | 2/1997 | Hoffmann | B21D 22/18 72/10.4 |
| 5,619,993 A | 4/1997 | Lee | |
| 5,669,258 A | 9/1997 | Luebke | |
| 5,759,490 A | 6/1998 | Malchesky | |
| 5,761,950 A | 6/1998 | Chiu | |
| 5,809,824 A | 9/1998 | Hiltzman | |
| 6,487,889 B1 | 12/2002 | Bates et al. | |
| 6,644,087 B1 | 11/2003 | Ralph et al. | |
| 6,755,064 B2 | 6/2004 | Butscher et al. | |
| 7,134,310 B2 | 11/2006 | Hu | |
| 7,378,048 B2 | 5/2008 | Eidenschink | |
| 7,918,819 B2 | 4/2011 | Karmarkar et al. | |
| 8,006,534 B1 | 8/2011 | Broberg et al. | |
| 8,197,453 B2 | 6/2012 | Zhou | |
| 8,298,242 B2 | 10/2012 | Justis et al. | |
| 2003/0055435 A1 | 3/2003 | Barrick | |
| 2003/0114831 A1 | 6/2003 | Wang et al. | |
| 2003/0199818 A1 | 10/2003 | Waldhauser et al. | |
| 2005/0262911 A1 * | 12/2005 | Dankowicz | B21D 7/14 72/31.04 |
| 2010/0069882 A1 | 3/2010 | Jennings et al. | |
| 2010/0147048 A1 | 6/2010 | Christofilis et al. | |
| 2010/0159117 A1 | 6/2010 | Griffin et al. | |
| 2010/0174508 A1 * | 7/2010 | Trowbridge, Jr. | G01B 21/08 702/170 |
| 2011/0265538 A1 | 11/2011 | Trieu et al. | |
| 2012/0186411 A1 * | 7/2012 | Lodahi | B23D 15/14 72/453.01 |
| 2014/0311203 A1 * | 10/2014 | Crawford | B21D 7/08 72/129 |

FOREIGN PATENT DOCUMENTS

| | | |
|---|---|---|
| EP | 1301140 A2 | 4/2003 |
| EP | 2172288 A1 | 4/2010 |

OTHER PUBLICATIONS

International Search Report and Written Opinion for International Application No. PCT/US2014/027864, dated Nov. 10, 2014, 15 Pages.

Notice of Allowance for U.S. Appl. No. 14/777,146, dated Oct. 5, 2017, 14 pages.

* cited by examiner

| | Curve Database |
|---|---|
| 1 | Curvature Image |
| 2 | Curve data points |
| 3 | Curve vectors |
| 4 | Curve splines |
| 5 | Curve overbend |
| 6 | Hysteresis |
| 7 | Sensor feedback |
| 8 | Artifical Intelligence |
| 9 | Algorithms |
| 10 | Standardized Name |
| 11 | Nickname |
| 12 | 2D/2.5D/3D |
| 13 | Length |
| 14 | Editable Points |
| 15 | Editable |
| 16 | Compatibility |
| 17 | Product Type |
| 18 | Product Name |
| 19 | Description |
| 20 | PIN |
| 21 | Size |
| 22 | ID |
| 23 | OD |
| 24 | Length |
| 25 | Contraindications |
| 26 | Inventor |
| 27 | Owner |
| 28 | Cost |
| 29 | Procedure |
| 30 | Pathology |
| 31 | Anatomy |
| 32 | Patient Characteristics |
| 33 | Male/Female |
| 34 | Height |
| 35 | Weight |
| 36 | Age |
| 37 | Feedback |
| 38 | Positive |
| 39 | Negative |
| 40 | Comments |
| 41 | Special Coding |
| 42 | Uploaded By |
| 43 | Date/Time |
| 44 | Revision |

Fig. 2

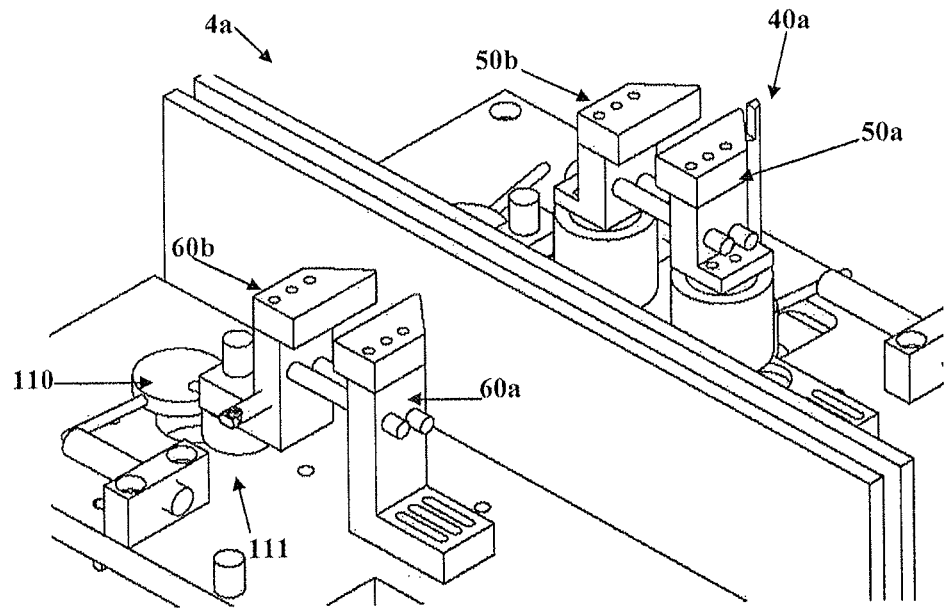
Fig. 9g
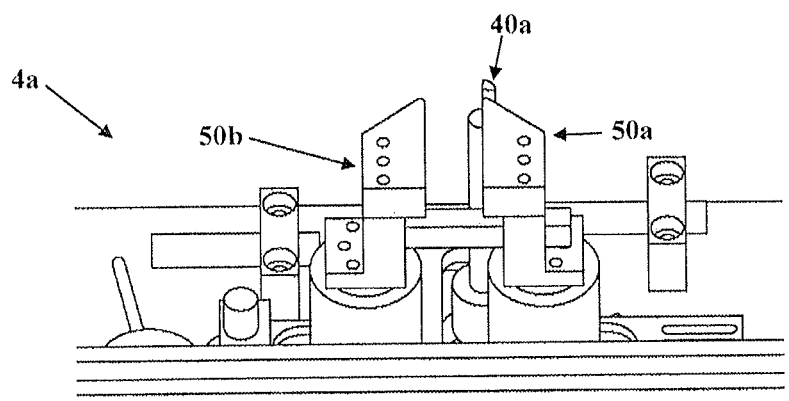
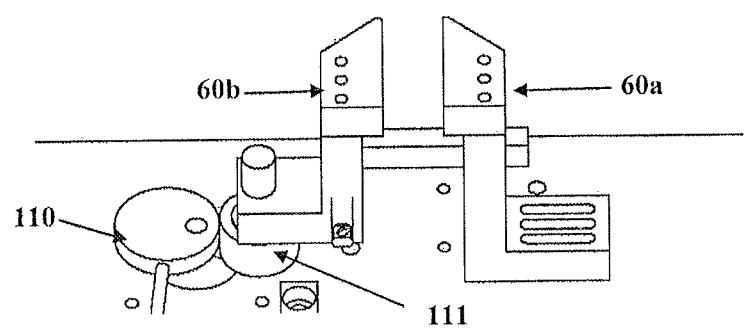
Fig. 9h

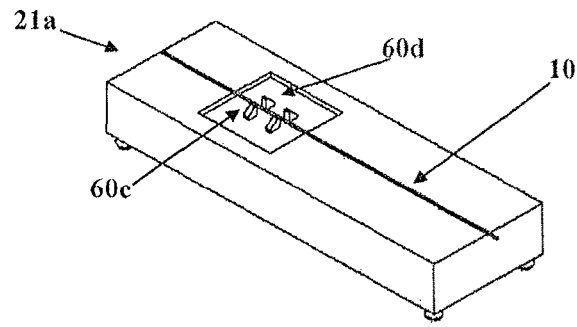
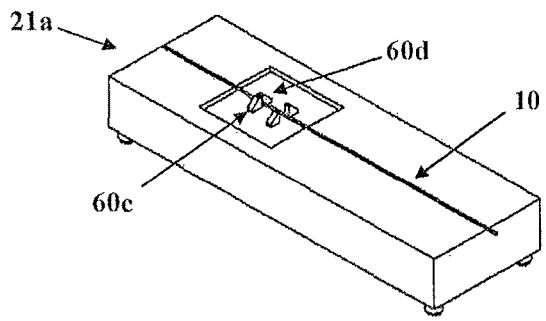
FIG. 11  FIG. 11a
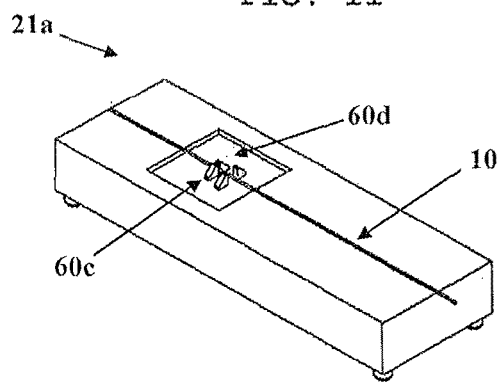
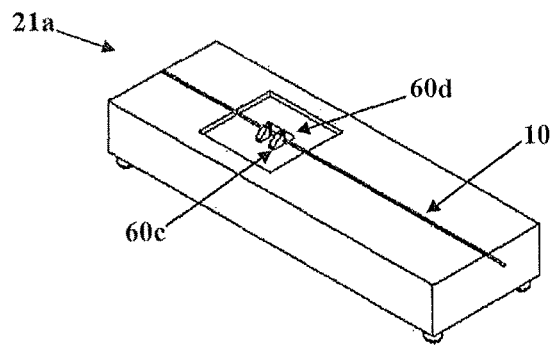
FIG. 11b  FIG. 11c
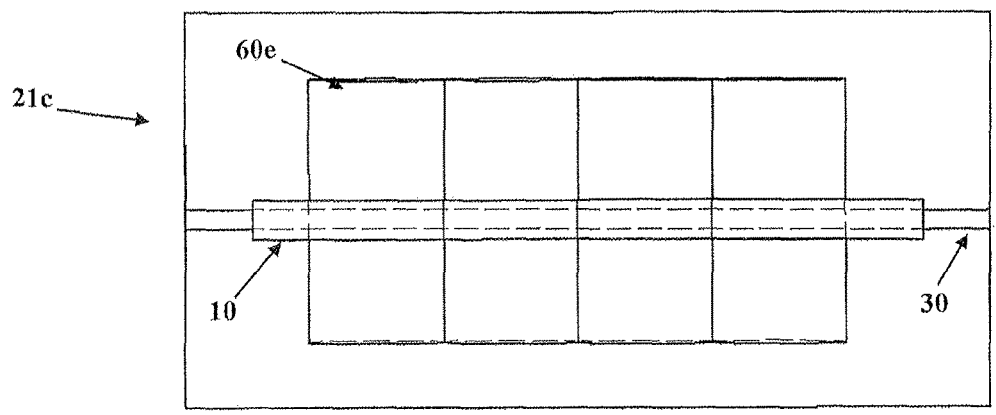
Fig. 12

MEDICAL DEVICE CURVING SYSTEM

CROSS REFERENCE TO RELATED APPLICATION

This patent application is a continuation application of U.S. patent application Ser. No. 15/806,572, filed Nov. 8, 2017, which is a divisional application of U.S. patent application Ser. No. 14/777,146, filed Sep. 15, 2015, which is the U.S. National Phase of PCT/US2014/027864, filed Mar. 14, 2014, which claims the benefit of U.S. Provisional Application No. 61/790,900 entitled "MEDICAL DEVICE CURVING APPARATUS, SYSTEM, AND METHOD OF USE," filed on Mar. 15, 2013, the contents of each of these applications being incorporated herein by reference in their entireties for all purposes.

FIELD OF THE INVENTION

This invention relates generally to an apparatus, system, and method for providing a curvature on a medical device, and more specifically to apparatuses, systems, and methods which create medical device curves in conjunction with a medical procedure.

BACKGROUND OF THE INVENTION

Minimally invasive procedures involving catheters, guidewires, needles, trocars, and other elongated medical instruments are commonly used in cardiology, radiology, neurology, urology, and other medical specialties accessing the vascular system and other anatomies. These medical devices serve to navigate the vasculature and guide other therapeutic devices to particular anatomical locations in the patient depending on the procedure. The individual characteristics of these devices are defined by their intended use, from the diagnosis and treatment of vascular disease to the transfer of fluids to and from the human body.

Catheters consist of an elongated shaft with a lumen that is inserted into the body percutaneously or via a natural orifice. The curved distal portion of a catheter is specially designed for facilitating insertion into the body and requires precise consideration for the specific radius of the catheter and the catheter diameter. The flexible distal region allows the catheter the freedom to navigate through the intricate anatomies such as the vasculature and reach those areas previously inaccessible.

The concept of a tube-like structure inserted into the body to perform a task is not a new one. Modern procedures are performed through the use of preformed catheters purchased by healthcare facilities based on frequency of use. Curved catheters have become a necessary progression from the straight catheter to facilitate selective locating (as in a renal or coronary vessel) from a remote entry site.

During the course of a procedure, it may become necessary to change the catheter to one of a smaller or larger curve radius and/or smaller or larger catheter diameter. The diameter variations in a human vessel can be affected by the age, gender and size of the patient. Therefore, each procedure presents a unique set of criteria necessary to provide the patient with the best possible care. It is expected that the required variations of curve radius or catheter size would be readily available and quickly accessible to the healthcare professionals. However, it is currently impossible for a health care facility to prepare for every possible eventuality by stocking every conceivable catheter size and curve radius. Consequently, health professionals are forced to choose the closest possible catheter diameter with the closest radius curve for their patients' individual needs. Albeit to a lesser extent, these same considerations also apply to other medical devices that navigate the vasculature to reach specific anatomies.

Containing health-care costs continues to be important, so efforts to minimize expenditures are continuously considered. In particular, budgets are being scrutinized for ways to eliminate unnecessary spending or to find ways to make the spending more effective. The cost of inventorying a wide variety of medical device lengths, diameters, and curve shapes in an effort to anticipate patient anatomical demands is expensive.

Over the years, attempts have been made to improve catheter curvature. For example, U.S. Pat. No. 8,197,453 relates to a catheter having increased curve performance through heat treatment.

U.S. Patent Application Publication No. US2003/0114831 relates to a catheter having improved curve retention and a method of manufacture.

U.S. Pat. No. 3,719,737 relates to a method of making a preformed curved epidural catheter.

U.S. Pat. No. 7,378,048 relates to a method for forming catheter curves.

U.S. Pat. No. 5,619,993 relates to a method of controlling curvature of a medical device.

U.S. Pat. No. 4,292,270 relates to a method and apparatus for making coude catheters.

U.S. Pat. No. 3,839,841 relates to a method for forming and sterilizing catheters.

U.S. Patent Application Publication No. US 2010/0147048 relates to devices, systems and methods for automated wire bending.

U.S. Pat. No. 7,134,310 relates to a tube bender.

U.S. Pat. No. 8,298,242 B2 relates to a system for the bending of an elongate member.

U.S. Patent No. US 2011/0265538 A1 relates to a system for the multidimensional bending of an elongate member.

U.S. Pat. No. 3,866,458 relates to a bender for contouring surgical implants.

U.S. Pat. No. 6,644,087 B1 relates to a rod bender for bending surgical rods.

U.S. Pat. No. 6,755,064 B2 relates to a bending method and robotic device used to add curvature to orthodontic archwires and other medical devices.

U.S. Patent No. US 2003/0055435 A1 relates to a system for shaping orthopaedic implants.

U.S. Patent No. US 2010/0069882 A1 relates to an elongated medical device that exhibits preferential bending.

U.S. Patent No. US 2013/0091921 relates to a handheld rod bender.

U.S. Patent No. US 2003/0114831 A1 relates to a method for treating polymeric materials suitable for catheter construction with a nucleating agent.

U.S. Patent No. US 2003/0199818 A1 relates to a series of temperature-activated actuators that impart a curve on an elongated medical device.

U.S. Patent No. US 2010/0159117 A1 relates to a super-elastic guidewire with shape retention tip.

U.S. Pat. No. 7,378,048 B2 relates to a method and apparatus for forming catheters and catheter curves using ferromagnetic materials exposed to an alternative magnetic field.

U.S. Pat. No. 5,761,950 relates to a tube bender.

U.S. Pat. No. 5,502,997 relates to a gripper and mandrel assembly for a stretch type tube bender.

U.S. Pat. No. 5,593,708 relates to an apparatus for bending a plastic pipe.

U.S. Pat. No. 7,918,819 B2 relates to a deflectable tip guiding device with a variable curve on the tip.

U.S. Pat. No. 5,619,993 relates to a pressure source used to control the curvature of a medical device.

U.S. Pat. No. 5,809,824 relates to a tool for producing a loop in a straight wire.

U.S. Pat. No. 8,006,534 B1 relates to a wire or rod bender adaptable to bend a variety of sizes of wire to at least one desirable angle.

U.S. Patent No. US 2010/0147048 A1 relates to devices, systems, and methods for automated wire bending.

U.S. Pat. No. 5,669,258 relates to a manual tube bender with angle indicator.

U.S. Pat. No. 7,134,310 relates to a tube bender including a pushing device, guide rail, and curved bending die.

U.S. Pat. No. 6,487,889 B1 relates to a tube bender that is able to bend multiple tubes at various angles.

Patent No. EP 0417865 B1 relates to the method of manufacture of a drainage catheter.

Patent No. EP 0600676 A2 relates to a steerable catheter with an adjustable bend location.

Patent No. EP 1301140 B1 relates to a bending machine for a medical device, more specifically an orthodontic archwire.

Patent No. EP 2172288 A1 relates to a bending method for suture needles.

Accordingly, each of the aforementioned proposals has limitations and there is still a need for novel apparatuses, systems, and methods which create medical device curves.

SUMMARY OF THE INVENTION

According to one aspect of the invention, an apparatus is provided for curving an elongated medical device. It includes a forming unit, having an external surface, positioned adjacent a path along which the elongated medical device is advanced, the forming unit having a support and a heat source. It also includes a bending tool, having an external surface, configured to move with respect to the forming unit and to apply a bending force to the elongated medical device such that a distal portion of the elongated medical device is imparted with a permanent curve greater than that on a proximal portion of the elongated medical device. A barrier is positioned to prevent the elongated medical device from contacting the external surface of the forming unit and the external surface of the bending tool, the barrier being configured to permit movement of the bending tool with respect to the forming unit while maintaining sterility of the elongated medical device.

The apparatus optionally includes a mandrel configured to support the elongated medical device as it is imparted with a permanent curve. The mandrel can have a composite structure and contain one or more materials configured to be heated by induction. For example, the mandrel optionally contains at least one element selected from the group consisting of iron, aluminum, titanium, copper, nickel, tin, barium, bismuth, chromium, manganese, and cobalt.

The heat source of the forming unit is optionally configured to produce an inductive field. The support and heat source of the forming unit are optionally separate structures. The forming unit is optionally configured to allow movement of the elongated medical device along the path, and can be indexed in increments to advance the elongated medical device along the path. The bending tool can be configured to overbend the elongated medical device such that a permanent curve imparted on the elongated medical device is different when after the elongated medical device is separated from the apparatus.

The apparatus can include a controller configured to control the apparatus and/or a sensor to monitor the overbend, which sensor can be coupled to the bending tool. The controller can be programmed with logic for establishing overbend of the elongated medical device.

The heat source of the forming unit can configured to heat the medical device through conduction, convection, or radiation. The barrier can include an elastomeric material that allows movement of the bending tool with respect to the forming unit by elongating or by unfolding, for example. The barrier can be formed from a material selected from the group consisting of silicone, polyurethane, polyolefin, polyester, nylon, fiberglass, nitrile, PTFE, FEP, ETFE, and any combination thereof. The barrier can also include a drape configured to correspond to the contour of the apparatus and/or a sleeve that at least partially encompasses the medical device. The barrier can include a portion of the bending tool and forming unit external surfaces that contact the medical device.

The barrier can also include a source of electromagnetic radiation. If so, the source of electromagnetic radiation can be configured to generate ultra violet radiation with a wavelength between 200 and 280 nm. The source of electromagnetic radiation can include light emitting diodes configured to generate the ultra violet radiation. The bending tool can also include a transparent material configured to permit transmission of electromagnetic radiation, and the bending tool can include at least one textured external surface configured to allow electromagnetic radiation to refract from the external surface. The apparatus can optionally include a guard positioned to prevent electromagnetic radiation from reaching a user of the apparatus.

The elongated medical device curved by the apparatus can include an intravascular catheter and can be selected from the group consisting of a guiding catheter, a diagnostic catheter, and a microcatheter.

According to another aspect of the invention, an apparatus is provided for applying a custom curvature to a medical device. The apparatus includes at least one base positioned to support a grasping fixture, a bending tool, a forming unit, at least one barrier, and including a mandrel for maintaining the medical device curvature. The grasping fixture is provided to move a distal portion of the medical device relative to the base along at least one axis. The bending tool is configured to move with respect to the forming unit along at least one axis. The at least one barrier is positioned between at least the grasping fixture and the medical device and the bending tool and the medical device. Sterility is maintained on the medical device as a curve is imparted along a distal portion of the medical device between the bending tool and the forming unit.

In this form of apparatus, the mandrel can have a composite structure and can contain one or more materials configured to be heated by induction. The mandrel can contain at least one element selected from the group consisting of iron, aluminum, titanium, copper, nickel, tin, barium, bismuth, chromium, manganese, and cobalt.

The forming unit is optionally configured to produce an inductive field, and the grasping fixture is optionally configured to be indexed in increments to advance the medical device along a path. Also, the bending tool is optionally configured to overbend the medical device such that a permanent curve imparted on the medical device is different when the medical device is separated from the apparatus.

The apparatus can include a controller configured to control the apparatus and/or a sensor to monitor the overbend. Such a sensor can be coupled to the bending tool. The controller is optionally programmed with logic for establishing overbend of the elongated medical device.

The apparatus optionally includes a heat source configured to heat the medical device through conduction, convection, and/or radiation. The barrier can include an elastomeric material that allows movement of the bending tool with respect to the forming unit by elongating or by unfolding, and the barrier can be formed from a material selected from the group consisting of silicone, polyurethane, polyolefin, polyester, nylon, fiberglass, nitrile, PTFE, FEP, ETFE, and any combination thereof.

The barrier can include a drape configured to correspond to the contour of the apparatus. The barrier can include a sleeve that at least partially encompasses the medical device. The barrier can also include a portion of the bending tool and forming unit external surfaces that contact the medical device.

The barrier optionally includes a source of electromagnetic radiation that can generate ultra violet radiation with a wavelength between 200 and 280 nm. The source of electromagnetic radiation can include light emitting diodes configured to generate the ultra violet radiation. The bending tool can include a transparent material configured to permit transmission of electromagnetic radiation and/or at least one textured external surface configured to allow electromagnetic radiation to refract from the external surface. A guard can be positioned to prevent electromagnetic radiation from reaching a user of the apparatus.

According to yet another aspect of the invention, an apparatus for curving an elongated medical device can include a heating means, a mandrel means, a curving means, and a barrier means, wherein a central axis is defined by the centerline of the elongated medical device having a proximal portion and a distal portion along its length, and wherein the distal portion of the elongated medical device is imparted with a permanent curve greater than that on the proximal portion, while maintaining sterility of the elongated medical device.

According to yet another aspect of this invention, a system for curving an elongated medical device is provided. The system includes a curve database storing information corresponding to a plurality of curves that can be applied to the elongated medical device, the information for each of the curves including an image of the curve, a curve identifier, and a size of the elongated medical device. The system also includes a user interface configured for selecting information stored in the curve database by a user of the system. And a curving apparatus is configured for curving the elongated medical device based on information stored in the curve database selected by the user.

The system optionally includes a user network configured for updating the curve database. A communication device can be configured to connect with an imaging unit providing information specific to a patient anatomy to the system. The user interface can be configured for selecting information through hand, voice, or foot gestures.

The system's curving apparatus can include a sensor configured for curving the elongated medical device based on feedback from the sensor of the curving apparatus. The system can be configured for curving the elongated medical device based on data from the imaging unit. It can also be configured to heat the elongated medical device in order to maintain a permanent curve, and can overbend the elongated medical device in order for the curve on the elongated medical device to approximate the curve in the curve database.

The system can be configured to maintain sterility of the elongated medical device, and the user interface can be further configured to be operated by a user wearing sterile attire.

The curve database of the system may include curve overbend information, pathology information, anatomy information, procedure information, and patient characteristics corresponding to one or more of the curve.

The system can be configured to curve the elongated medical device with an S shaped curve and/or to curve the elongated medical device with a 3-dimensional curve.

According to yet another aspect of the invention, a method is provided for curving an elongated medical device. The method includes positioning the elongated medical device in a curving apparatus; selecting a curve from a curve database storing information corresponding to a plurality of curves that can be applied to the elongated medical device using a user interface, thereby communicating information corresponding to the selected curve to the apparatus for curving the elongated medical device; and actuating the apparatus to curve the elongated medical device based on information stored in the curve database.

The method can include removing the elongated medical device from a sterile package, viewing the patient anatomy from an imaging unit, selecting an image from the imaging unit, communicating information associated with the image to the curving apparatus, and/or cooling the curved elongated medical device. The method can also include altering the selected curve using the user interface, scaling the selected curve, and/or showing points on the selected curve and repositioning one or more of the points, thereby altering the shape of the selected curve.

The method optionally includes selecting a curve based on additional dimensional information; on a product type, name, or description; and/or on a pathology or anatomy from the curve database. The method can include removing the elongated medical device from the apparatus and using the elongated medical device during a sterile medical procedure, including optionally actuating the apparatus within a hospital laboratory.

According to still another aspect of the invention, a method is provided for curving an elongated medical device including positioning a barrier to prevent the elongated medical device from contacting both a forming unit and a bending tool of an apparatus for curving the elongated medical device; selecting a curve from a curve database storing information corresponding to a plurality of curves that can be applied to the elongated medical device using a user interface, thereby communicating information corresponding to the selected curve to the apparatus for curving the elongated medical device; and actuating the apparatus to curve the elongated medical device based on information stored in the curve database.

The method can include removing the elongated medical device from a sterile package; viewing the patient anatomy from an imaging unit; selecting an image from the imaging unit and communicating information associated with the image to the curving apparatus; cooling the curved elongated medical device; altering the selected curve using the user interface; scaling the selected curve; and/or showing points on the selected curve and repositioning one or more of the points, thereby altering the shape of the selected curve.

The method can include selecting a curve based on additional dimensional information from the curve database; selecting a curve based on a product type, name, or description from the curve database; and/or selecting a curve based on a pathology or anatomy from the curve database.

The method optionally includes removing the elongated medical device from the apparatus and removing the barrier from the elongated medical device, and/or removing the elongated medical device from the apparatus and using the elongated medical device during a sterile medical procedure. It can also include actuating the apparatus within a hospital laboratory.

BRIEF DESCRIPTION OF DRAWINGS

FIG. 2 is a table view listing information stored in an embodiment of the curve database.

FIG. 9g is an enlarged pictorial view of the curving apparatus embodiment of FIG. 9.

FIG. 9h is an enlarged pictorial view of the curving apparatus embodiment of FIG. 9.

FIG. 11 is a pictorial view of a primary base embodiment with linear grasping fixtures.

FIG. 11a is a pictorial view of the primary base embodiment of FIG. 11 with the back set of linear grippers converged on a device FIG. 11b is a pictorial view of the primary base embodiment of FIG. 11 with back linear grippers converged on a device and advancing it.

FIG. 11c is a pictorial view of the primary base embodiment of FIG. 11 with two sets of liner grippers converged on the medical device.

FIG. 12 is an enlarged pictorial view of the primary base embodiment of FIG. 11 with horizontal roller supports

DETAILED DESCRIPTION OF THE INVENTION

Figure 1:
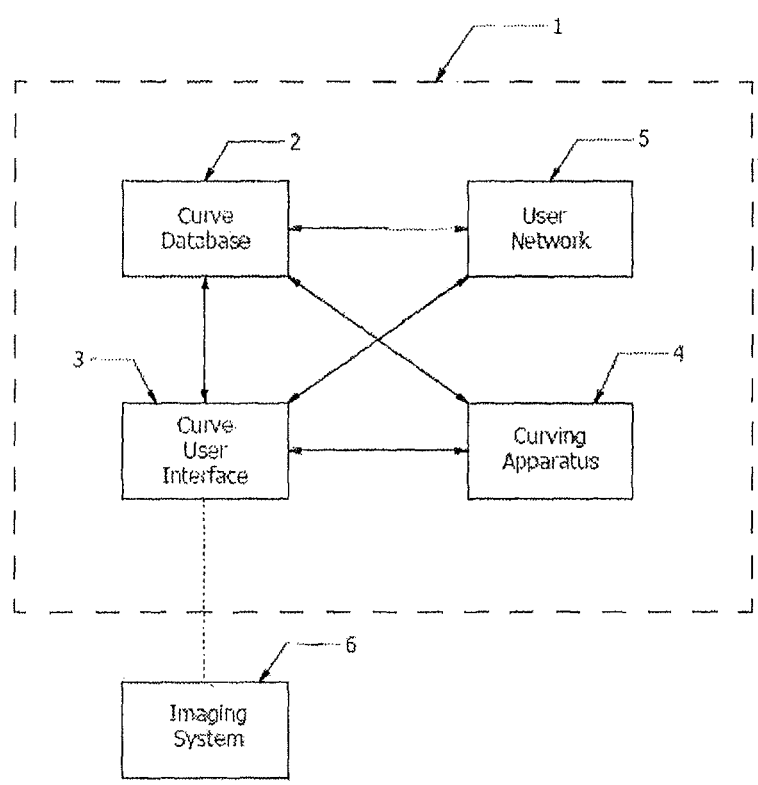
FIG. 1 is a diagram illustrating an embodiment of the features and system used to curve a medical device.

Although the invention is illustrated and described herein with reference to specific embodiments, the invention is not intended to be limited to the details shown. Rather, various modifications may be made in the details within the scope and range of equivalents of the claims and without departing from the invention.

This invention makes it possible to provide a medical device, with the appropriate curvature for a particular patient's anatomy, on demand during a procedure. This invention therefore makes it possible to save time during the procedure, provide optimal care to the patient, and reduce healthcare inventory expenses.

More specifically, one aspect of this invention provides a system for producing a medical device having a custom curvature. The system includes a database of curvatures maintained on a computer. The database stores information for each of the curvatures including an image of the curvature, at least one physical anatomy with which the curvature is intended to be used, at least one pathology associated with a patient, at least one medical procedure in which the curvature is intended to be used, and a source of the curvature (though the source may remain anonymous). The system also includes a user network coupled to the database for accessing information stored in the database and for supplementing information stored in the database. An interface is coupled to the database and positioned for use by a medical professional during a medical procedure. The interface is configured to communicate a selection of a custom curvature and to retrieve data corresponding to the custom curvature from the database. The user interface can be a touch screen tablet computer. The curving apparatus is coupled to the database, the apparatus having a fixture for grasping a catheter, and a tool for applying a selected custom curvature to the catheter, optionally including a bending tool, wherein the apparatus is configured to cause movement of the catheter and the tool with respect to one another.

The system optionally includes an imaging device that is connected through a wired or wireless network. The imaging device can be coupled to hospital imaging equipment such as ultrasound, fluoroscope, x-ray, MRI, CT-Scan, TEE, ICE and other equipment.

According to another aspect of the invention, a system for providing custom curvatures for medical devices includes a database of curvatures maintained on a computer, the database storing information for each of the curvatures including an image of the curvature, at least one physical anatomy with which the curvature is intended to be used, at least one medical procedure in which the curvature is intended to be used, and a source of the curvature (which may optionally be anonymous as mentioned above). The system also includes an interface coupled to the database, the interface being configured to receive from a user a custom curvature for storage in the database; receive from a user a request for a custom curvature based on at least one of the image of the curvature, a pathology associated with a patient, the physical anatomy with which the curvature is intended to be used, the medical procedure in which the curvature is intended to be used, and the source of the curvature (though this may also be anonymous); retrieve data corresponding to a requested custom curvature from the database; and communicate to the user the retrieved data corresponding to the requested custom curvature. In the system, the curvature can be represented by series of points and splines.

According to yet another aspect of the invention, the invention provides a method for producing a medical device having a custom curvature on demand during a medical procedure. The method includes accessing from a site of the medical procedure a database of curvatures maintained on a computer via an interface capable of being coupled to the database, the database storing information for each of the curvatures including an image of the curvature, at least one physical anatomy with which the curvature is intended to be used, at least one pathology associated with a patient, and at least one medical procedure in which the curvature is intended to be used, and a source of the curvature (again this may be anonymous). The method also includes selecting a custom curvature from among those stored in the database based on at least one of the images of the curvature, the pathology associated with a patient, the physical anatomy with which the curvature is intended to be used, the medical procedure in which the curvature is intended to be used, and the source of the curvature (though this also may be anonymous). In the method, an apparatus is activated at the site of the medical procedure, the apparatus being coupled to the database to form the custom curvature.

Optionally, a user can create a completely new curvature or edit an existing curvature using the system and method of this invention. This can be done by touching points and splines of a curve and moving points in 2 dimensional or 3 dimensional space while the original spline position is locked in the background.

Yet another aspect of this invention provides an apparatus for applying a custom curvature to a medical device. The apparatus includes a mandrel optionally formed from solid, liquid or gas for positioning internal or external of the medical device. The mandrel is preferably malleable and heat conductive. The apparatus also includes a base positioned to support the device, optionally including primary and secondary base components. A fixture is provided for grasping the device, the fixture being coupled to the base for movement with respect to the base along at least one axis. A tool is also provided for applying the custom curvature to the device, the tool being coupled to the base for movement with respect to the base along at least one axis. At least one barrier is configured to be positioned between at least one of the fixture and the device and the tool and the device, the barrier being configured to maintain sterility of the device.

The apparatus can optionally include a controller; a heating unit optionally selected from conduction, convection, radiance, laser, electromagnetic radiation, microwave, induction, electric current, friction, chemical, or heating strip or hot-air source; and a forming platform movable to create three-dimensional shapes. Preferably, the apparatus is configured to cause incremental movement of the fixture and the tool such that the device and the tool move with respect to one another to form the curvature.

Referring now to selected embodiments of the invention, FIG. 1 is a diagram of the medical device curving system 1, which may be in communication with an imaging system 6. Components of the medical device curving system 1 are a curve database 2, a curve user interface 3, a curving apparatus 4, and a user network 5. The object of the medical device curving system 1 is to provide a user the ability to create a custom curvature medical device for a medical procedure. In this case, the user may be a physician, nurse, physician assistant, technician, medical professional, or any individual or group who has the need for a specific curve shape on a medical device. The medical device is most generally a catheter, but could also be a guidewire, a needle, a trocar, an introducer, a guiding catheter, a core, a stylet, or any other elongated medical device used for a medical procedure that would benefit from having curvature imparted along its length. Specific types of catheters that can benefit from the medical device curving system 1, which are generically referred to as intravascular catheters, are guiding catheters, diagnostic cardiology catheters, diagnostic peripheral catheters, and microcatheters. The term "permanent curve" is used to denote a curve, shape, arc, or curvature that has been imparted to the medical device in a manner where it will remain relatively intact on the medical device during the normal operation of the device. A curve may be a simple arc, more than one arc such as an S curve, or a combination of arcs, lines, angles, paths, and splines with infinite variations in two, two and a half, or three dimensions.

The medical device curving system 1 may be operated in any order, and each of the components may communicate with each other either directly or indirectly; through direct or indirect connections or through physical wires or wirelessly. The curve database 2 stores curvature information on a computer or any device capable of storing and releasing information. The curve database 2 is accessible by the user from any curve user interface 3, user network 5, or curving apparatus 4. The goal of the curve database is to store information on every curve shape that is currently used on a medical device, and every new curve shape that is tested and or developed for a medical device. This information may then be accessed by the user via the curve user interface 3. The curve user interface 3 can also be a computer, tablet, smart phone, foot, toe, hand, finger, voice, eye, stylet, mouse, brain, or any other controlled device that enables the user to select the desired curvature and view, hear, or feel the necessary attributes. The curve user interface 3 will also enable the user to create a completely new curvature or easily edit an existing curvature. The curvature may be stored and presented in many different ways, including but not limited to a two dimensional graphic image consisting of points, lines, curves, and splines, or it could be represented by filled or shaded areas depicting the curve, or it could be similar to a solid model and consist of surfaces, solids, meshes, and nodes. The curvature may also be presented with numbers or directions or explained to the user. As with current computer aided design (CAD), solid modeling software, rendering, illustrating, and designing software, there are many forms that a curvature can be displayed in two dimensions, two and one half dimensions, or three dimensions. What is important is that the user can easily understand the curvature presented and create or edit the curvature. A current preferred curve user interface 3 consists of a touch screen tablet where the curvature is presented as a series of points and splines. Touching the points provides the ability to move the points in 2 dimensional space while the original spline position is locked in the background. This allows the user to easily manipulate the spline and see the exact dimensional changes from the original curvature. Alternatively the user can manually draw their own curvature using a draw feature on the user interface. The system will automatically smooth the drawing to a useable model for the curving apparatus. Two and one half dimensions is enabled by the user by selecting a point on the curvature and selecting an angle for rotation of the curvature in a direction perpendicular to the tablet screen. The angle is represented on the two dimensional screen by skewing the curvature on a grid. Three dimensions is enabled by rotating the curvature with a spherical navigator tool, and using lighting and a shadow to represent the three dimensional shape on the two dimensional screen. The user will easily be able to rotate to a front view, side view, top view or an isometric view.

An imaging system 6 may also connect through a wired or wireless network to the curve user interface 3 allowing two and three dimensional images and video from hospital imaging equipment such as ultrasound, fluoroscope, x-ray, Magnetic Resonance Imaging (MRI), Computed Tomography scans (CT-Scan), transesophageal echocardiograms (TEE), intracardiac echocardiography (ICE), and other equipment that can provide valuable imaging of the body and associated anatomy and pathology to be superimposed on the curvature on the user interface screen. Calibration of the curvature size and imaging equipment will be necessary to ensure that the scaled sizes are equivalent. The addition of these images to the selection, creation, and editing of curvature will be extremely useful to the user as it will enable the medical device curvature to accurately model the associated patient anatomy for the particular procedure.

A user network 5, allows the users the ability to communicate with each other and any associated groups of users as part of the medical device curving system 1. This communication provides additional information to the curve database 2 that can be helpful to the user in the selection of an appropriate curvature for a particular patient, pathology, anatomy, and procedure. Successful attempts, failed attempts, comments, suggestions, likes and dislikes with different curvatures in particular situations is how the user community and the medical device curving system 1 learn the optimal approach. The user network 5 may connect through any wired or wireless network or by any other communication method to provide the user access to the information in the curve database 2 and curve user interface 3. The user network 5 can even connect with the curving apparatus 4 through the curve user interface 3 so as to allow a user to remotely operate the curving apparatus 4. This is particularly helpful for performing remote procedures or providing guidance to a less experienced user remotely. As with most database networks, security of data and user information is of extreme importance. The medical device curving system 1 would incorporate appropriate controls to ensure that the data and network are appropriately secure.

The curving apparatus 4 is the component within the medical device curving system 1 used to apply a custom curvature to a medical device based on curvature information stored in the curve database 2 or from the curve user interface 3. The curving apparatus 4 is configured to apply a curvature to the medical device while maintaining sterility of the medical device, so that the medical device may be used during a procedure the moment after the curvature is imparted to the medical device. It is important that the performance, quality characteristics, and physical (other than curvature), biological, and toxicological attributes of the medical device are not negatively altered during the curving process.

The curving apparatus 4 has the ability to take analog and digital information and convert it to mechanical motion. In a similar fashion to a two dimensional plotter and a three dimensional printer, or a numerically controlled milling machine, raster and vector images can easily be transformed into mechanical motion through stepper and servo motors, linear motors, piezo electric actuators, and newer smart material type actuators. Positioning sensors, encoders, and other feedback devices ensure that the motion is accurate and repeatable. This motion enables the curving apparatus 4 to consistently apply a curvature to a medical device.

The curving apparatus 4 will significantly benefit from the information communicated by the curve database 2 and the curve user interface 3, but it may also be necessary that the curving apparatus 4 operate independent and disconnected from these components. A medical procedure may rely on the operation of the curving apparatus 4 to provide the appropriate curvature medical device for a routine procedure where there is no inventory of the appropriate curvature device. The curving apparatus may be preprogrammed with all of the standard curvatures and associated information that are currently used in the hospital setting. The curving mechanism of the apparatus can also be manually controlled by the user bending the medical device into any shape. However, when connected to the curve user interface 3, the curving apparatus 4 has the ability to apply a precise custom curvature to a medical device specific to the patient, patient anatomy, patient pathology, and patient procedure. This type of educated customization could significantly reduce the procedural time, radiation exposure to the patient and user, and provide better outcomes.

The medical device curving system 1 can be operated in any environment, it is even contemplated to operate with a portable electrical system such as batteries or a generator in instances where electrical power is not available. The optimal environment, however, is the hospital laboratory where the sterile medical devices are being used e.g., a cath lab, radiology lab, neurology lab, EP lab, ER, or OR. In these instances, the sterile medical device can be curved and immediately provided for use in a sterile medical procedure without additional concern for the sterility of the device being compromised during transport. A sterile medical procedure can be any type of medical procedure where access to the living body requires sterile technique to be practiced to minimize the possibility of infection to the living body. This typically means that the personnel performing the medical procedure are wearing sterile attire, and the living body and surrounding areas are covered with sterile drapes. The living body can be a human or an animal.

FIG. 2 is a table depicting a listing of the curve database 2 information for each curvature, As a searchable, relatable database, the curve database 2 allows curvatures to be searched, selected, and compared. It enables the user to perform advanced and complex searches to optimize a curve shape for a particular patient physique and pathology. It is conceivable that the curve database 2 could have the ability to learn, have artificial intelligence, or have fuzzy logic to make decisions for the user on the optimal curvature for a particular procedure. If connected to an imaging system 6 (FIG. 1), the curve database 2 could store images and video of a particular anatomy and pathology and compare this additional information as part of the search criteria. The curve database 2, can also have the ability to run various algorithms, subroutines, software, or search engines so that it can provide greater value to the user in quickly identifying a curvature based on a single or set of parameters.

Most of the information depicted in the curve database 2 is self-explanatory. However, some discussion is warranted for several of the forty four lines pictured in FIG. 2. The curvature image (line 1) could be a static picture, a video, a holograph, or a model capable of being manipulated and viewed on the curve user interface 3. Curve overbend data (lines 5 through 9) may be stored in the database for particular devices, or be based on feedback from sensors within the curving apparatus, may be programmed as a function of the device size and radius being created, or may use learning software to update itself with respect to the result of each curve based on sensors or user input. The 2D/2.5D/3D nomenclature (line 12) helps the user isolate curvature searches based on of the curvature is in two dimensions, two and one-half dimensions (meaning that a portion of the curve is angled out of plane at a single point), or three dimensions. Having the option to make the curvature editable (line 14) by a user other than the originator of the curve may also be controlled in the curve database 2. Compatibility (lines 16 through 24, line 20 denotes "part number") of the curvature with specific medical devices—of which characteristics can be defined—will ensure that the curving apparatus 4 can actually apply the curvature to a particular medical device. The curvature can also be contraindicated (line 25) for a particular procedure due to the curvature being inadequate or having the potential to cause harm to the patient. The curvature can also have a cost (line 28) associated with using the particular curvature. This is of particular interest to users who spend time and resources to develop a particular curvature and would like to be paid by other users for use of the curvature. Special coding (line 41) involves the need for specific coding instructions to allow the curving apparatus 4 to properly apply the curvature to the medical device. These could be special heating instructions or other characteristics that are unique to that curvature. The user will also have the ability to add more entries to the curve database depending on the needs of the user.

The curve database 2 can be a relational database, where the data is stored and managed in the cloud. This can be created as a custom coded website similar to wwwitunes.com or www.istockphoto.com, or can be configured from pre-existing cloud based systems such as autodeskplm360 (by Autodesk Inc.) and/or Netsuite (by Netsuite Inc.), all of which have the ability to upload, download, and store enormous amounts of data, and securely process transactions. The curvature image (line 1) may also be created using a pre-existing cloud based system such as www.tinkercad-com or wwww.auttocad360.com, or can be custom coded. The curve database 2 can also have the ability to reside on the curving apparatus 4, similar to itunes (Apple Inc.) which allows the curving apparatus 4 to operate independent of the internet or cloud, though is able to synchronize with the cloud based curve database 2 through a wired or wireless connection on a regular basis to maintain current, similar to how Microsoft Windows or Symantec perform regular updates.

Figure 3:
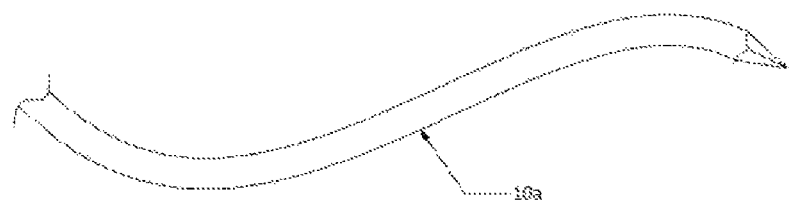
FIG. 3 is a pictorial view of an embodiment of a curved trocar

FIG. 3 is a pictorial view of a curved trocar 10a for which the curvature could be imparted by the medical device curving system 1.

Figure 4:
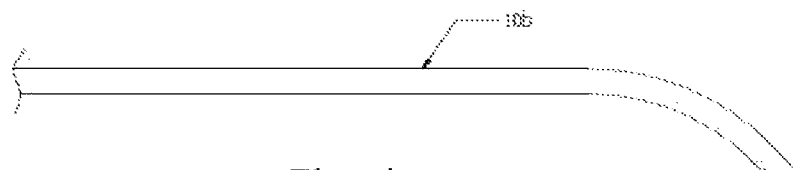
FIG. 4 is a pictorial view of an embodiment of a curved needle

FIG. 4 is a pictorial view of a curved needle 10b for which the curvature could be imparted by the medical device curving system 1.

Figure 5:
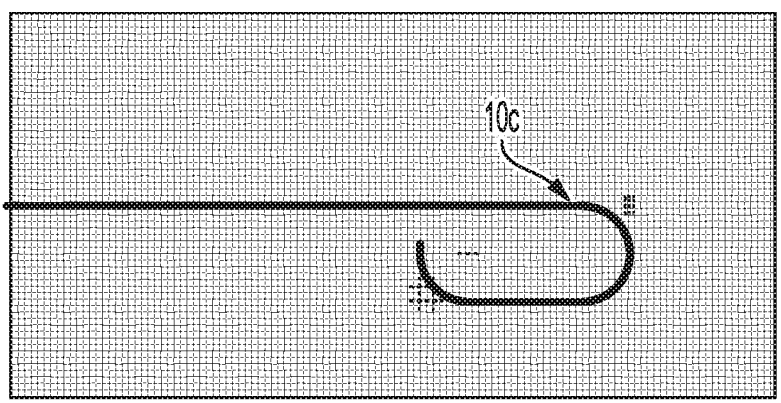
FIG. 5 is a pictorial view of an embodiment of a curved catheter in two dimensions.

FIG. 5 is a pictorial view of a curved catheter 10c in two dimensions for which the curvature could be imparted by the medical device curving system 1. A grid on the background shows how the catheter 10c might be viewed on the curve user interface 3, where a scale could be provided in English or Metric units of various scales to help interpret the curve dimensions, especially when zooming in or out.

Figure 6:
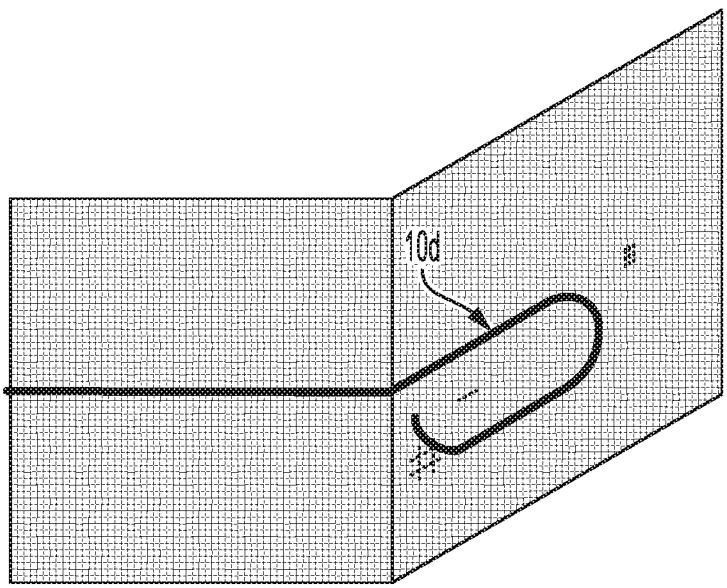
FIG. 6 is a pictorial view of an embodiment of a curved catheter in two and one half dimensions.

FIG. 6 is a pictorial view of a curved catheter 10d in two and one half dimensions for which the curvature could be imparted by the medical device curving system 1. A grid on the background shows how the catheter might be viewed on the curve user interface 3, where the vertical line at the grid skew denotes the point at which the catheter 10d is curving out of plane.

Figure 7:
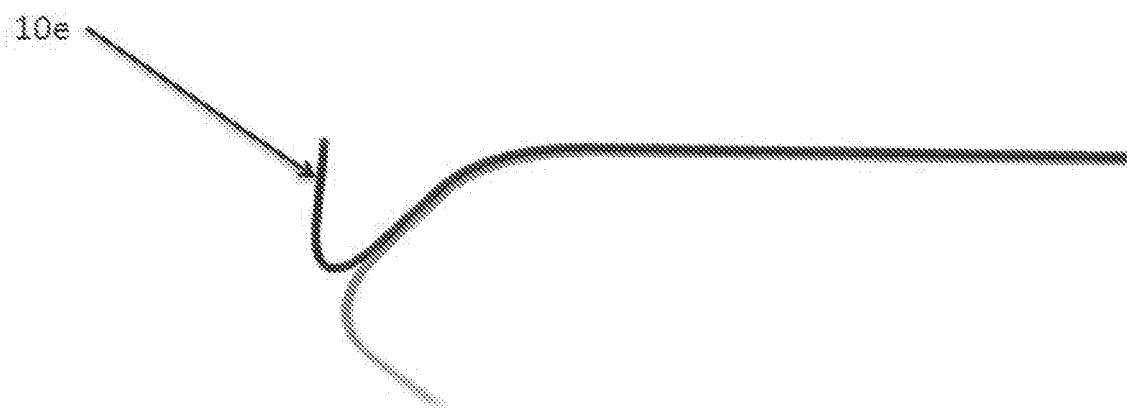
FIG. 7 is a pictorial view of an embodiment of a curved guidewire in three dimensions.

FIG. 7 is a pictorial view of a curved guidewire 10e in three dimensions for which the curvature could be imparted by the medical device curving system 1. A shadow on the background shows how the guidewire 10e might be viewed on the curve user interface 3, where the shadow shows a reflection of the guidewire 10e curvature. As the guidewire 10e is rotated or manipulated on the curve user interface 3, the shadow helps the user understand and appreciate the three dimensional geometry.

The curved trocar 10a (FIG. 3), curved needle 10b (FIG. 4), curved catheter 10c (FIG. 5), and curved guidewire 10e (FIG. 7) are all examples of medical devices that could benefit from custom curvature applied by the medical device curving system 1. They could be made from metal, plastic, elastomer, or composite materials and be hollow, solid, or a combination of the above.

Figure 8:
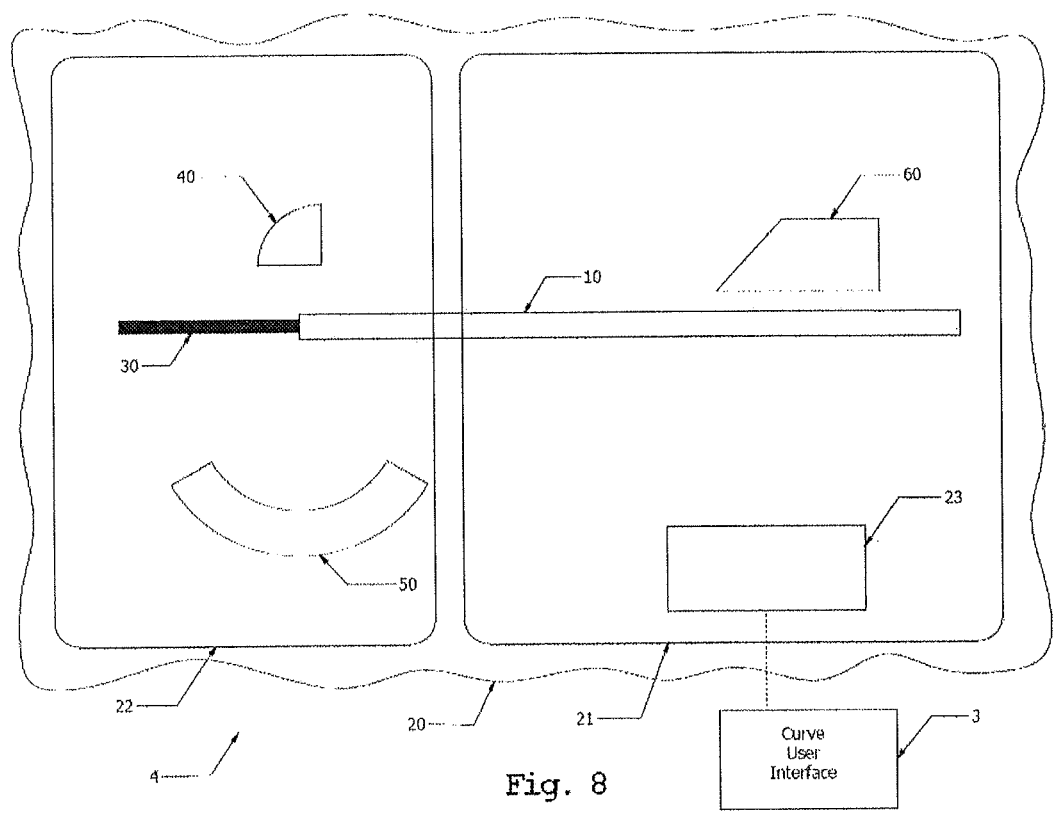
FIG. 8 is a pictorial plan view of a curving apparatus embodiment.

FIG. 8 is a pictorial plan view of a curving apparatus 4 embodiment with a medical device 10, a support mandrel 30 extending longitudinally inside the lumen of the medical device 10, a bending tool 40, a grasping fixture 60, a primary base 21, a secondary base 22, a barrier 20, a controller 23, and a forming unit 50. The curve user interface 3 can be connected to the controller 23 as part of the medical device curving system 1 (not shown) as previously discussed.

The curving apparatus 4 is configured to hold a medical device 10 with a grasping fixture 60 that is coupled to a primary base 21. Based on the specific instructions from the controller 23, the grasping fixture 60 can move relative to the medical device 10, or it can grasp and move the medical device 10. This allows the medical device 10 to be placed in any relative position within either the primary base 21 or the secondary base 22. The bending tool 40 can also move relative to the medical device 10 and the primary base 21 or the secondary base 22. The purpose of the bending tool 40 is to receive specific curvature geometry instructions from the controller 23 and physically apply this geometry to the medical device 10. In this manner the controller 23 is functioning in a similar fashion to a computer numerical control (CNC). For example a 4-axis motion controller from Arcus Technology Inc. can independently control 4 stepper motors which can be configured to move the grasping fixture 60, the bending tool 40, the forming unit 50, and the secondary base 22. Code configured to take the instructions from the curve database 2 (FIG. 2) can be custom created to interface with the controller 23, or currently available software such as drivers from Condor Graphics Technologies can be configured to create the motion.

This act of physically applying the geometry can be termed "bending" the medical device 10. The support mandrel 30 may be used when the medical device has a lumen or inner diameter that cannot be maintained during the bending process. A trocar 10a (FIG. 3) that does not have a lumen would not require the use of an internal support mandrel 30 but may benefit from an external mandrel. A heavy walled medical device (not shown) where the integrity of the wall maintains the lumen may not require a support mandrel 30 to support the wall from collapsing during the bending process but might benefit from a support mandrel for holding the curvature in place or heating the medical device during the process. The forming unit 50 is configured to provide the necessary attributes to the medical device 10 during the bending process so that the curvature is maintained on the medical device 10 when it is removed from the curving apparatus 4. The forming unit 50 may work in conjunction with the bending tool 40 to support the bending process as well as with a support mandrel 30 which may also provide structural support to maintain the curvature. In the case of a medical device 10 made from a malleable material such as aluminum, the forming unit 50 might provide the support for the bending tool 40 to bend the medical device 10 around. In the case of a medical device 10 made from a thermoplastic polymer material, the forming unit 50 might provide heating to the medical device 10 during the bending process followed by cooling to the medical device 10 while it is held in the curvature position by either the bending tool 40 or the support mandrel 30. Creating a curvature on the medical device 10 in two dimensions within the primary base 21 and secondary base 22 is simply a process of either moving the medical device 10 relative to the bending tool 40, or moving the bending tool 40 relative to the medical device 10 along the plane formed by the primary base 21 and secondary base 22. Creating a curvature on the medical device 10 in two and one half dimensions or three dimensions, requires either the medical device 10 or the bending tool 40 to move in a direction that bends the medical device 10 out of plane with the primary base 21. This may be accomplished by having the secondary base 22 move relative to the primary base 21, either by translating or rotating. The barrier 20 may be used with the curving apparatus to ensure sterility of the medical device 10. The medical device 10 would typically start out sterile for the procedure, so the purpose of the barrier 20 is to keep any non-sterile particles, points, lines, surfaces or volumes from coming in contact with the sterile medical device 10. It is also contemplated that the medical device 10 starts out non sterile and that the barrier 20 enables the sterilization process of medical device 10 while providing a barrier to the user of the curving apparatus 4.

Additional characteristics and embodiments of the support mandrel 30 will now be discussed in an effort to better understand the curving apparatus 4. In order to maintain interior or exterior dimensions of a medical device 10, or to assist with maintaining and forming the curvature of the medical device 10, a mandrel 30 may be used. The mandrel 30 can be a solid, liquid, or gas, a force or field such as a magnetic field, electromagnetic radiation, or any combination thereof, internal or external, or a combination of internal and external to the medical device 10.

The mandrel 30 can be a solid piece of material composed of metal, plastic, composite, layers of different materials, ceramic, elastomer, rubber or any other solid. One preferred embodiment is a malleable wire material, such as aluminum, that has been coated with a lubricious coating such as Polytetrafluoroethylene (PTFE). The wire support mandrel 30 will sufficiently support the inner diameter of the medical device 10, and maintain the curvature after it has been curved, thereby allowing the medical device to remain in the completed curvature while it is cooling or otherwise becoming stable, after which the wire support mandrel 30 can be removed.

One embodiment of a solid mandrel 30 would be to use a shape memory alloy (SMA), such as Nitinol and then bend the mandrel 30 to the desired shape prior to sheathing it with the medical device 10. The SMA would be bent to the desired radius and heated to set the shape. When the SMA has cooled it would be straightened. The mandrel 30 can be inserted into the medical device 10. The medical device 10 and mandrel 30 would then be heated, causing the SMA to return to its parent state. The further heating of the medical device 10 and mandrel 30 in order to maintain the bend radius can be performed by any means described in this specification.

The material of the mandrel 30 can be heat conductive allowing the medical device 10 to be molded around the heated mandrel 30. If a solid mandrel 30 is used, any material such as polymers, metal, plastic, rubber or any material currently in use or that will be in the future that allows for a solid piece of material to maintain the inner dimension of a tube-like structure could be utilized. In the same way the mandrel can be heated to mold the medical device it can also be cooled after bending in order to rapidly cool the medical device. This could be accomplished by connecting the hot mandrel to a cold reservoir to conduct heat into.

Inner dimensions of the medical device 10 can also be maintained by a segmented section or ball chain type configuration connected with a hinged or flexible material. The sections or balls can be of varying sizes to fit various medical device 10 diameters. The sections can be cylindrical with cylindrical flexible joints in order to maintain a constant diameter. The mandrel 30 may be flexible at the joints, and so may have variable flexibility depending on the flexibility of the joints and the lengths of the adjoining sections. With a ball section configuration, the gaps between sections/balls define a length along the mandrel 30 where deformation may occur. This may be addressed by the fact that the bending tool 40 will touch the exterior of the medical device 10 in a way that will only touch at the highest point of consecutive segments/balls. This will ensure that no deformation of the inner dimension occurs.

A mandrel 30 may also consist of a liquid inserted directly into the medical device 10, or a combination of a thin solid membrane with a liquid core. The liquid can remain a liquid or be altered by a change in temperature, applied field, or other method that causes it to become a solid permanently or temporarily. An increase in temperature of the liquid can also serve as the heat necessary to mold the medical device. The interior of the medical device 10 may have a coating with a material that prevents the adhesion of the liquid to the interior surface. As in the case of a liquid cast stent type device, the material would be injected into the interior of the tube, solidified by cooling, heating, applying a field of electromagnetic radiation or by a chemical reaction and once the bending is complete, converted back to a liquid to allow the liquid to be released from the medical device 10. If it becomes a permanent solid completely filling the interior, then it will need to be removed once the bending of the medical device 10 is complete.

One example is the interior of the medical device 10 injected with a cooled liquid and sealed at both ends. As the medical device 10 is heated by the forming unit 50 during bending, the liquid reacts to the heat and becomes a solid providing the interior of the medical device 10 the stability necessary during bending. Upon cooling, the solid returns to its liquid state and can be drained from the medical device 10.

Another example is where a ferrofluid is injected into the medical device 10, capping on both ends to form the support mandrel 30. Caps could be similar to stoppers on injectable bottles or any other method that seals the medical device 10 with liquid inside during the bending. One or both of the stoppers/seals must be easily removed for the draining of the liquid. Either the ferrofluid will be injected prior to inserting the medical device into the curving apparatus 4 or after insertion, and bent by any of the methods described in this specification. While the medical device is in the bent position caused by the bending tool 40, an electromagnetic field is applied causing the ferrofluid to solidify in that shape. Heat is then applied to the bent medical device 10 by the forming unit 50 to cause the medical device 10 to be more malleable and thus bent to the desired radius.

Another embodiment of the support mandrel 30 is to have a cylindrical ferrofluid reservoir. This is formed by a thin tubular membrane filled with a ferrofluid. This tubular reservoir would be inserted into the medical device 10 prior to bending. The reservoir can be set to the inner diameter of the medical device 10 or pressurized to expand to the inner diameter. The reservoir can be a constant diameter or consist of many smaller cylinders of balls joined together with a smaller diameter to facilitate bending. The ferrofluid mandrel 30 can be configured to either conform to the medical device 10 shape being created by external forces, or create the medical device 10 curvature based on an applied electromagnetic field from forming unit 50. Due to the nature of ferrofluids, the electromagnetic pulse interacts with the magnetic material causing it to conform to a given shape. As long as the pulse is rapid and consistent, the force exerted on the ferrofluid will keep it in that desired shape. In a gradient field the whole fluid responds as a homogeneous magnetic liquid that moves to the region of highest flux. This means that ferrofluids can be precisely positioned and controlled by an external magnetic field. The forces holding the magnetic fluid in place are proportional to the gradient of the external field and the magnetization value of the fluid. This means that the retention force of a ferrofluid can be adjusted by changing either the magnetization of the fluid or the magnetic field in the region. The thermal stability of a ferrofluid is related to particle density. The particles appear to behave like a catalyst and produce free radicals, which lead to cross linking of molecular chains and eventual congealing of the fluid. Catalytic activity is higher at elevated temperatures and, therefore, ferrofluids congeal more rapidly at these temperatures.

Once the bending of the medical device 10 is complete and the medical device 10 has sufficiently set the bend, the electromagnetic pulse is turned off and the ferrofluid returns to its liquid state. The reservoir tube can then be removed and reused for the next procedure.

The support mandrel 30 can also be gas, i.e., nitrogen, oxygen, or any of the noble gases or any other gas that remains a gas at room temperature and does not present any hazard to personnel or patient. One embodiment of the gas support mandrel 30 provides pressurized gas to the exterior of the medical device 10 to keep it from deforming or ovalizing at points adjacent to the curving. Another embodiment provides pressurized gas to the interior of the medical device 10 in order to maintain a circular cross section during the bending process. Once the medical device 10 curvature is complete, cooling will set the curve. The support mandrel 30 may then be removed, or in the use of gas, released.

Another embodiment of the curving apparatus 4 is to bend without a support mandrel 30 by incrementally heating the medical device with the forming unit 50 in such a narrow band that the adjacent structures on either side of the heated region maintain the cross sectional integrity of the medical device 10. In this embodiment, the forming unit 50 may generate heat on the medical device via a laser so as to have a very controlled narrow heated region.

Additional characteristics and embodiments of the bending tool 40 will now be discussed in an effort to better understand the curving apparatus 4. The bending tool 40 may be comprised of a series of cylinders in a concentric or non-concentric configuration. The cylinders may be configured with different grooves increasing in radius top to bottom. The grooves on each cylinder may accommodate different medical device 10 radii. The selected cylinder may rise depending on the required radius called for by the controller 23 of the medical device 10 and the specified curvature. The curve cylinder is selected based on curve radius and the height the curve cylinder rises depending on the inputted radius of the medical device 10. The medical device 10 may advance toward the bending tool 40 cylinders by means of the grasping fixture 60. The cylinder diameter is programmed to match the curve radius so that the cylinder is in position when the medical device 10 advances. The opposing force is provided by a rotating guide cylinder, with the same radii grooves as that found on the curve cylinder that rolls along the exterior edge of the medical device 10 enclosing it between the grooved edges of the curve cylinder and the rotating guide cylinder. Since the inputted radius of the medical device 10 determines the groove chosen on the curve cylinder, a touch sensor may direct the guide cylinder toward the curve cylinder and stop when the edges of the grooves on both cylinders meet. When the rotating guide cylinder rolls along the medical device 10, it is also rolling along the curve determined by the curve cylinder. To support as many different radii as possible multiple curve cylinders and guide cylinders can be used. They can be manually interchanged or the curve cylinders can cycle through beneath the secondary base 22.

A similar bending tool could be utilized that is a flexible sheet of material bent around in a U shape in compression. Pulling ends of the sheet together would decrease the radius while letting the ends move apart would increase the radius.

Due to contact with the medical device 10 the bending tool 40 must stay sterile in some way. One way this could be accomplished would be to have sterile one use bending tools 40 that will snap in before each use of the curving apparatus 4. A sterile flexible barrier or any other method of sterilization specified later in the text could also be utilized.

The curve cylinder can be a source of heat by using coils or being made of a heat conductive metal that can be heated so that when the medical device 10 comes around the side against the cylinder it will be heated. The opposing guide cylinder can also be a source of heat. The movement of the roller around the tower for the bend can be slowed to allow the heat to penetrate the medical device 10.

One of the inherent factors in imparting curvature by applying force with a bending tool 40 to a medical device 10 is some level of hysteresis or spring back of the curvature which results in the curvature being less than desired, especially if the curve is being made incrementally. Each incremental bend, if only slightly less than the desired curvature, will "add" up over time and result in a drastically insufficient curve shape at the end. Each hysteresis or spring back step during the curving process can be addressed in multiple ways. 1) An algorithm to overcompensate the curve based on experimentation or on a relationship between the curve radius and the size of the medical device, material, etc., (it is also contemplated that the controller 23 will have the ability to use artificial intelligence or other logic to learn about the curving process so as to be able to take preventive steps to eliminate hysteresis in the curving process by recording the hysteresis on the curve database 2 based on the specific medical device 10 being used). 2) A force sensor (or other type of proximity sensor) embodied on the bending tool 40 can sense when the bending tool 40 is in contact with the medical device 10 and use an algorithm to repeatedly bend and release, increment the bend (overbend), and release until the sensor detects that the bending tool 40 is no longer in contact with the medical device 10 at the proper curvature. 3) A membrane or bladder embodied on the bending arm in fluid communication with a pressure sensor that operates in a similar fashion to that described in 2) with repeated bending and releasing until the sensor detects that the curvature is appropriately formed, and 4) An optical device or sensor in view of the bending position to ensure that the bending or overbending is repeated until the curvature is appropriately formed.

Additional characteristics and embodiments of the grasping fixture 60 will now be discussed in an effort to better explain the curving apparatus 4. One embodiment of the grasping fixture 60 is a device for gripping the medical device 10 as it moves toward the bending tool 40. This clamping device will grasp and hold the medical device 10 and pull or push it incrementally. Any device currently available or any new device that may become available at a later date can provide clamping. This grasping fixture 60 would have moving sides that can be programmed to converge upon the medical device 10. The extent to which these opposing sides converge will be programmed based on the diameter of the medical device 10, a sensor system, or any other mechanism to provide grasping parameters. Alternatively the grasping fixture 60 can have force or pressure sensors in order to keep from deforming the medical device 10 in a location that the mandrel 30 does not reach.

Another embodiment for the grasping fixture 60 is to grasp the medical device 10 and slide forward on a rail pushing or pulling the medical device 10 with it in increments determined by the programmed radius. The rail will be located beneath or above the bending platform and will work by pushing, pulling or sliding along a linear actuator.

Another embodiment of the grasping fixture 60 is to use roller towers. Each tower would have another tower opposite to provide the opposing force while also enclosing the medical device 10. Each tower would have a vertical series of different diameter grooves each with a lining to provide a frictional force. This force would propel the medical device 10 to advance. The tower could be raised or lowered depending on the radius of the medical device 10 required. Any subsequent rollers would need to be this tower style in order to accommodate the advancement of the medical device 10. The tower will be lowered or raised depending on the diameter of the medical device 10 which will either be inputted by means of the controller 23 or when the medical device 10 is placed, a sensor will determine the diameter and provide the necessary adjustments of the tower.

Another embodiment of the grasping fixture 60 is the use of SCARA (selective compliant assembly robot arm). The SCARA can be on a rail attached to the table, suspended from above, pulling from the distal end, pushing from the proximal end, or any other location that advances the medical device 10. The SCARA will grip the medical device 10 and slide it forward, returning to grip again and slide. The SCARA may also be attached to a linear stage providing the forward motion necessary to advance the medical device 10. The controller 23 will be programmed to have the SCARA move incrementally depending on the position of the bending tool 40. The medical device 10 may be held by the grasping fixture 60 in any manner including friction grippers, rollers, collet, vacuum, releasable adhesive, or any other means now known or discovered in the future that allows the medical device 10 to be gripped, moved, and released.

Another embodiment of the grasping fixture 60 for advancing the medical device 10 would be a retractable mechanism at the distal end that would pull the medical device 10 incrementally through the machine by way of a pulley system. This pulley system would allow for any back and forth motion necessary during the bending of the medical device 10.

Additional characteristics and embodiments of the forming unit 50 will now be discussed in an effort to better understand the curving apparatus 4. One method of maintaining curvature on the medical device 10 is with the application of heat by the forming unit 50. There are numerous ways to heat a medical device 10 including but not limited to conduction, convection, radiance, laser, electromagnetic radiation, microwave, induction, electric current, friction, chemical, or heating strip. One embodiment of the curving apparatus 4 is that while the medical device 10 is advancing through the bending tool 40, it is heated at a point before, during or after being gripped and prior to being bent. Another embodiment of the use of convection heat is a forced hot-air source such as a heat gun. The heat gun would be mounted in such a way as to direct the heat toward the area of the medical device 10 to be bent by the bending tool 40. Further discussion of convection heating can be found in FIGS. 12 and 13.

The forming unit 50 may also be configured to add or remove material to create the curvature on the medical device 10. As with additive manufacturing, such as a three dimensional printer, material is either bonded together, melted, sintered, or otherwise connected at very small increments to form the desired curvature. Alternatively, with subtractive manufacturing, the curving apparatus 4 can remove material to create the desired curvature on a medical device 10. The forming unit 50 can also provide heat to the medical device 10.

Figure 62:
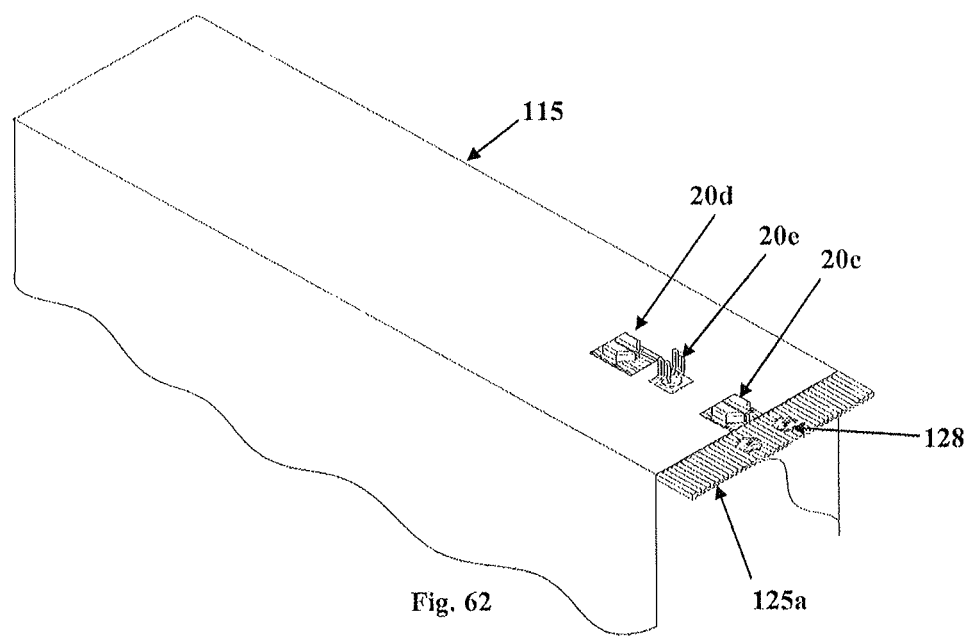
FIG. 62 is a pictorial view embodiment of a sterile fenestrated drape used to cover the curving apparatus.

Additional characteristics and embodiments of the barrier 20 will now be discussed in an effort to better understand the curving apparatus 4. One embodiment of the present invention for the barrier 20 is a sterile drape that will engulf the entire curving apparatus 4, and serve as a barrier to prevent infectious agents from passing. For the purposes of this disclosure, infectious agent(s) will mean any particle, particulate, or any single, multicell, or acellular organism or micro-organism, including but not limited to bacteria, fungi, arcaea, spores, protozoa, protists, algae, plants, animals, plankton, planarian, helminthes, and infectious biological agents such as viruses, virions, viroids, plasmids, prions, or other autonomous or semi-autonomously replicating genome that is alone, or in combination with other infectious agents, airborne, in a gas, in or on a fluid, attached to an object such as a surgical glove, instrument, medical device, fitting, or any other article that is able to cause infection or disease to a living body such as an animal or human. The drape (as seen in FIG. 62) can cover the primary base 21 and secondary base 22 and extend down to the floor to prevent infectious agents from contacting the medical device 10. Another characteristic of the barrier 20 is the ability to isolate the non-sterile moving features of the bending tool 40, grasping fixture 60, forming unit 50, and secondary base 22 from the sterile medical device 10. This requires the barrier 20 to incorporate a flexible, extendible, or elastic structure to cover these moving components. This portion of the sterile barrier 20 can be made of a flexible rubber, silicone rubber, polyurethane, or any other material currently in use or will be used in the future that offers the combination of flexibility, heat conductivity, malleability, and/or any other characteristics necessary for the functioning of the unit. The barrier 20 can be reusable or disposable material. The more flexible portion of the barrier 20 is designed to tightly contour the entire area where the medical device 10 bending occurs. The barrier 20 may molded or formed to closely fit the bending tool 40, grasping fixture 60, and forming unit 50.

Other methods of sterilizing the medical device in contact with possible non-sterile feature of the curving apparatus are also contemplated. Sterilization by chemicals, electromagnetic radiation, heat, and other sterilization means can be performed before, during, or following the curving process. Further embodiments for sterilization can be seen in FIGS. 62 through 63 and FIGS. 74 through 76.

Figure 9:
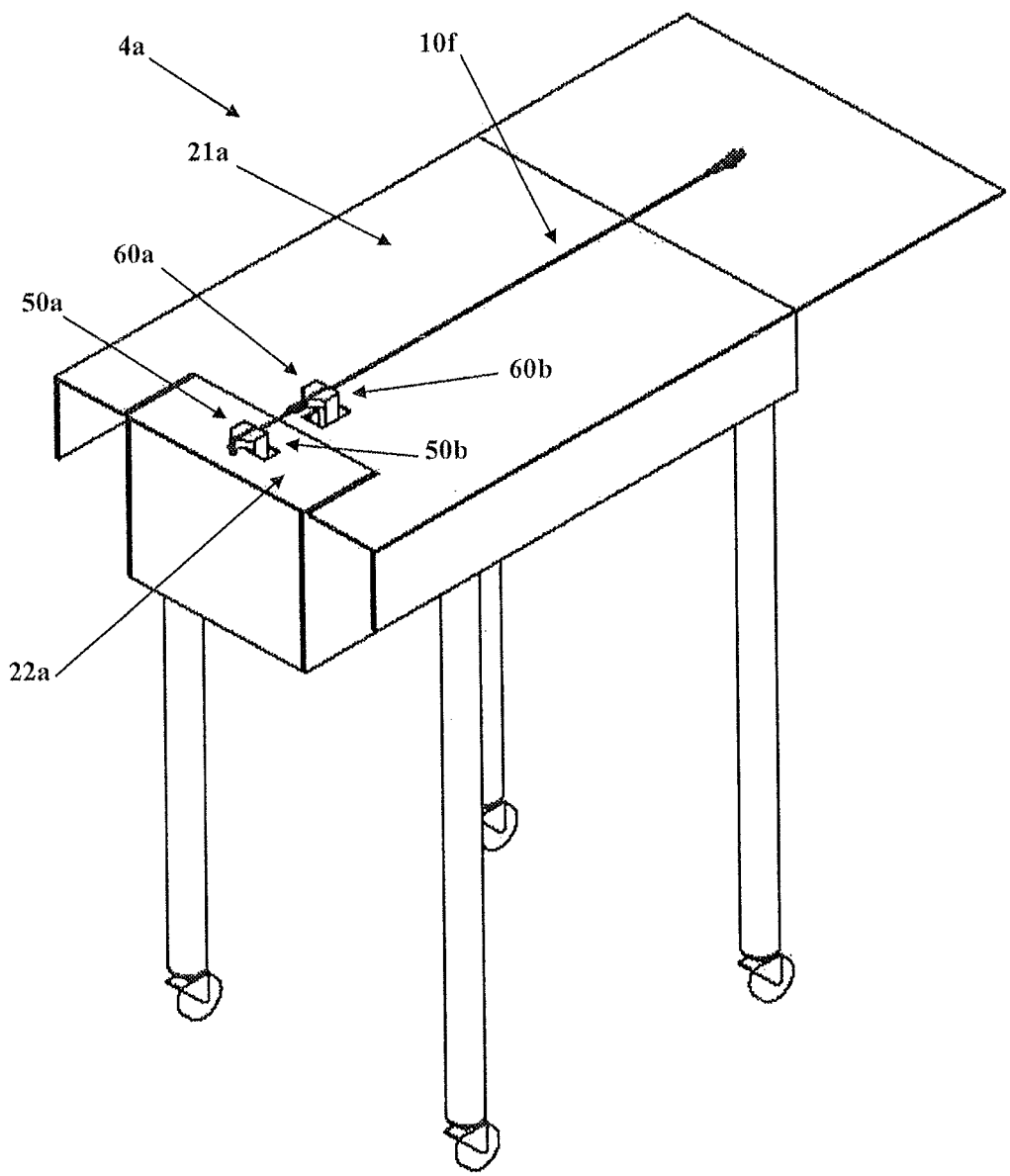
FIG. 9 is a pictorial perspective view of a curving apparatus embodiment.

FIG. 9 is a pictorial view of a curving apparatus 4a embodiment excluding a barrier 20. It has a primary base 21a, a secondary base 22a which is configured to rotate the forming units 50a and 50b out of plane with respect to the primary base 21a. The medical device 10f is held by the grasping fixtures 60a and 60b which are configured to grasp the medical device 10f and advance the medical device 10f towards the forming units 50a and 50b.

Alternatively, to eliminate medical device movement and the potential for unwanted device rotation and slippage, the medical device 10f could be firmly held at the proximal end, and the grasping fixtures near the distal end could be programmed to move backward along the medical device instead of advancing the device. The grasping fixtures would release the device, move toward the proximal end a specified amount, and grasp the medical device once again. This movement would leave a small increment of the medical device available to be bent by the forming unit, which would follow the distal grasping fixture back along the device.

Figure 9A:
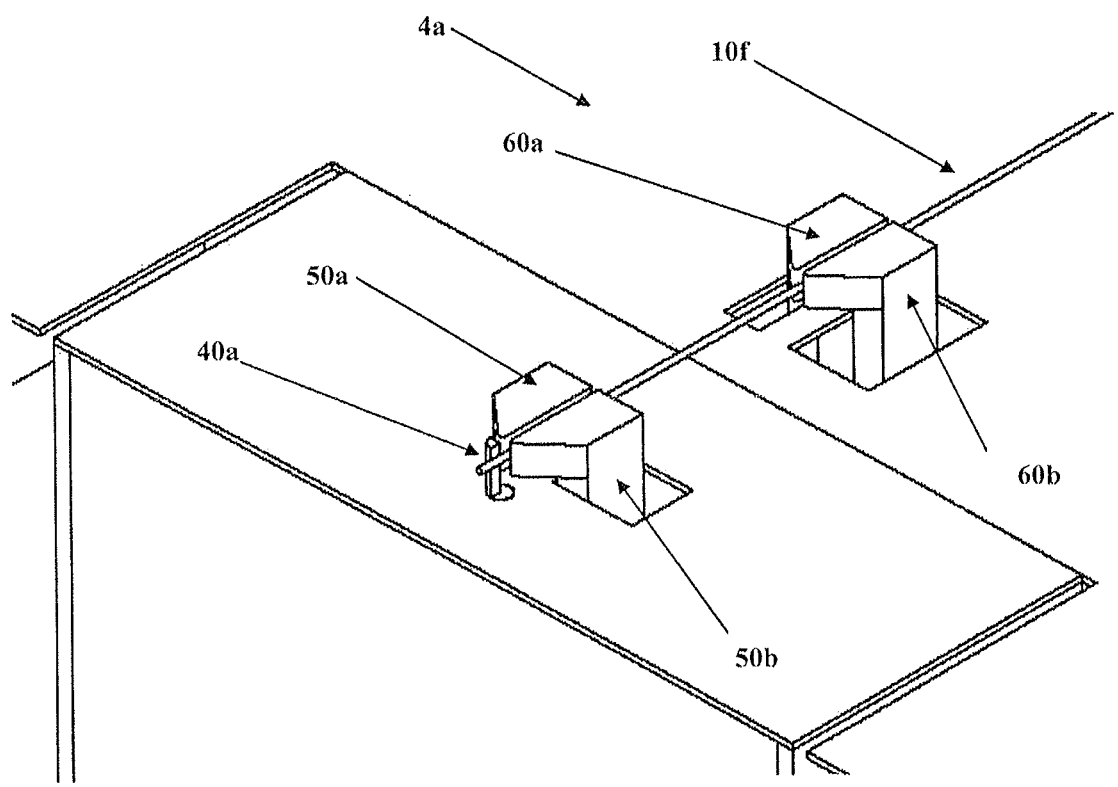
FIG. 9a is an enlarged pictorial perspective view of the curving apparatus embodiment of FIG. 9.
Figure 9B:
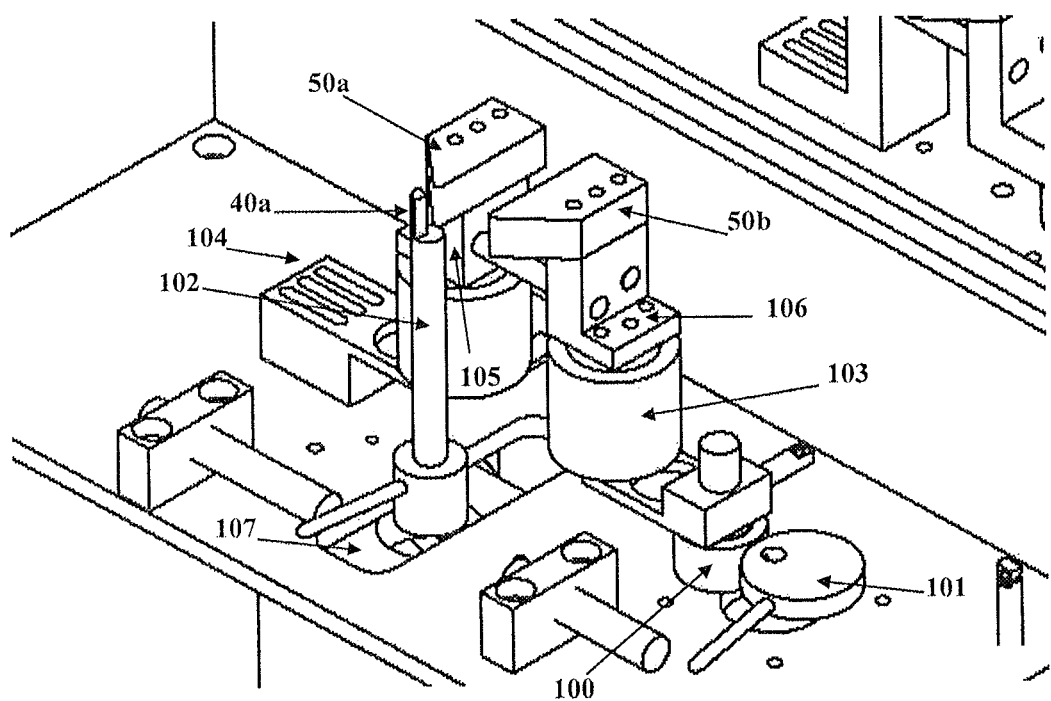
FIG. 9b is an enlarged pictorial perspective view of the curving apparatus embodiment of FIG. 9.
Figure 9C:
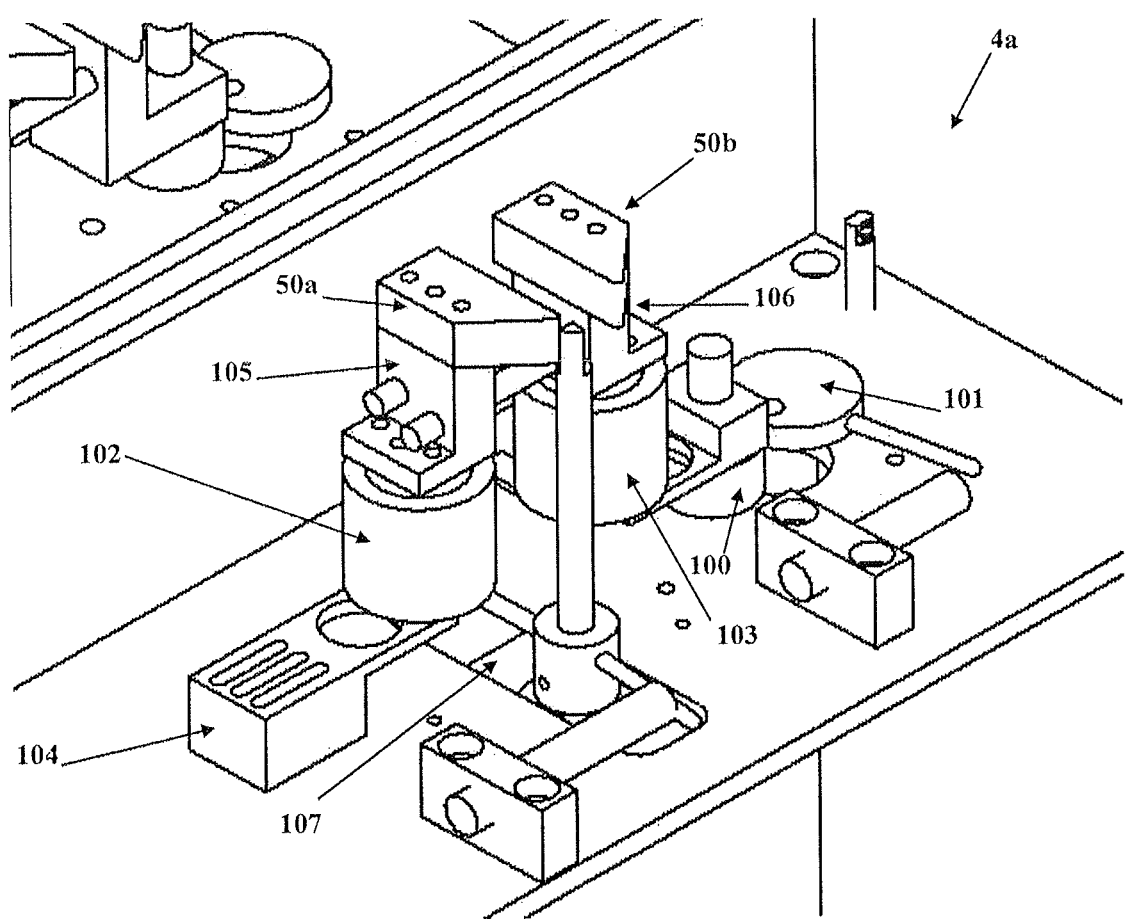
FIG. 9c is an enlarged pictorial perspective view of the curving apparatus embodiment of FIG. 9.
Figure 9D:
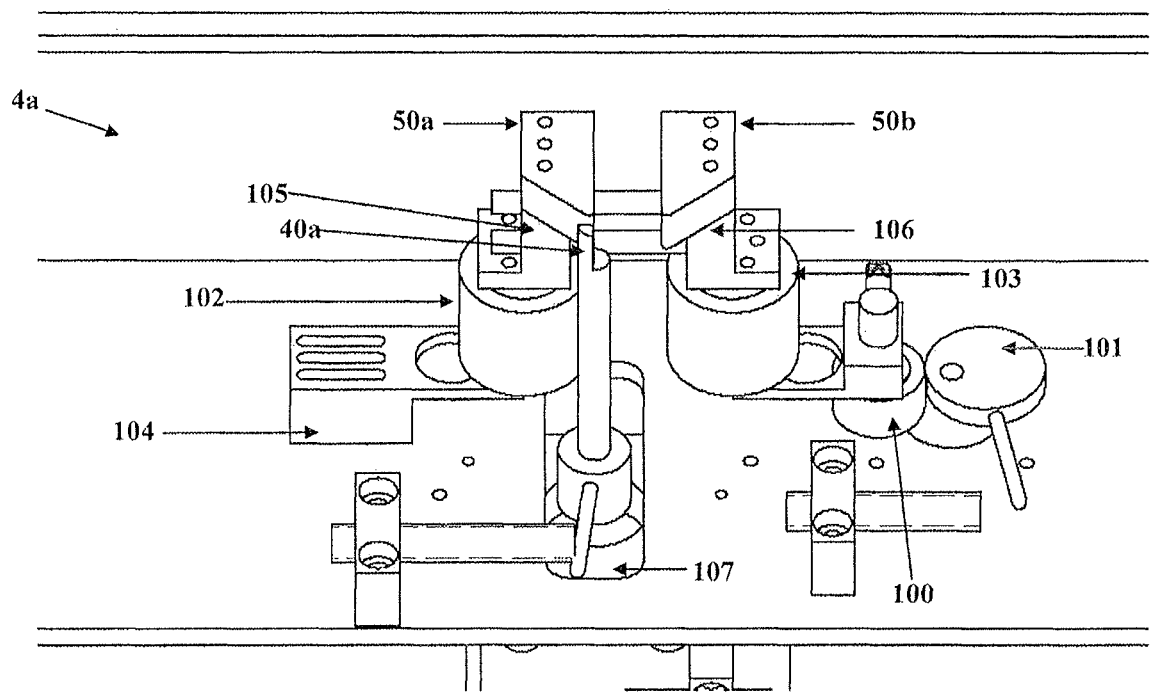
FIG. 9d is an enlarged pictorial view of the curving apparatus embodiment of FIG. 9.
Figure 9E:
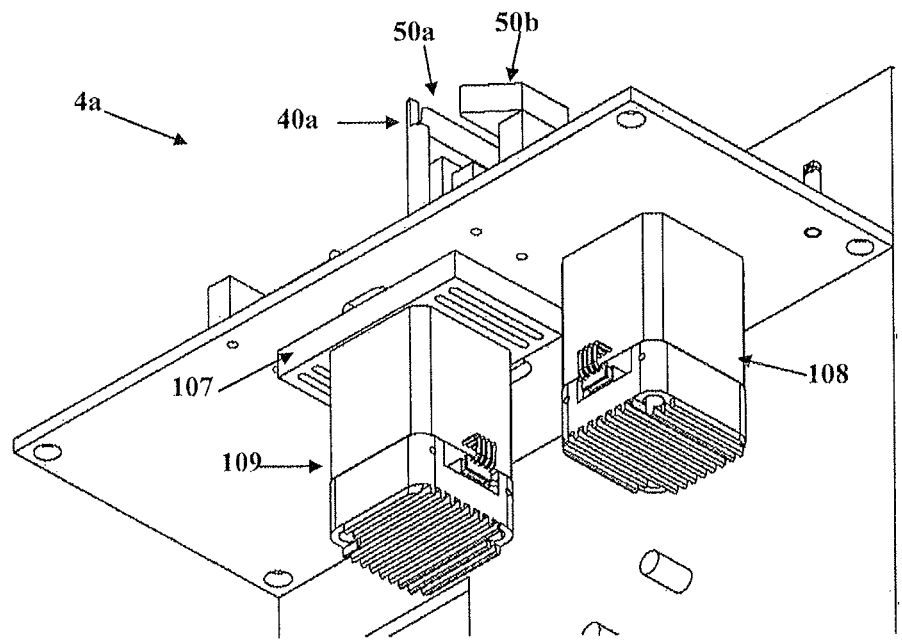
FIG. 9e is an enlarged pictorial view of the curving apparatus embodiment of FIG. 9.
Figure 9F:
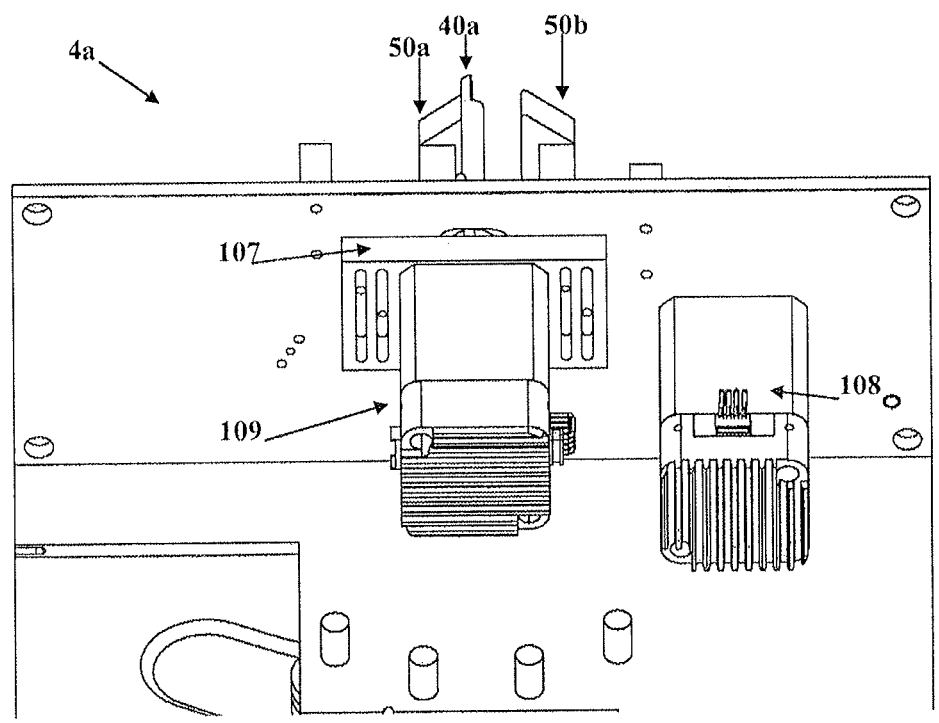
FIG. 9f is an enlarged pictorial view of the curving apparatus embodiment of FIG. 9.

FIG. 9a is an enlarged pictorial view of the bending features of the curving apparatus 4a of FIG. 9 again showing the medical device 10f and the grasping fixtures 60a and 60b that can close together to grip the medical device 10f and advance the device into the gap between forming units 50a and 50b. The forming units are in conduction communication with heaters 103 and 105 (FIG. 9b) which allow the medical device to be preheated when they close together onto the medical device 10f for a predetermined dwell time sufficient to heat the medical device 10f to a temperature close to its melting point. The heated forming units 50a and 50b may then separate and the grasping fixtures 60a and 60b may advance the medical device 10f past the forming units 50a and 50b so that the medical device 10f is adjacent to the bending tool 40a. At this point, the heated forming units 50a and 50b can close onto the medical device 10f to provide heating, and the bending tool 40a can rotate to apply a force to the medical device 10f for a precise amount of rotation to form a curvature on the medical device 10f. This process of the forming units 50a and 50b closing to heat and hold the medical device 10f, the grasping fixtures 60a and 60b opening and returning to their original position, the grasping fixtures 60a and 60b closing to grip the medical device 10f, the forming units 50a and 50b opening to release the medical device 10f, the grasping fixtures 60a and 60b advancing the medical device 10f past the forming units 50a and 50b so that the medical device 10f is advanced further past the bending tool 40a, the heated forming units 50a and 50b closing to hold and heat the medical device 10f, and the bending tool 40a rotating to apply a force to the medical device 10f for a precise amount of rotation to form a curvature on the medical device 10f, is repeated over and over until the programmed curvature is applied to the medical device 10f.

It should be understood that the amount of incremental movement, dwell, heat temperature, and bending rotation is completely programmable by a controller 23 (FIG. 8). A support mandrel 30 may or may not be used to support the medical device 10f. The heating process can be generated by any means disclosed earlier including induction, where the support mandrel 30 could be of an inductive material and the forming units 50a and 50b could induce a current within the mandrel to cause the medical device 10f to heat from the inside out. This would prevent any deformation to the outer surface of the medical device 10f by the bending tool 40a. Further details of induction heating can be found in FIGS. 25 through 27.

Alternatively with heat being applied by the forming units 50a and 50b as shown in FIG. 9a, the interaction of the bending tool 40a and the forming units 50a and 50b must be subtle, and the amount of rotation by the bending tool 40a limited to avoid damage to the outer surface of the medical device 10f. It is also possible with various heating sources to turn the heating on and off in a manner where the medical device 10f could be bent cold, then heated and cooled to again prevent any damage to the outer surface. It is also contemplated to bend the medical device 10f without applying force to the outer surface, but rather through the support mandrel 30 as disclosed in FIG. 8 discussion above.

The secondary base 22a in FIG. 9 enables the curving apparatus 4a to make a completely three dimensional shape. The secondary base 22a can rotate along the centerline access of the medical device 10f. The forming units 50a and 50b along with the bending tool 40a are mounted to the secondary base 22a. Thus, when the medical device 10f is held by the forming units 50a and 50b but not by the grasping fixtures 60a and 60b, and the secondary base 22a rotates, the medical device 10*f* rotates with the angular rotation of the secondary base 22*a*. The medical device 10*f* may then be held by the grasping fixtures 60*a* and 60*b* and released by the forming units 50*a* and 50*b*, so when the secondary base 22*a* returns to its initial orientation in plane with the primary base 21*a*, the medical device remains at the angled orientation created by the secondary base 22*a* rotation. This can be repeated as necessary to allow the medical device 10*f* to be oriented and curvature applied at any rotational angle along the length of the medical device 10*f*.

Alternatively the secondary base 22*a* can remain fixed while a smaller mechanism not shown in the figures can rotate the device eliminating the need to rotate the entire secondary base 22*a*. To accomplish this, the medical device 10*f* would be in a feature fixed to the primary base 21*a* (FIG. 9) which cyclically rotated the medical device 10*f* by applying torque to any part of the medical device 10*f*. Both the grasping fixtures 60*a* and 60*b* and the forming units 50*a* and 50*b* would release the medical device 10*f* to allow rotation without a twisting deformation.

FIG. 9*b* through FIG. 9*h* detail the specific mechanical and electromechanical components of the embodiment pictured in FIGS. 9 and 9*a*. It can be understood by one skilled in the art of mechanics or machine design that motors coupled to cams in communication with cam followers, and ground pins sliding in linear bearings between the linear moving parts can provide the necessary motion to accomplish the steps outlined above. Linear actuators can push and pull lever arms to cause rotation. This rotation can be applied to the bending tool 40*a* to cause rotation or the forming units 50*a* and 50*b* to cause linear motion. All motors will be connected to the curve user interface 3 (FIG. 1) which will directly or indirectly control the motors in different increments required for each specific curve. The motors can also be used to provide heating to the forming grips 50*a* and 50*b* in the forms of direct heating of the medical device 10*f* or indirect heating to the mandrel 30(FIG. 8) by any of the ways described above.

Figure 10:
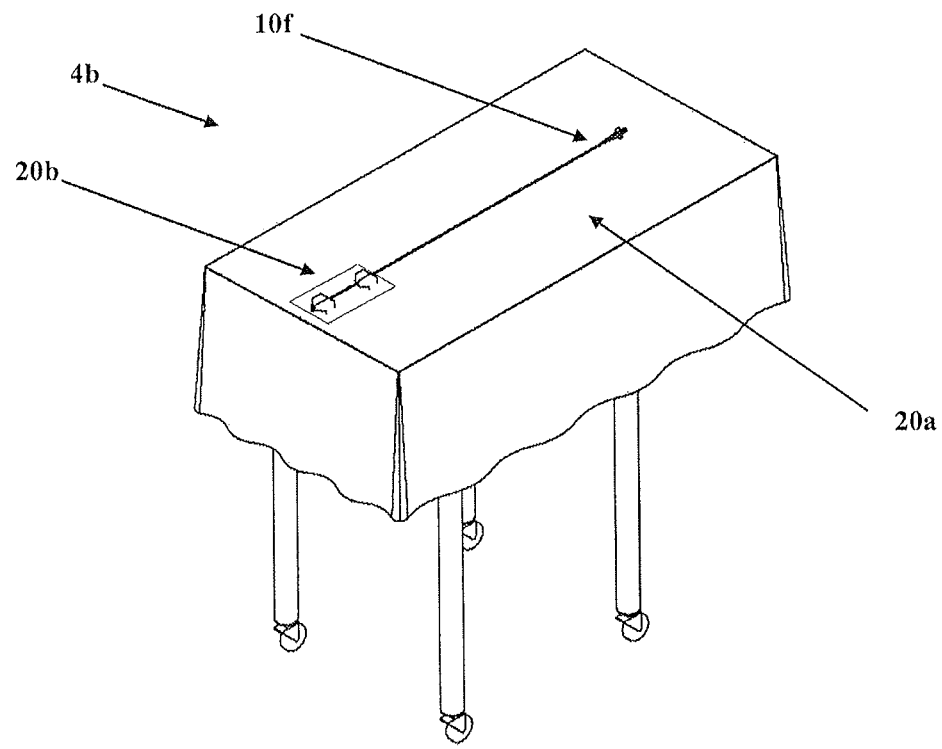
FIG. 10 is a pictorial perspective view of a curving apparatus embodiment with a sterile drape.

FIG. 10 is a pictorial view of a curving apparatus 4*b* embodiment which is equivalent to the mechanical embodiment of FIG. 9 with the addition of a barrier 20*a* and flexible barrier 20*b*. Barrier 20*a* and 20*b* contour the curving apparatus 4*b* are sterile and act as a sterile barrier between the mechanical embodiment of FIG. 9 and the sterile medical device 10*f*.

Figure 10A:
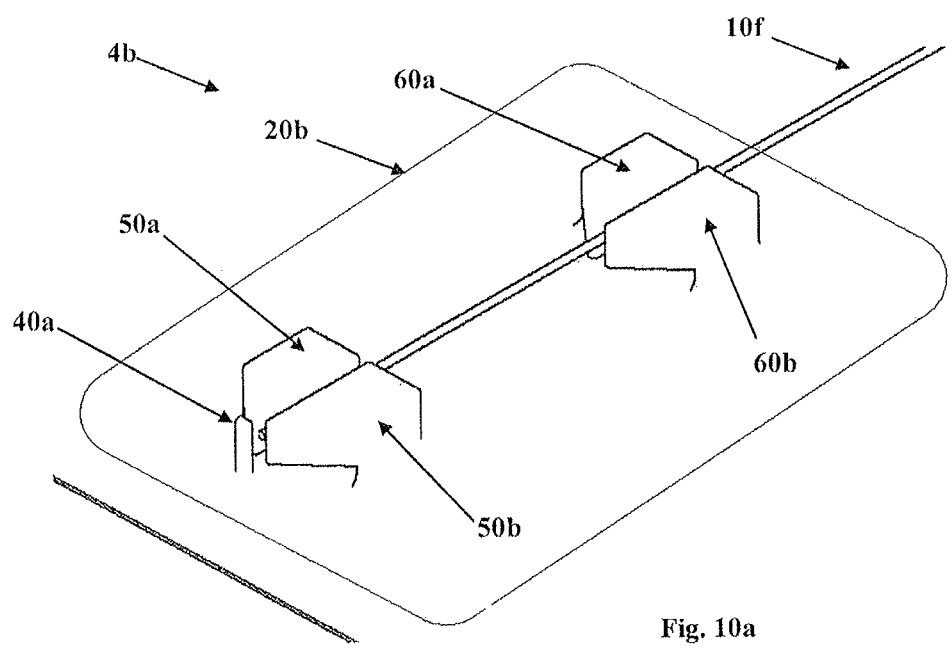
FIG. 10a is an enlarged pictorial view of the curving apparatus embodiment of FIG. 10.

FIG. 10*a* is an enlarged pictorial view of the bending features of the curving apparatus 4*b* of FIG. 10 and shows how the flexible barrier 20*b* may be formed to cover and contour the grasping fixtures 60*a* and 60*b*, the forming units 50*a* and 50*b*, and the bending tool 40*a*. As an elastic, extendable, or flexible sterile barrier, the barrier 20*b* will allow these components to provide the necessary motion described in FIG. 9*a* above, while ensuring the medical device 10*f* remains sterile. Furthermore, the barrier 20*b* to configured to conduct heat from the forming units 50*a* and 50*b* to the medical device 10*f* and provide frictional gripping properties between the forming units 50*a* and 50*b* and the medical device 10*f*, as well as between the grasping fixtures 60*a* and 60*b* and the medical device 10*f*. The flexible barrier 20*b* does not have to be one complete barrier. It can be broken up into small sections that fit over each of the mechanical fixtures. The barrier 20*a* would overlap with the flexible barriers 20*b* keeping the device sterile.

FIG. 11 is a pictorial view of a primary base 21*a* with linear grasping fixtures 60*c* and 60*d* used to grip the medical device 10. There can be any number necessary of left and right paired linear grasping fixtures 60*c* and 60*d* to grasp, move, and release the medical device 10.

FIGS. 11*a* through 11*c* are pictorial views of the primary base embodiment of FIG. 11 wherein the linear grasping fixtures 60*c* and 60*d* are shown to move. In FIG. 11*a* the back pair of linear grasping fixtures 60*c* and 60*d* closes upon the medical device 10 to hold it. FIG. 11*b* shows the back pair of linear grasping fixtures slides forward to advance the medical device 10 along the primary base 21*a*. FIG. 11*c* illustrates the closure of the front pair of linear grasping fixtures to hold the medical device 10 steady.

FIG. 12 is an enlarged pictorial view of the primary base 21*c* with horizontal roller supports 60*e* used to hold and advance the medical device 10 and included mandrel 30 if used. The horizontal rollers 60*e* could have a friction material lining the exterior surfaces that would come into contact with the medical device 10. The horizontal rollers 60*e* would be a mechanism to advance the medical device 10 and a guide to keep the medical device 10 from moving up and down. An advancing roller on each side of the medical device 10 this would ensure the stability of the medical device 10 while traveling through the machine. Rollers can be in any position as long as the net force on the medical device 10 is zero. The rollers can be stationary with advancement of the medical device 10 provided by another embodiment of advancement technology or the rollers can move in conjunction with a linear actuator. The rollers can also serve as a heat source.

Figure 13:
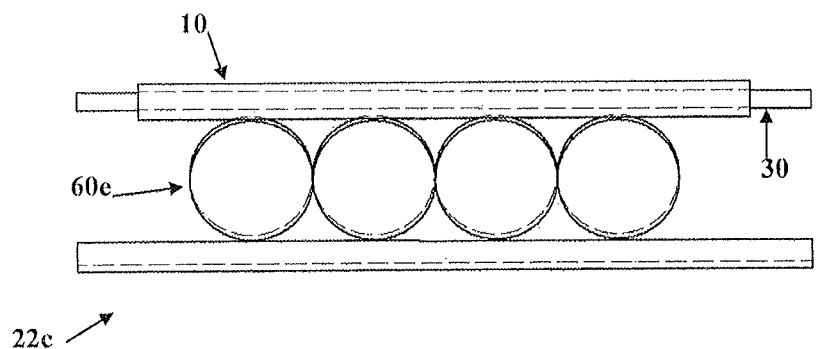
FIG. 13 is an enlarged side view illustration of the primary base embodiment of FIG. 11 with horizontal gripper supports.

FIG. 13 is an enlarged side view illustration of the primary base 21*c* and horizontal roller supports described in FIG. 12. The rollers 60*e* could be positioned in different increments and could have different sizes than shown. The rollers 60*e* could also be removed which would allow for sterile covers to be placed over them. The sterile covers would be flexible and create enough friction to properly grip the medical device 10 for movement.

Figure 14:
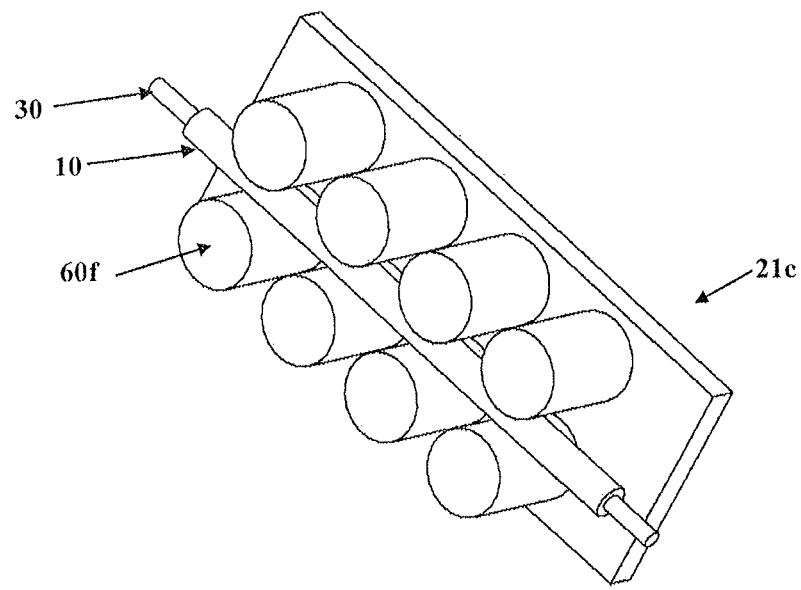
FIG. 14 is an enlarged isometric view of the primary base embodiment of FIG. 11 with vertical gripper supports.

FIG. 14 is an enlarged isometric view illustration of the primary base 21*c* with vertical roller supports 60*f* used to hold and advance the medical device 10 and optionally included mandrel 30. The vertical roller supports 60*f* could have a frictional lining that comes into contact with the medical device 10 or be shaped to close around the medical device 10 to be used for grasping, holding, and advancing. The vertical roller supports 60*f* could advance the medical device 10 by either rotating or sliding and could also serve as a heat source.

The horizontal rollers 60*f* are in contact with the medical device 10 throughout the curving process. There are many possible means that could keep the medical device sterile through this process. The horizontal rollers 60 could snap into the primary base 21*c*. The snappable horizontal rollers 60 would be presterilized and inserted right before each use of the curving apparatus 4 (FIG. 1).

One or more rollers 60*f* may be used to advance the medical device 10. The rollers 60*f* may be configured as any circular or partially circular object that can indirectly or directly engage the medical device 10. The rollers 60*f* may have a surface that is grooved or otherwise shaped to increase the engagement area on the medical device 10, or have a soft surface that conforms to the outer shape of the medical device 10.

Figure 15:
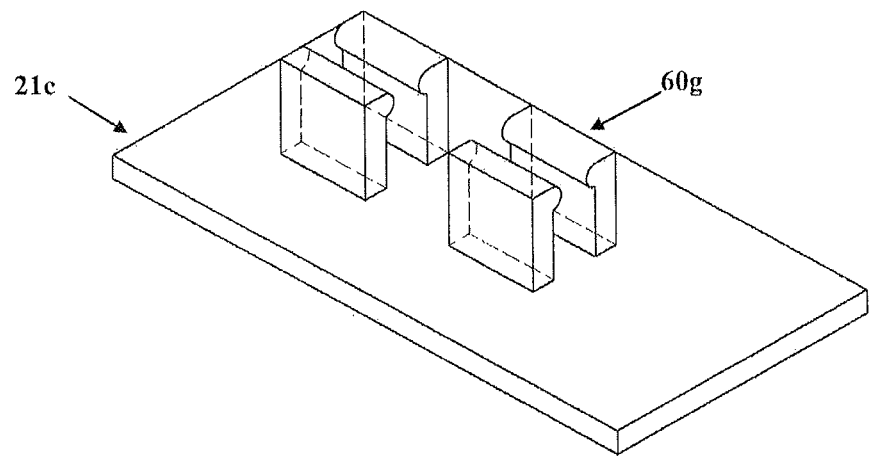
FIG. 15 is an enlarged isometric view of the primary base embodiment of FIG. 11 with inflatable gripper supports.
Figure 16:
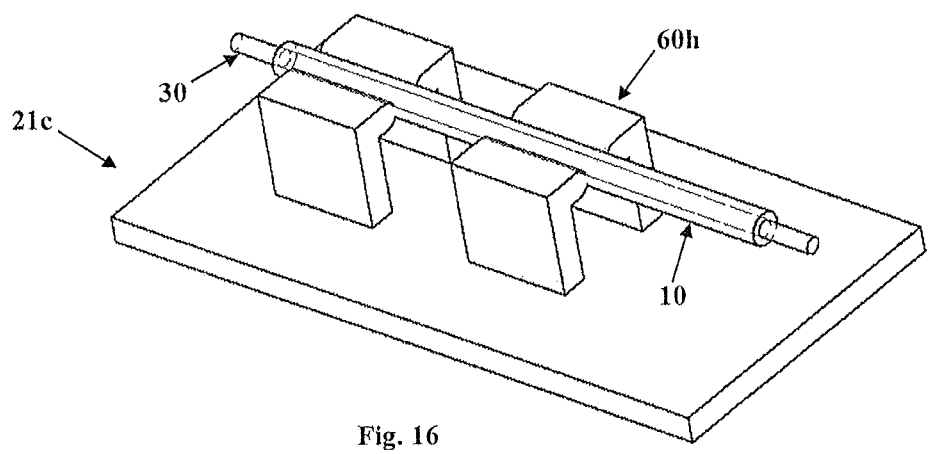
FIG. 16 is an enlarged isometric view of the primary base embodiment of FIG. 11 with inflated grippers holding the medical device.

FIGS. 15 and 16 comprise another embodiment of the grasping fixture 60*g* (FIG. 15) and 60*h* (FIG. 16) involving a set of tubular structures with an inner lining of inflatable rubber. Once the medical device 10 and optionally included mandrel 30 are inserted, the lining inflates and traps the medical device 10 to hold it firmly in place. A set of at least two tubular structures would be utilized with at least one near the proximal end and the other at the distal end of the medical device 10. The proximal tube would inflate, grasping the medical device 10 and be mounted on a rail type system so that it could move forward and advance the medical device 10. After advancing, the medical device 10 will be gripped by the distal tube for greater stability. Sterile flexible covers could be placed over the tubular structures. These covers would overlap with the barrier 20*b* (FIG. 10*a*) to keep the curving apparatus 4 (FIG. 1) sterile.

The present invention is not limited to the specific embodiments described above in relation to the grasping fixture, as someone skilled in the art could readily apply alternative methods such as magnetic grasping, vacuum, pressure, gel or other formable grippers, etc.

The following embodiments examine various methods of preparing the medical device 10 to be bent.

Figure 17:
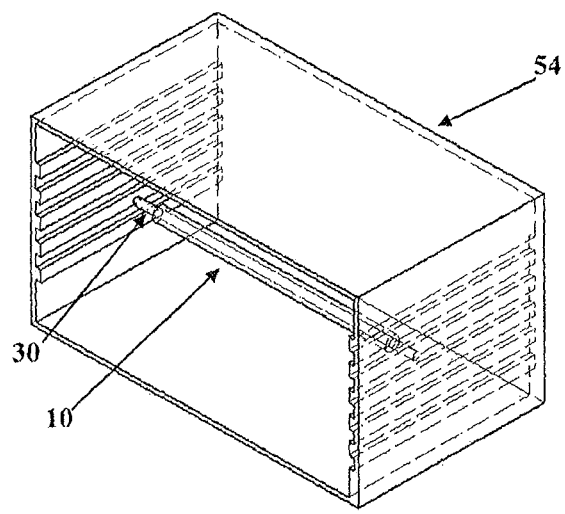
FIG. 17 is an isometric view illustration of an embodiment of a convection heater used to heat the medical device
Figure 18:
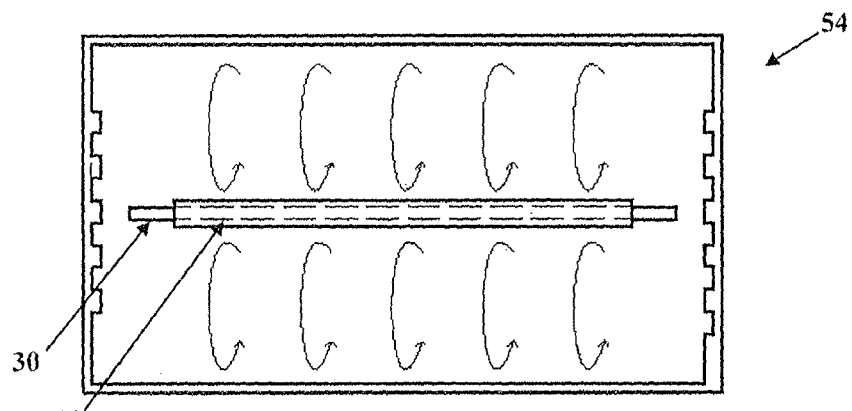
FIG. 18 is a side view illustration of an embodiment of a convection heater used to heat the medical device

FIGS. 17 and 18 illustrate the use of convection to heat the medical device 10 to the necessary temperature to allow for precise bending. A convective heating unit 54 such as a heat gun or oven warms air which is passed over the medical device 10 to heat it. The medical device 10 could pass through one or a series of the convection heating units 54 to be heated and prepared for bending.

Figure 19:
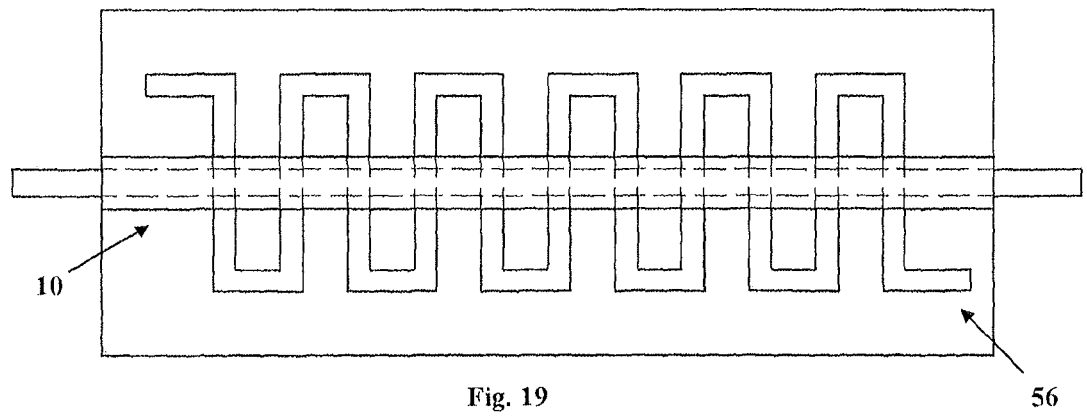
FIG. 19 is a top view illustration of an embodiment of a heating strip used to heat the medical device.

FIG. 19 illustrates another embodiment to be used for heating the medical device 10 including a heating strip 56. The heating strip can be comprised of any material or heating element that could pass heat to the medical device 10 sufficient to make the medical device 10 able to be bent precisely. Such heating devices could include a coil of resistive heating wire or a tube of heated liquid or gas. The medical device 10 would advance over the strip 56 either in contact or not, with resulting direct or indirect heating of the medical device 10. The medical device 10 could move over the heating strip 56 either incrementally with dwell time or in a smooth movement. The heating strip 56 could either be located in the medical curving apparatus 4 (FIG. 1) or used to heat the medical device 10 before it is used in the medical curving apparatus 4.

Figure 20:
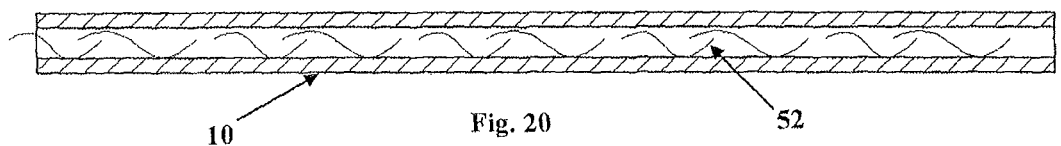
FIG. 20 is a section view illustration of steam traveling through a medical device to heat it.

FIG. 20 gives another example of a heating device including using steam or another gas to heat the medical device 10 to a bendable temperature. The steam heat 52 would flow through the lumen of the medical device 10 to heat it to the desired bending temperature. The flow could be pressurized to help control the inner diameter of the medical device 10. A cap could be added to the distal end of the medical device 10 to aid in pressure control to avoid any deformation during the bending process. The gas could be capped on both ends to maintain pressure. If the gas has only one end capped the other end could continually recycle new hot air into the medical device 10. Increasing the pressure in the medical device 10 just during bending could help reduce deformation. The capped end could have a release valve which would release cool air to allow room for hot air in the medical device 10. In all situations the pressure and temperature could be controlled by the user interface 3 (FIG. 1) to create a specific curve.

Figure 21:
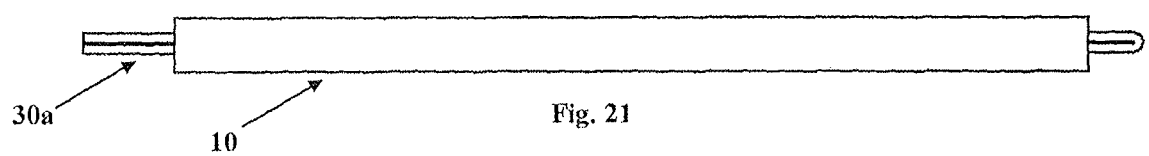
FIG. 21 is a side view illustration of an embodiment of a resistive heating mandrel used to heat the medical device.

FIG. 21 is an embodiment of a heating method utilizing a conductive mandrel 30*a* connected to an electric current to create heat and warm the medical device 10. The resistive heating mandrel 30*a* will be placed inside the lumen of the medical device 10 and the circuit controlled to heat the mandrel. The medical device 10 will be heated from the inside by direct contact with the mandrel 30*a*. The mandrel 30*a* could be removed following heating, or it could be retained in the lumen to maintain the size and shape of the inner diameter of the medical device 10 during bending.

Figure 22:
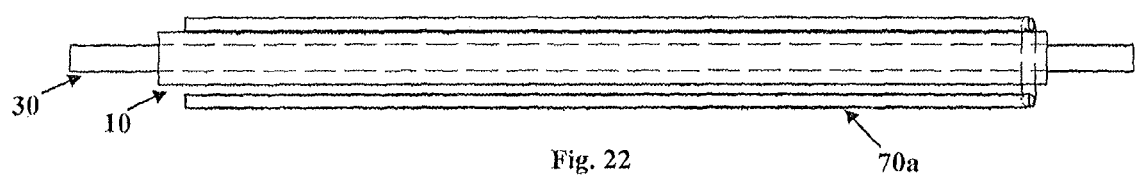
FIG. 22 is a plane view illustration of an embodiment of a resistive heating sheath used to heat the medical device.
Figure 23:
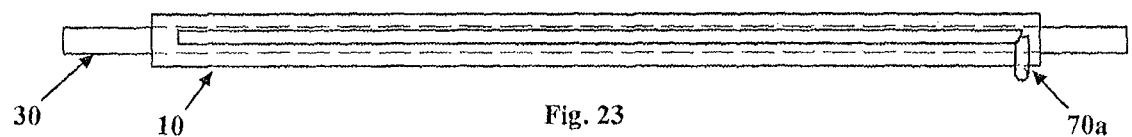
FIG. 23 is a side view illustration of an embodiment of a resistive heating sheath used to heat the medical device.

FIGS. 22 and 23 illustrate an embodiment of a heating method utilizing a conductive sheath 70*a* to heat the medical device 10 and optionally included mandrel 30 by resistive heating. The medical device 10 will either be placed into or move through the sheath 70*a* as the sheath 70*a* is heated by electric current. The sheath 70*a* could be the full length of the medical device or cover only a section at a time, and the sheath 70*a* could be flexible or inflexible, solid or a wire mesh or rod, and be either one part or multiple that can be removed to expose the heated medical device 10. The optionally included mandrel 30 could either be an insulator to only hold the shape of the inner diameter of the medical device 10, or it could be able to be heated to retain high temperatures and allow the medical device 10 to bend more easily.

Figure 24:
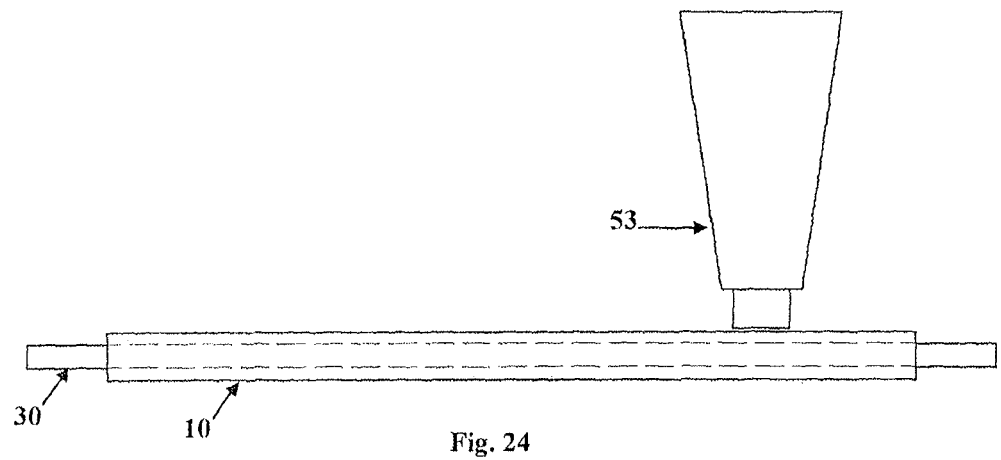
FIG. 24 is a side view illustration of an embodiment of a laser used to heat the medical device.

FIG. 24 illustrates an embodiment of a heating method utilizing a laser 53 to heat a localized region of the medical device 10. The laser 53 provides heat directly to a narrow portion of the medical device 10 to a programmable amount of time to make the medical device 10 malleable for bending. The mandrel 30 may be included to maintain the inner diameter of the medical device 10. Alternately, the narrow field of heating with the laser would allow for a series of very small steps in the heating and bending process. Bends that small would have a negligible effect on the inner diameter of the medical device 10, so the mandrel 30 would not be necessary. A laser 53 could also be used to heat a sheath 70*a* (FIG. 22). This would heat a wider area of the medical device 10 but could also reduce damage by the laser directly on the medical device 10. Other methods of heating a very localized region of the medical device 10 are also contemplated, using electromagnetic radiation, microwave, hot air jet, and infrared heat that use an outer sheath 70*a* (FIG. 22), directly heat the medical device 10, or heat the mandrel 30.

An alternative embodiment with similar characteristics would be to utilize ultrasonic heating in localized regions of the medical device 10. The heating device would contact a specified portion of the medical device 10 and produce heat through high-frequency ultrasonic acoustic vibrations. The mandrel 30 could either be included to aid in maintaining the inner diameter of the medical device 10 or the heating and bending could be performed on a series of very small lengths, rendering the mandrel 30 unnecessary. The ultrasonic heating could also be used to heat the mandrel 30 which would in turn heat the medical device 10.

Figure 25:
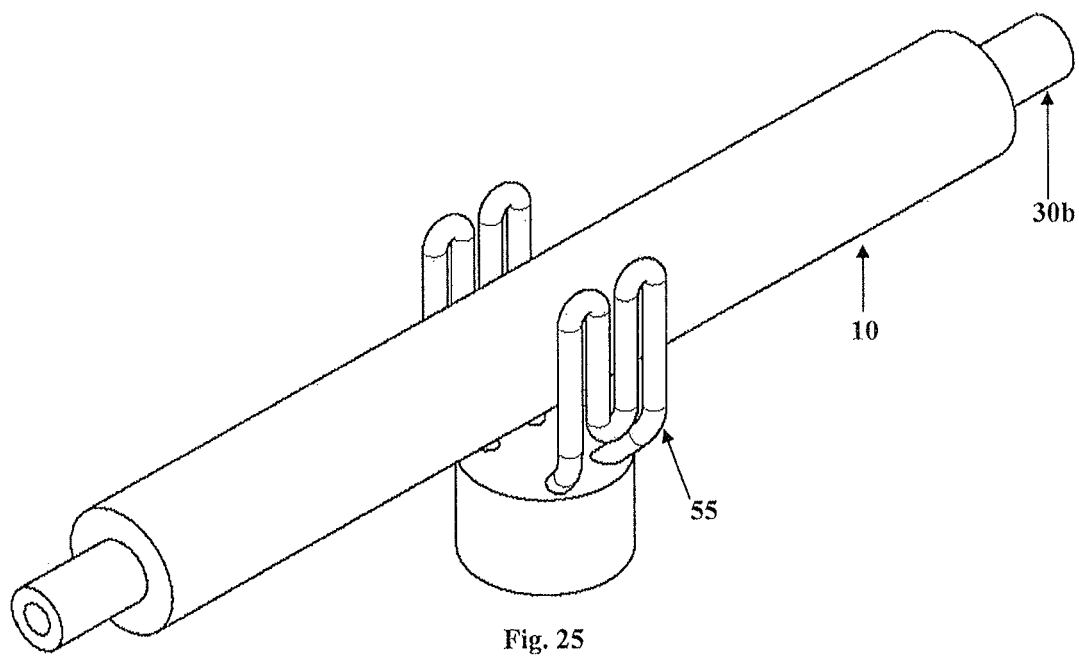
FIG. 25 is an isometric view illustration of an embodiment of an induction coil used to heat the medical device.

FIG. 25 is an embodiment of a heating method utilizing induction. The induction coil 55 is connected to a circuit with electrical current running through it. The mandrel 30*b* is composed of a ferromagnetic material. The medical device 10 is placed inside the induction coil 55 with the mandrel 30*b* inserted in the lumen so that the assembly is located within the coil's magnetic field. This magnetic field induces a current in the ferromagnetic mandrel 30*b*, causing it to heat. The mandrel will directly exchange heat with the medical device 10 to make it malleable. The maximum temperature can be controlled by utilizing ferromagnetic mandrels of varying materials, each of which have a different Curie point and will therefore only heat inductively to a given temperature. The time the mandrel 30*b* is in the magnetic field effects the temperature the mandrel 30*b* will reach. To keep the mandrel 30*b* from passing the melting point of the medical device 10 the time in the magnetic field is limited. This method protects the outer surface area of the medical device 10 by heating the device from the inside. The heat is also localized to the section of the device located within the induction coils, providing precision heating and ensuring no extraneous parts are heated.

Figure 26:
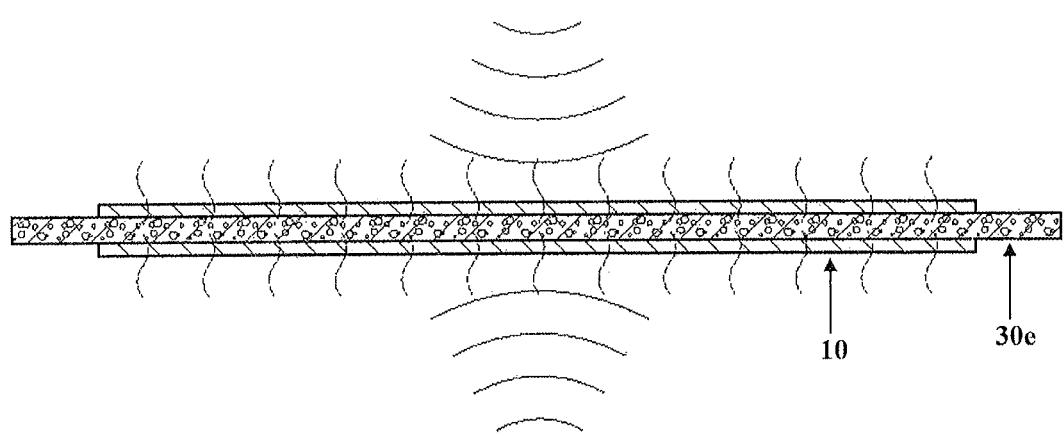
FIG. 26 is a section view illustration of an embodiment of a medical device and mandrel comprised of inductive particles in a rubber matrix.

FIG. 26 illustrates an alternative embodiment for the induction heating mandrel. To utilize a material with a low Curie Point or a material that is brittle, the ferromagnetic material is broken into pieces and formed within a rubber matrix to make the inductive mandrel 30e. When placed in the induction coils, the mandrel will heat to the particles' Curie Point and directly heat the inside of the medical device 10. The mandrel 30e will also provide support for the inner diameter of the medical device.

Figure 27:
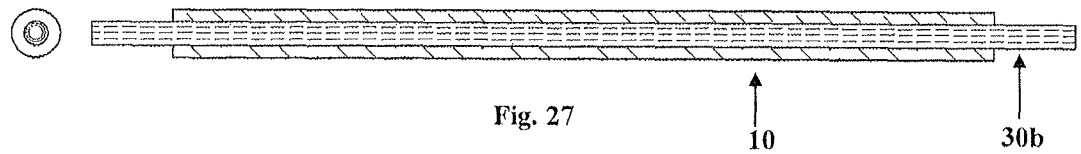
FIG. 27 is a section view illustration of an embodiment of a medical device with a composite mandrel.

FIG. 27 illustrates an alternative embodiment for the mandrel 30 utilizing composite materials. The composite mandrel 30b could be made out of any combination of materials necessary to function with the chosen embodiment. This mandrel 30b could be composed of any number of layers with any combination of materials that create the desired malleability, heat sensitivity, durability, strength, sterility, and thickness for the curving process. An example could be a readily malleable rubber rod surrounded by a ferromagnetic material to be used for inductive heating, all covered by a safe, sterile, nonstick coating to protect the lumen walls of the medical device 10. Materials within the mandrel can also be used in conjunction with the bending tool (no shown) so that a sensor in the bending tool can determine the mandrel position relative to the bending tool. Magnetic particles or iron particles are commonly used for this purpose, though any known material now or in the future may also be used.

A different type of composite mandrel 30 would be composed of different materials with different coefficients of thermal expansion. This would cause a specific temperature to cause a specific corresponding radius of curvature in the mandrel. This type of composite material does not have to be limited to the mandrel and could also be used in other features of the curving apparatus 4 (FIG. 1).

Figure 28:
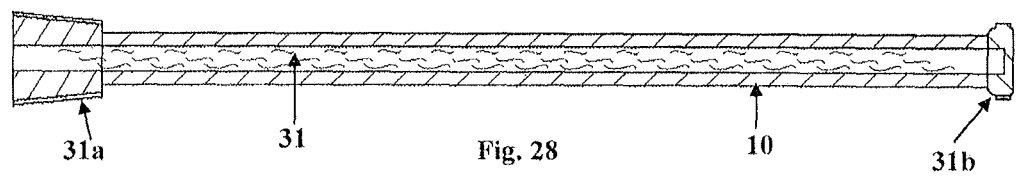
FIG. 28 is a section view illustration of pressurized air flowing through the medical device to control the inner diameter.

FIG. 28 is an alternative embodiment of the mandrel 30 wherein pressurized air or another gas flows through the medical device 10 to maintain the inner diameter. An entry valve or nozzle 31a at the proximal end of the medical device 10 injects pressurized gas 31 into the lumen of the device. An end cap 31d may seal the distal end of the medical device 10 to prevent the gas from escaping out the end. The pressurized gas 31 may be heated to heat the medical device 10 for bending, or the gas mandrel could be used in conjunction with a previously stated method of heating. Following the bending process, the caps 31a and 31b can be removed to allow the gas to escape. Alternately the end cap 31d can have a release valve to continually circulate out the cold air and allow hot air to enter the entry valve or nozzle 31a.

Figure 29:
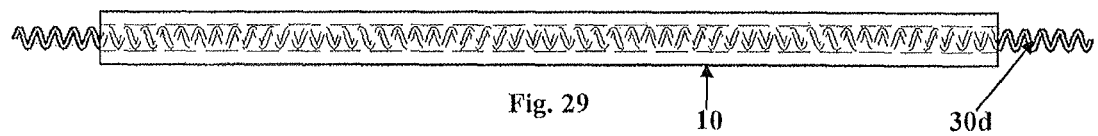
FIG. 29 is a section view illustration of an embodiment of a spring mandrel inserted in a medical device.

FIG. 29 is an alternative embodiment of the mandrel 30 wherein a spring mandrel 30d is utilized to retain the size and shape of the inner diameter during bending. The coiled wire spring mandrel 30d would be inserted into the lumen of the medical device 10 to hold the walls of the inner diameter in their original shape during bending. When the assembly is bent, the forming unit must overbend the medical device 10 by a preprogrammed amount because the elasticity of the spring will cause the bend to move back toward its original shape. Additionally, the assembly can be cooled during bending, such as with cooled air or water, to lessen rebounding of the curve. It is also contemplated that the spring mandrel could be heated by an electrical current to heat the medical device 10. Small nickel chromium wires could be coiled or run within an elastic mandrel material such as silicone rubber to act as a flexible mandrel heater.

Figure 30:
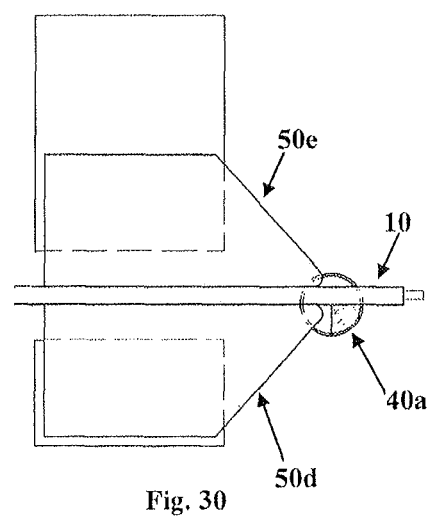
FIG. 30 is a plane view illustration of a forming unit embodiment wherein the distal ends of the grasping fixtures have been formed with a specified bending radius.
Figure 31:
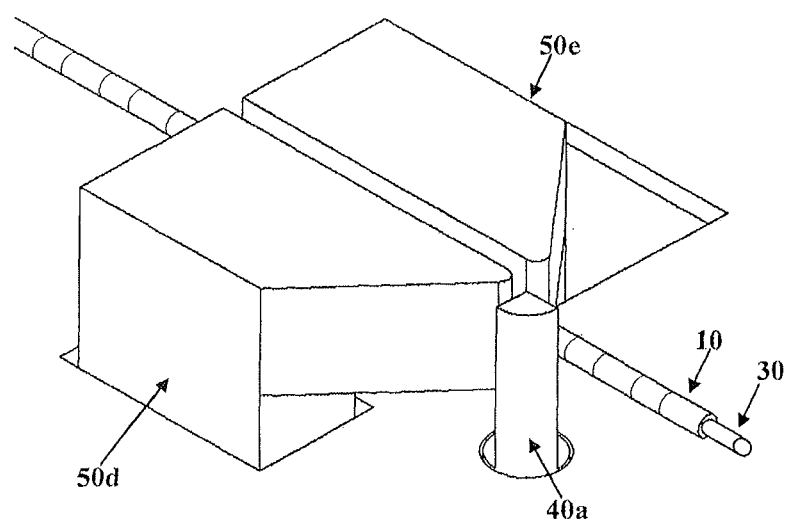
FIG. 31 is an isometric view illustration of the forming unit embodiment of FIG. 30.

FIGS. 30 and 31 detail an embodiment of the forming unit 50 of FIG. 8. The left and right grippers 50d and 50e have been designed to include a specified bending radius in their distal ends. A variable bending radius can be designed which would move inwards to increase the radius. The grippers 50d and 50e close to hold the medical device 10 and optionally included mandrel 30. At closure, the medical device 10 is held tangent to the radial curve at the distal end of the grippers 50e and 50d. The pie-shaped bending tool 40a can be moved to either side of the medical device and raised to be located next to the medical device 10. The bending tool 40a can then turn a preprogrammed amount to bend the medical device 10 around the radial curve at the distal end of either the left or right gripper 50d or 50e. The bending tool 40a then returns to its original position, the forming units 50d and 50e release the medical device 10, and the device is advanced by a small amount. These steps are repeated by a preprogrammed or calculated number of steps with set degrees of bending to create the desired curve for the medical device 10. Because the bending radius is a set angle on the grippers 50d and 50e, the degree and frequency of bends in the medical device 10 must vary to alter the size and shape of the given curve. For tighter curves, the bending tool 40a must rotate farther and bend the device at smaller increments. Larger curves require less bending rotation from the bending tool 40a at larger increments of the medical device 10. Alternatively, the bending tool 40a could be cylindrical shaped and move in an sweeping arc motion around the distal end of the grippers 50d and 50e to bend the medical device 10.

Figure 32:
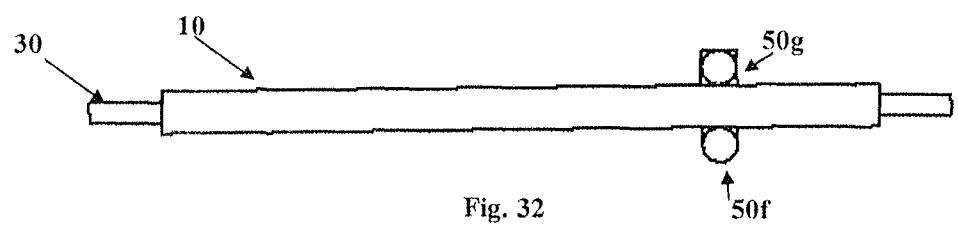
FIG. 32 is a plane view illustration of a forming unit embodiment including a cylinder with a bending radius and a roller to bend the device around the cylinder.
Figure 33:
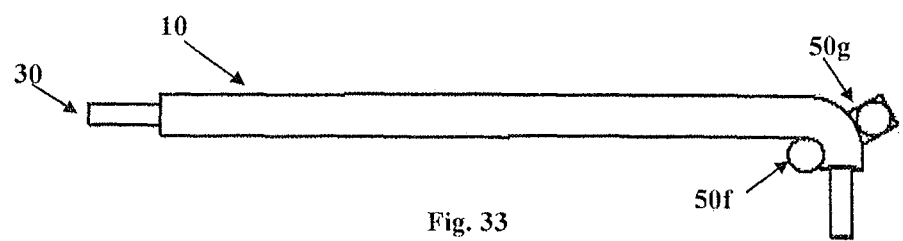
FIG. 33 is a plane view illustration of the forming unit of FIG. 32 wherein the roller has formed the bend.

FIGS. 32 and 33 detail an alternative embodiment of a combined forming unit 50 and bending tool 40 of FIG. 8. Following heating, the medical device 10 and mandrel 30 advance into the forming unit composed of a main curved cylinder 50f of a given bending radius and a guide roller 50g that rolls around the cylinder. With the medical device 10 between the two cylinders, the guide roller 50g pivots around the main cylinder 50f, thereby imparting a curve to the medical device 10. The guide roller 50g then returns to its start position and the medical device can be incrementally advanced. A full curve is imparted to the medical device 10 by imparting a series of bends upon the medical device 10. The degree of rotation of the guide roller 50g and length of incremental movement of the medical device 10 can vary to control the size and angle of the curve created. The distance between the nonrotating cylinder 50f and the guide roller 50g can vary depending on the outer diameter of the medical device 10. To alter the radius created a different sized cylinder 50f could be cycled in and used.

Figure 34:
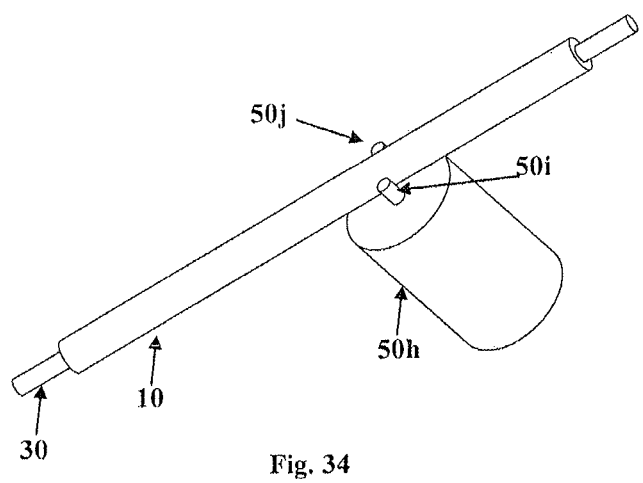
FIG. 34 is an isometric view illustration of a forming unit embodiment including a rotating cylinder with two prongs to hold the device.
Figure 35:
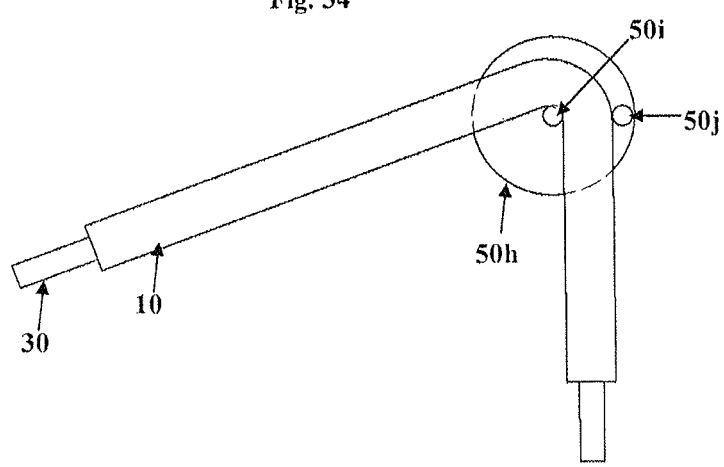
FIG. 35 is a plane view illustration of the forming unit of FIG. 34 wherein the two prongs have formed the bend in the medical device.

FIGS. 34 and 35 detail another embodiment of a combined forming unit 50 and bending tool 40 of FIG. 8. The forming unit is composed of a rotating cylindrical device 50h with two prongs of a given bending radius 50i and 50j protruding from the top. One of the prongs imparted with the given bending radius 50i will be located on the centerline axis on the top surface of the cylindrical device 50h and the outer prong 50j will be adjustably set a distance away from the centerline prong 50i on the surface of the device 50h with the distance between sized to fit the diameter of the medical device 10. The medical device 10 will be advanced into the gap between the prongs by means of any grasping fixture such as those described in FIGS. 11 through 16. When the medical device 10 is in place the rotating cylindrical device 50h will rotate the outer prong 50j, which will displace the medical device 10 around the centerline prong 50i. When the bend is complete the cylindrical device 50h will rotate back to its starting position to allow the medical device 10 to advance again. The full curve can be completed by utilizing many bends and advances in series. The imparted curve angles can be made larger or smaller by varying the degree of rotation of the cylindrical device 50h or the advancement increment size of the medical device 10. The curve can be formed to either direction by rotating the cylindrical device 50h either clockwise or counter clockwise.

Figure 36:
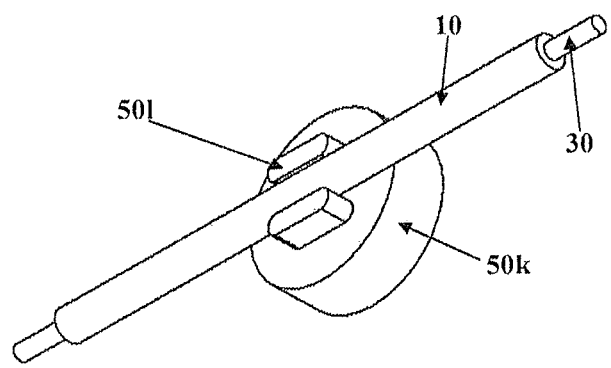
FIG. 36 is an isometric view illustration of a forming unit embodiment including a rotating cylinder with two dual radius benders.
Figure 37:
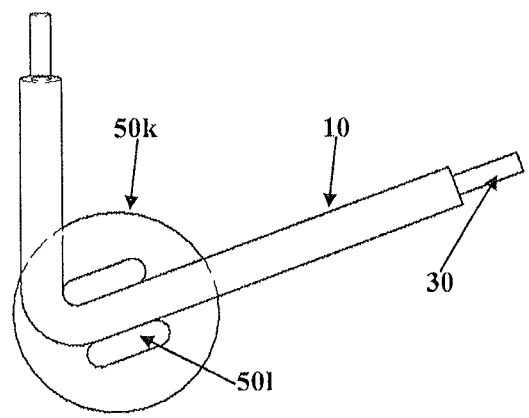
FIG. 37 is a plane view illustration of the forming unit of FIG. 36 showing the bend in the medical device.

FIGS. 36 and 37 detail another embodiment of the combined forming unit 50 and bending tool 40 of FIG. 8, where the medical device 10 fits in the slot of the dual radius bending fixture 501, which is located on the top surface of a rotating cylinder 50k. The proximal and distal ends of either side of the bending fixture 501 are formed with either the same or multiple selected radii. The centerline axis is located midway between the dual radius bending fixture 501. The medical device 10 and mandrel 30 advance by any way described above into the bending fixture 501. Due to the geometry of the dual radius bending fixture 501 only the closer side will create the bend. The rotating cylinder 50k has the ability to rotate 360 degrees in order for the other radii to be utilized. The full curve can be completed using many bends in any size increment to vary the angle of the curves.

Figure 38:
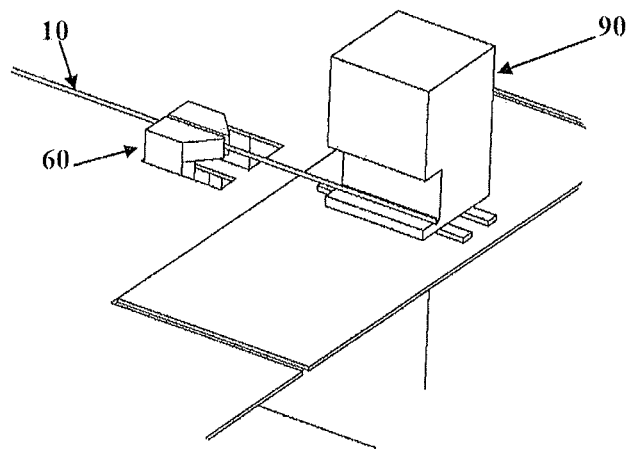
FIG. 38 is an isometric view illustration of an embodiment of a robotic forming unit.

FIG. 38 details an alternative embodiment of the combined forming unit 50 and bending tool 40 of FIG. 8, where the bending is achieved by means of a robot 90 such as a SCARA, Cartesian, or 6-axis machine. The medical device 10 can be heated to a malleable temperature either by a separate heating device or by integrating a heating unit into the grasping fixture 60 or the bending tool of the robot 90. The medical device 10 can be advanced through the fixtures by either pulling with the robot or advancing it with the grasping fixture 60 by any means described previously. The robot will contain a bending device with the ability to grasp and impart a curve upon the medical device 10. The bending process can be performed either incrementally or all at once to impart the full curvature on the medical device.

As shown in FIGS. 32 through 38, many configurations of forming units and bending tools are possible for the curving apparatus 4 of FIG. 8. The forming unit and bending tool may be combined into a single unit that is able to hold, heat, form, stabilize, and/or bend the medical device 10, or the forming unit and bending tool may be used alone to impart a permanent curve on the medical device 10. Any motion of a combined forming unit and bending tool, or the relative motion between the bending tool and the forming unit may be used to position a curve in order to create a "bend" in the medical device 10.

Figure 39:
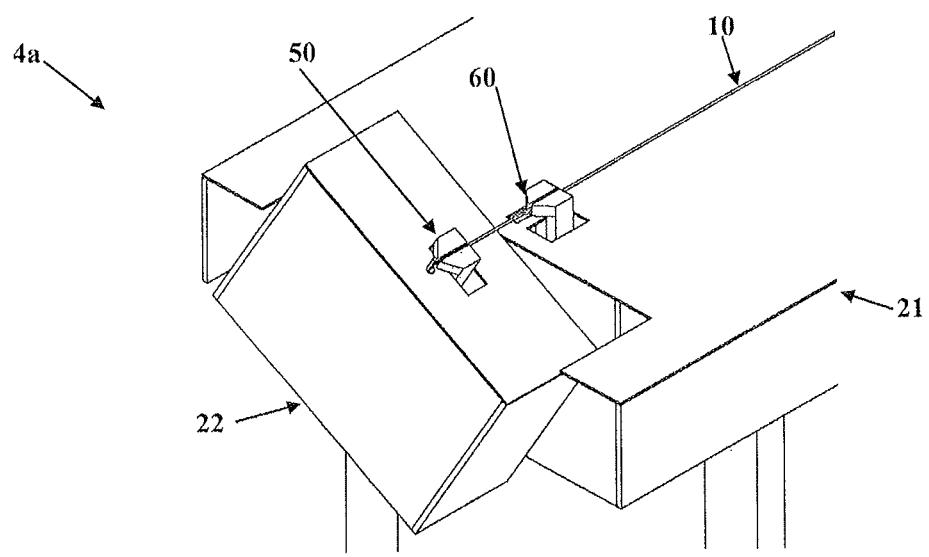
FIG. 39 is an isometric view of an embodiment of a forming unit rotating relative to the base to create a 2.5 or 3D shape.

FIG. 39 details an enlarged view embodiment of the curving apparatus 4a of FIG. 8 wherein the secondary base 22 rotates relative to the primary base 21 to aide in the forming of 2.5D and 3D bends by rotating the medical device. To rotate the medical device 10 for bending, the grasping fixture 60 grips the device while the forming unit 50 releases it. The secondary base 22 then rotates relative to the primary base 21 by a predetermined amount sufficient to turn the medical device 10 in the desired direction. The forming unit 50 then grasps the medical device and the grasping fixture 60 releases the device. The secondary base 22 then returns to its original position, rotating the medical device 10 along with it. This process can be repeated any number of times to turn the medical device 10 to the desired angle for bending. Once the precise angle has been reached, the previously discussed method of bending can be utilized to impart the curvature upon the medical device. Alternately a mechanism can be used to rotate the medical device 10 keeping the secondary base 22 always fixed. To grasp the medical device 10 the mechanism could inflate or pinch while the forming unit 50 and grasping fixture 60 releases the medical device 10 to allow for rotation. This mechanism would then rotate any number of degrees.

The medical device fits through a radial compressor and into in to the curving apparatus. Once the medical device is inserted through the radial device it compresses or inflates squeezing the medical device. The radial device does not release the pressure until after the curves are formed. This keeps the device always at a known location and spin. To keep the device from needing to release the medical device it will move linearly either along with the device or it can be the force that drives it forwards. There can be multiple radial devices that move linearly in sync and spin at the exact same degree upon ever motion.

Figure 40:
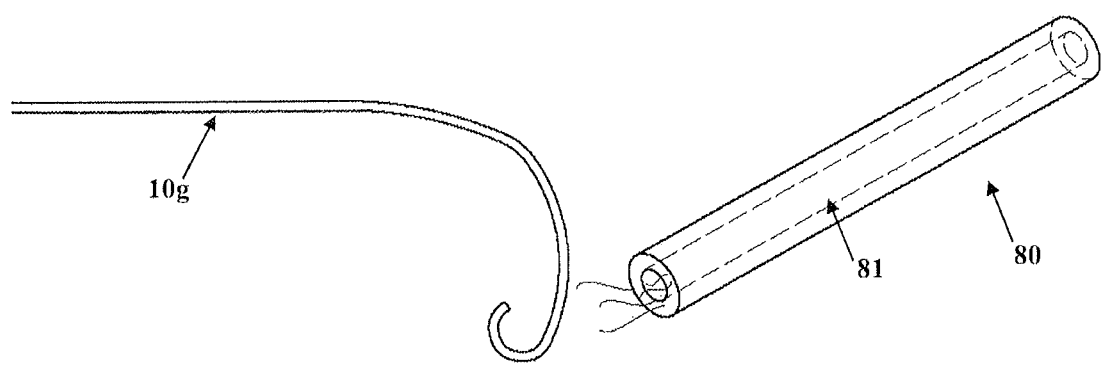
FIG. 40 is a plane view of a bent medical device being cooled by flowing air.

FIG. 40 illustrates an embodiment of a cooling mechanism 80 used to lower the temperature of the curved medical device 10g. Following bending, either while the curved medical device 10g is still held by the forming unit or after it has been advanced, a cooling mechanism can indirectly apply a stream of cool air or any other sterile, nontoxic gas or fluid to decrease the temperature of the curved device 10g. The cooling mechanism 80 will reduce the temperature of the curved medical device 10g below its malleability point so that the curvature sets permanently into the length of the device. Alternatively, a sterile liquid such as saline could be sprayed onto the medical device to produce the same effect, or the curved end of the medical device 10g can be placed in a bowl of sterile saline.

Additional embodiments of the cooling mechanism 80 could include a cool bath of any sterile, nontoxic, noncorrosive liquid such as water for the medical device 10 to be submerged into or a series of cooled pipes with chilled liquid or gas flowing through them upon which the medical device could be placed to cool. If the mandrel 30 (FIG. 8) being used is a solid material, a cold reservoir could come in contact with the protruding solid causing the heat from the mandrel 30 and medical device 10g to cool. Alternatively, refrigeration or any other known method of decreasing the temperature of the material could be employed.

Figure 41:
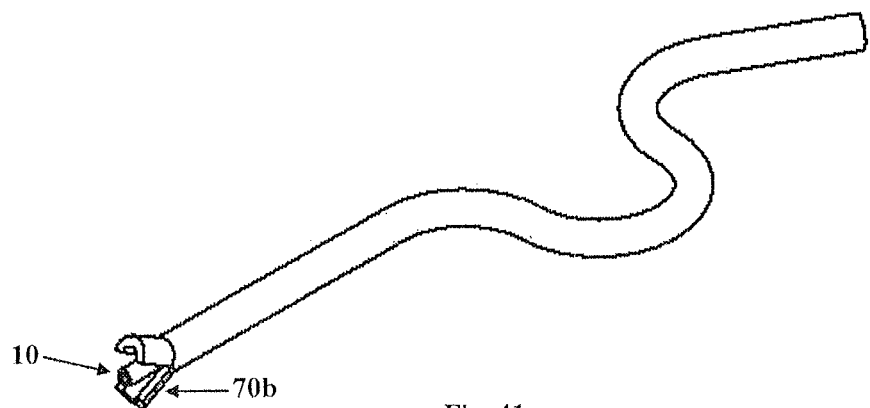
FIG. 41 is an isometric view of a medical device covered in a removable sleeve to maintain sterility.
Figure 41A:
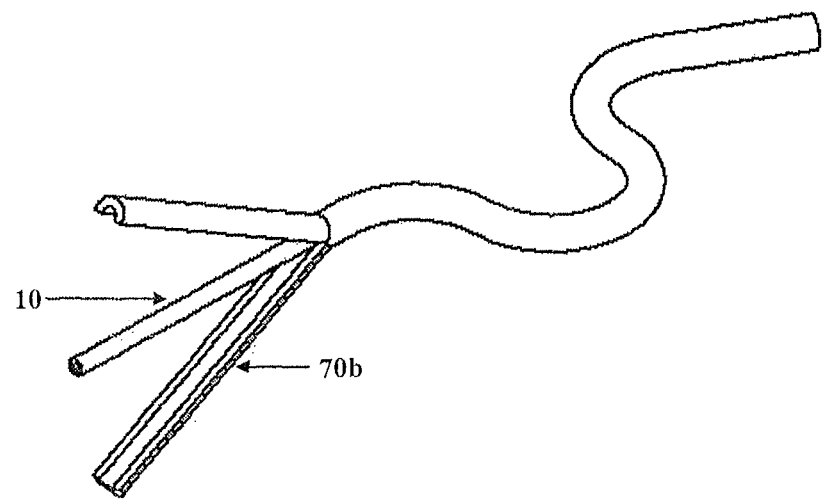
FIG. 41a is an isometric view of the medical device and sleeve from FIG. 41 with the sleeve partially removed.
Figure 41B:
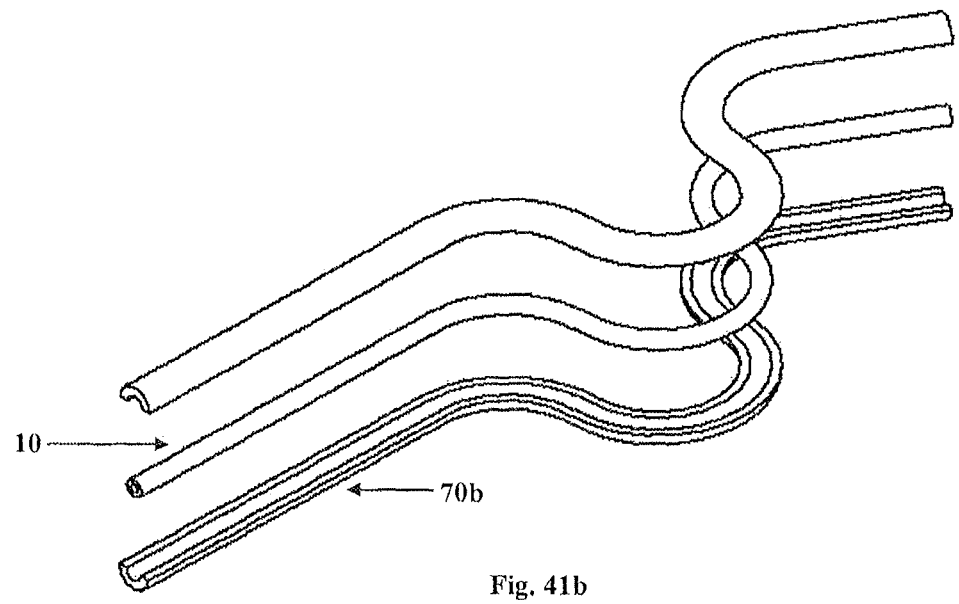
FIG. 41b is an isometric view of the medical device and sleeve from FIG. 41 with the sleeve fully removed.

FIGS. 41 through 41b depict an embodiment of the medical device 10 covered in a sterile sleeve 70b to maintain sterility. The sterile sleeve 70b will cover the entirety of the medical device 10 to protect it from any infectious agents that could come into contact with it during packaging, shipping, handling, bending, or cooling. The sterile sleeve could be composed of any gel, plastic, paper, rubber, composite, or any material that can be removably formed around the length of the medical device. The sterile sleeve 70b will have the ability to flex during the curving procedure to maintain sterility while not affecting the imparted bends. Additionally, the sterile sleeve 70b will be easily removable to enable use of the medical device 10 in medical procedures. The sterile sleeve could be placed over the entire medical device 10 after the mandrel 30 (FIG. 8) is set keeping the medical device 10 sterile throughout the curving process. The sterile sleeve 70b could roll, peel, slide, pull, dissolve or in any way detach from the medical device 10 when the device is ready to be used.

Figure 42:
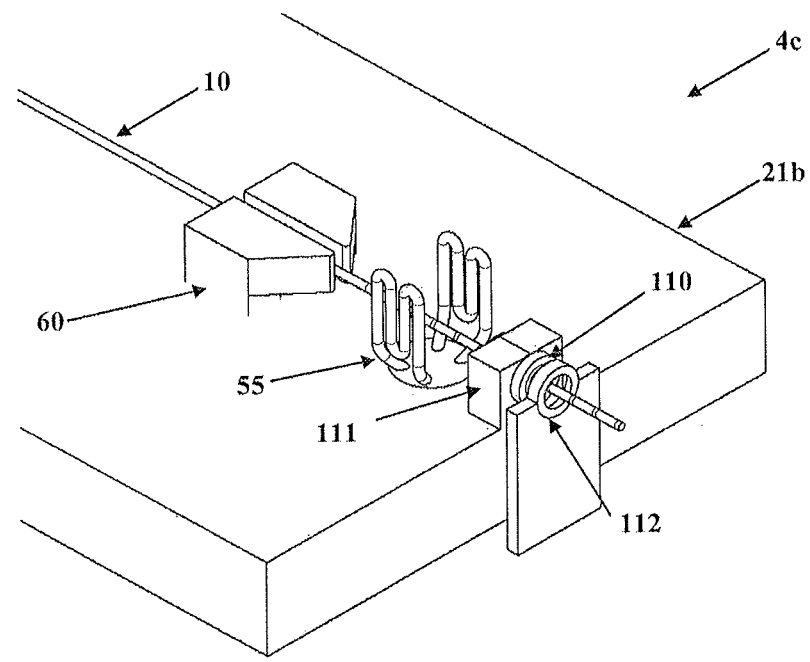
FIG. 42 is a pictorial view of a curving apparatus embodiment showing an induction coil as the heat source and a dual axis bending tool.
Figure 43:
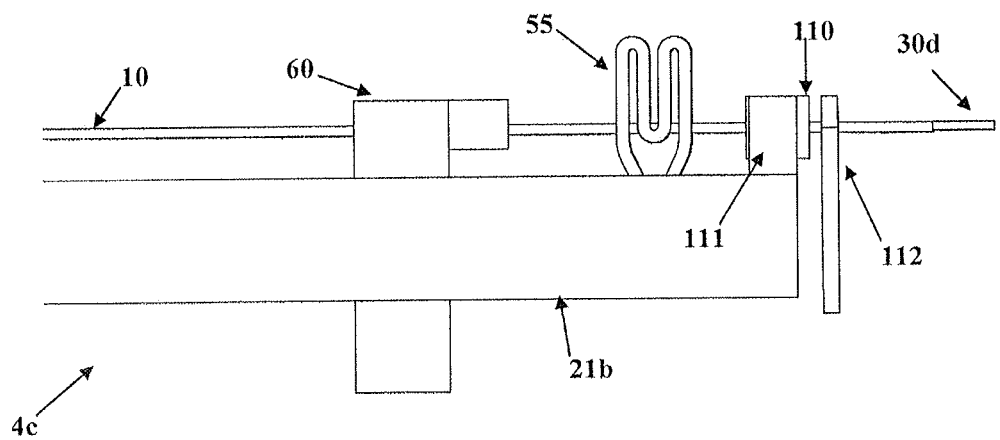
FIG. 43 is a side view of the curving apparatus embodiment of FIG. 42.

FIGS. 42 through 43 illustrate a curving apparatus 4c embodiment excluding a barrier 20. The apparatus has a primary base 21b on which the components rest or are attached permanently or removably. The medical device 10 is held in place by any of the previously mentioned embodiments of the grasping fixture 60 or by any other means now known or discovered in the future that allows the medical device 10 to be releasably gripped. The embodiments of the grasping fixture 60 can also advance the device by sliding, stepping, pushing, pulling, twisting, or by any other means by which a body can be made to move. The medical device 10 will be heated to the necessary bending temperature by means of induction heating wherein the induction coils 55 will produce a magnetic field that will induce a current in the lumen of the medical device 10 by means of a mandrel 30d, which will be a solid, a liquid, or a composite including inductive material that will heat when an electric current is induced in it. The heat from the mandrel 30d will be directly transferred to the inner surface of the medical device 10 to heat it to a malleable temperature. Following heating, the medical device will be advanced by means of the grasping fixture 60 or any other method previously stated into the holder 110, which will be a cylindrical device used to support the medical device 10 and be removably attachable to the primary base 21b by means of a coupler 111. A bending tool 112 movable linearly in 3 dimensions, or rotationally about all three axis can impart any 2d or 3d curve shape to the medical device 10.

Figure 43A:
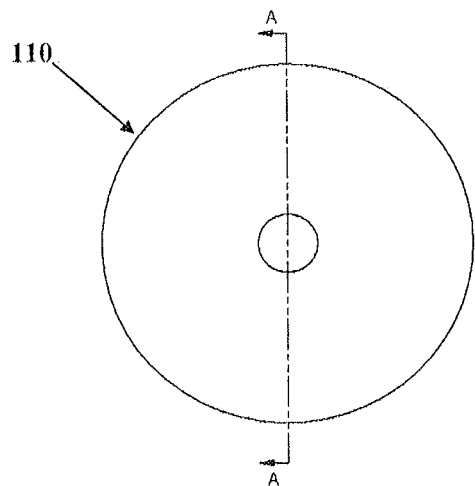
FIG. 43a is an enlarged view of the holder for the curving apparatus embodiment of FIG. 42.
Figure 43B:
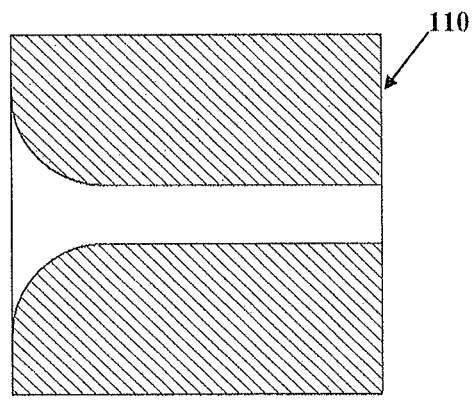
FIG. 43b is a section view of the holder for the curving apparatus embodiment of FIG. 42.

FIGS. 43a and 43b are enlarged views of the holder 110 detailing the cylindrical hole sized to fit the diameter of the medical device 10 and the rounded fillet at the distal end sized to the desired bending radius. The outer diameter of the holder can be rounded or any other shape to allow for easy attachment to the primary base 21b by means of a coupler 111. The coupler-holder system could be one piece or an assembly and could combine with the primary base by gripping, snapping, latching, hook and loop fastening, tightening, or by any other known methods of connection. The medical device 10 can be advanced a predetermined amount through the holding apparatus 110 by means of the clamping and moving motions of the grasping fixture 60. When the medical device 10 has advanced into the curved portion of the holder 110, the circular bending tool 112 moves to push the medical device around the holding device's curving fixture, thereby imparting a bend on the medical device. Because the desired bend radius is incorporated in the full circular form of both the distal end of the holder 110 and the proximal side of the bending tool 112, the bending device could push in any direction; up, down, side to side, or turning to create a bend in any desired direction. A different form of the circular bending tool 112 could allow for bending in any direction 360 degrees around.

Figure 43C:
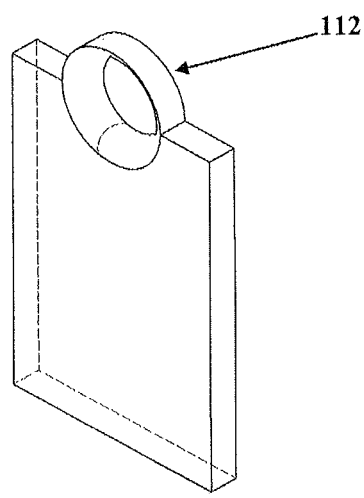
FIG. 43c is an enlarged view of the bending tool for the curving apparatus embodiment of FIG. 42.

FIG. 43c illustrates an enlarged view of the bending tool 112. The movement of the bending tool 112 can be controlled by actuators, gears, SCARA or other robotic devices, servos, stepper motors, or any other method mechanical or otherwise to maneuver the bending tool in any desired direction. The combination of incremental advancing of the medical device 10 by the grasping fixture 60 and bending by the holder 110 and bending tool 112 can create any programed curvature in 2D, 2.5D, or 3D. It is also contemplated that the bending tool 112 could be open at the top portion or could be flexed open, or split apart to allow the medical device 10 (not shown) to be more easily removed after curving.

Figure 43D:
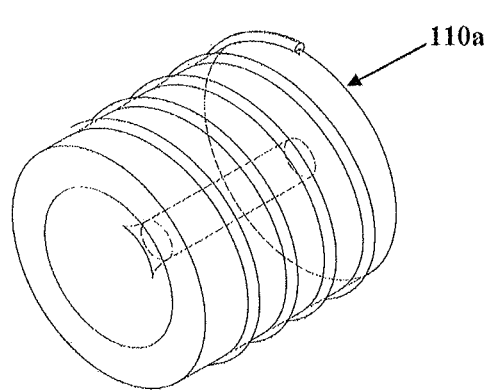
FIG. 43d is a pictorial view of the holder for the curving apparatus embodiment of FIG. 42 with incorporated induction coils.

FIG. 43d pictures an alternative embodiment of the grasping and heating fixtures for the curving apparatus 4c of FIG. 42 and is comprised of a holder with incorporated induction coils 110a. In place of separate heating and holding units, the heating unit is integrated into the holder. This assembly allows the device to be held firmly in place while it is being heated as well as decreases the distance between the heating and bending tools. Optionally different holders 110 with different radii can be switched.

Figure 43E:
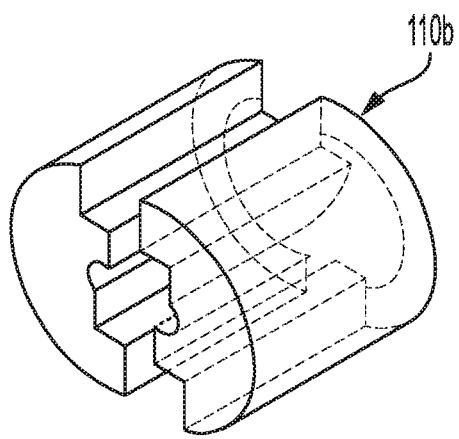
FIG. 43e is an isometric view of the holder for the curving apparatus embodiment of FIG. 42 separated into two pieces.

FIG. 43e details an embodiment of the holder 110b wherein the holder can be split apart following bending to allow for easy removal of the medical device 10. Following bending, the holder 110b can break, flex or hinge open, pull apart, snap apart, slide over the device or slide pieces apart, or in any other way become removable to disconnect the holder 110b from the medical device 10. The holder 110b could be formed out of a flexible material with a small pull tab so that the cylindrical object could be flexed open enough to remove the medical device. The holder 110b could have an inflatable or moldable center which allows different radii medical devices 10 to be used in the same holder 110b. For some curvatures, the holder 110b could also not fully enclose the medical device. The holder 110b could be semi-circular or some other shape so that the medical device 10 could be bent around one side of the distal end and be open on the other side to allow for easy removal. Similar removal schemes may be utilized for the bending tool 112, which will also have to be removed following the bending procedure.

Figure 44:
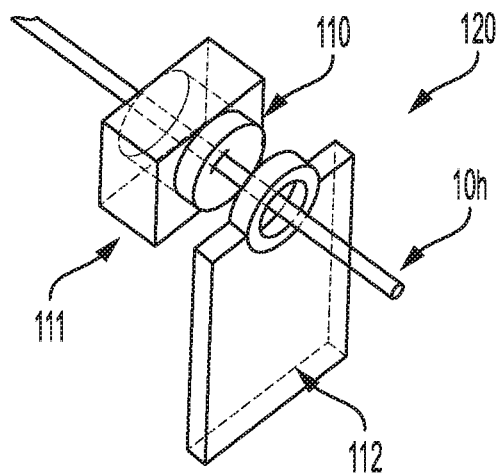
FIG. 44 is an enlarged pictorial view of an embodiment of a sterile assembly.

FIG. 44 illustrates an embodiment of a sterile package 120 that will contain the medical device 10, holder 110b, coupler 111, and circular bending tool 112 and prevent these components from coming into contact with infectious agents. The holder 110b, coupler 111, and bending tool 112 must be included in the sterile bending package because the medical device 10 cannot come into contact with any non-sterile surfaces. The packaging, not shown, of the sterile package 120 will form a physical barrier, be either flexible or rigid, be either clear or opaque, be sealed, and contain any other attributes necessary to ensure the components remain free of infectious agents. The packaging will also have a label containing detailed instructions on proper handling and use, serial and lot numbers, the expiration date of the components, and any other necessary information regarding the package 120.

Figure 45:
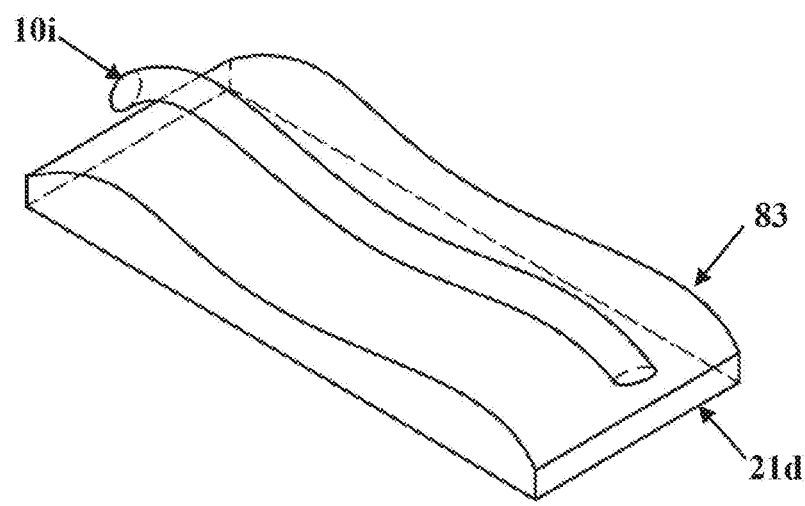
FIG. 45 is a pictorial view of an embodiment of a base for the curving apparatus wherein the primary base can be formed to create the curve shape (warped surface).

FIG. 45 is a pictorial view of a primary base embodiment wherein the primary base 21d has a flexible surface 83 that can assume the shape of the desired curve and have the ability to impart the curve to the medical device 10i. The flexible surface 83 can be a field of moveable pins or nails that can adjust to varying heights, a ferromagnetic material that can move with changes in a magnetic field, a rubber or gel of any material that can be formed to numerous shapes, or any other material or mechanism that can move laterally, raise, lower, twist, bend, or in any other way take on the shape of the desired curvature. The flexible surface 83 will have the ability to impart the curvature on the medical device 10i by heat forming, pressing, grasping, or clamping the device. To aid in the bending process, the flexible surface could contain a heating device so that the medical device 10i could become malleable and therefore accept the curvature more readily. A flexible press could be utilized to mold the medical device 10i into the shape of the flexible primary base 21d.

Figure 46:
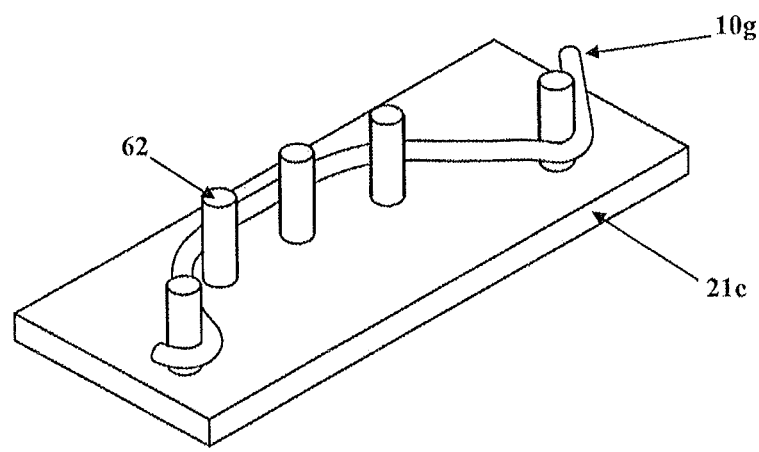
FIG. 46 is an isometric view embodiment of a base for the curving apparatus wherein spokes or pins can move to hold the medical device in a specified shape.

FIG. 46 is a pictorial view of a primary base embodiment wherein the primary base is equipped with a series of moveable pins 62 that will hold the medical device 10g and shape it into the desired curvature. The moveable pins 62 could be composed of metal, rubber, plastic, or any other material that can hold the medical device 10g and force the device into the curvature. The pins will be imparted with a bending radius and be able to move in any direction needed to produce the most accurate curvature. The pins could be placed on both or a single side of the medical device, and they could be programmed to move as a unit or individually. Heaters could optionally be included in the pins to aid in the precision of bending. Secondary pins could be used to push the medical device 10g against the pins 62 and into the desired shape.

Figure 47:
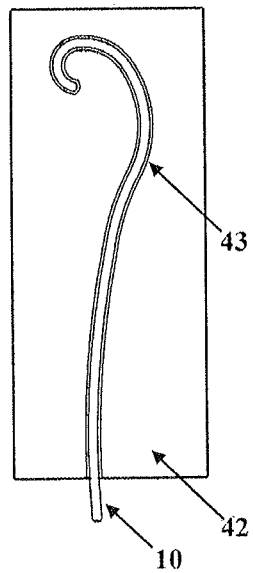
FIG. 47 is a top view embodiment of a mold plate with incorporated curve to shape the medical device.
Figure 48:
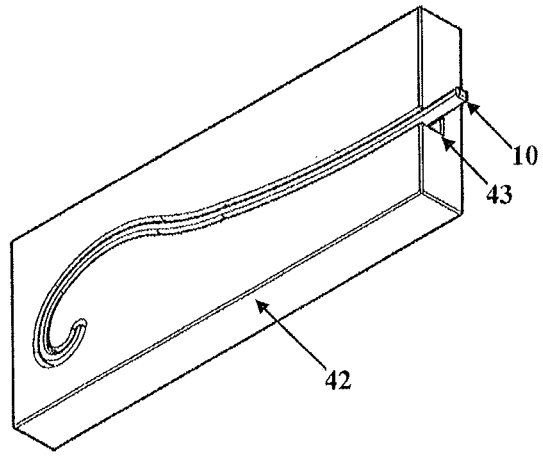
FIG. 48 is a pictorial view of the embodiment of FIG. 47.

FIGS. 47 and 48 illustrate the use of a mold plate 42 to impart a curve on a medical device 10. The mold plate 42 could be Aluminum, Ceramic, Steel, Rubber, Wax, or any other material that could have a channel 43 in the shape of the desired curvature imparted into it, whether by cutting, molding, or any other means. The medical device 10 will be placed into the channel 43 to take the shape of the curvature. To permanently set the curvature in the medical device, the mold plate and device could be heated using any of the means discussed previously, including convection, or the device could be chemically set. The molds could be made based on the desired curve by the curving apparatus 4 (FIG. 1) or manually produced.

Figure 49:
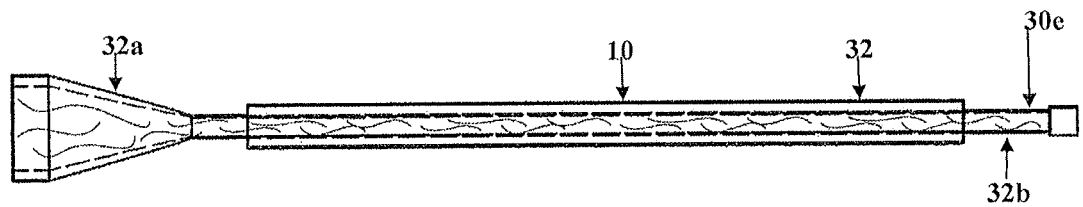
FIG. 49 is a side view illustration of a medical device with included air or fluid pressurized mandrel.

FIG. 49 is an alternative embodiment of the mandrel wherein a hollow mandrel 30e is inserted into the lumen of the medical device 10 and either a fluid or gas flows through it to either heat the medical device or hold the inner diameter of the medical device constant or both. The hollow mandrel 30e can be formed to have either an inflexible outer diameter or an expandable shape to form to and hold the shape of the medical device's inner diameter. A fluid or gas such as carbon dioxide, nitrogen, water, steam, or air will flow through the hollow mandrel 30e. This fluid or gas could be heated to increase the temperature of the medical device to the desired malleability point, and the fluid or gas could be pressurized so that the mandrel expands to hold the inner diameter of the medical device steady. The proximal end of the mandrel will be connected to a pump 32a and optionally included heater to heat and push the fluid or gas through the lumen of the mandrel. The distal end of the hollow mandrel 30e could be capped or sealed to hold in the liquid or gas if a higher pressure is desired, or the mandrel could be connected to a receptacle that will receive the fluid or gas after it has traveled through the mandrel. This catching receptacle could have a means to return the fluid or gas to the proximal pump for recirculation.

Figure 50:
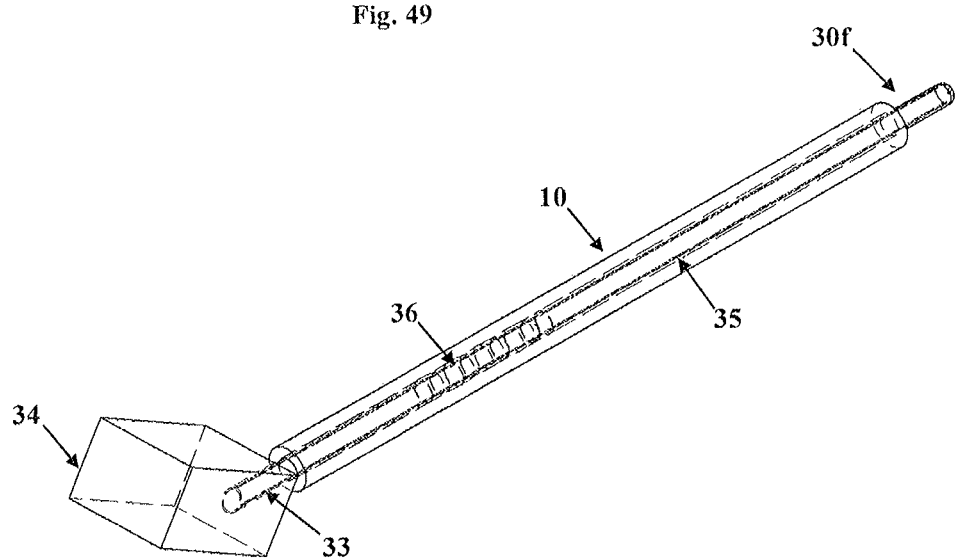
FIG. 50 is a pictorial view illustration of a medical device being heated by a heat pipe mandrel.

FIG. 50 is an alternative embodiment of the mandrel wherein a heat pipe mandrel 30f will be inserted into the lumen of the medical device 10 to heat the device to the desired malleability temperature. A heater 34 at the proximal end of the heat pipe mandrel 30f will heat the conductive pipe 33, which will directly heat the enclosed working fluid, either water or any other fluid that could be vaporized and condensed, to vaporization temperatures. The steam will travel up the vertically inclined mandrel 30f toward the non-heated, closed end of the pipe where it will cool and condense. The heat being expelled from the steam will dissipate through the conductive tubing and into the medical device 30f. The condensed fluid will then be captured by the wick 35 lining the inner surface of the mandrel, which will control its return down the pipe via gravity to the heater. One or more flexible bellows 36 segments can be added to the portions of the mandrel that would be bent during the curving process.

Figure 50A:
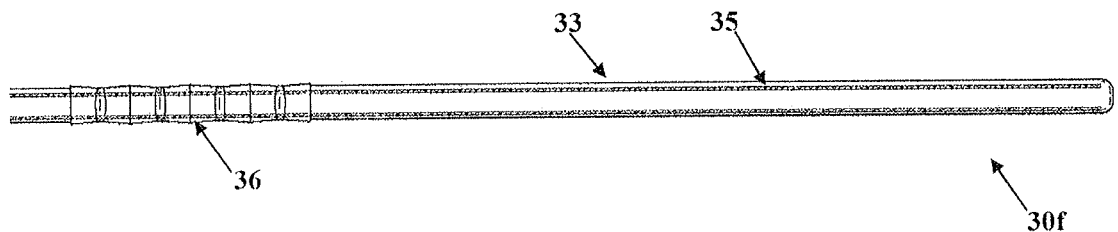
FIG. 50a is a side view illustration of the heat pipe mandrel of the embodiment of FIG. 50.

FIG. 50a gives a detailed illustration of the heat pipe mandrel 30f with the wick 35 and flexible bellows 36 that allow the pipe to bend within the lumen of the medical device.

Figure 51:
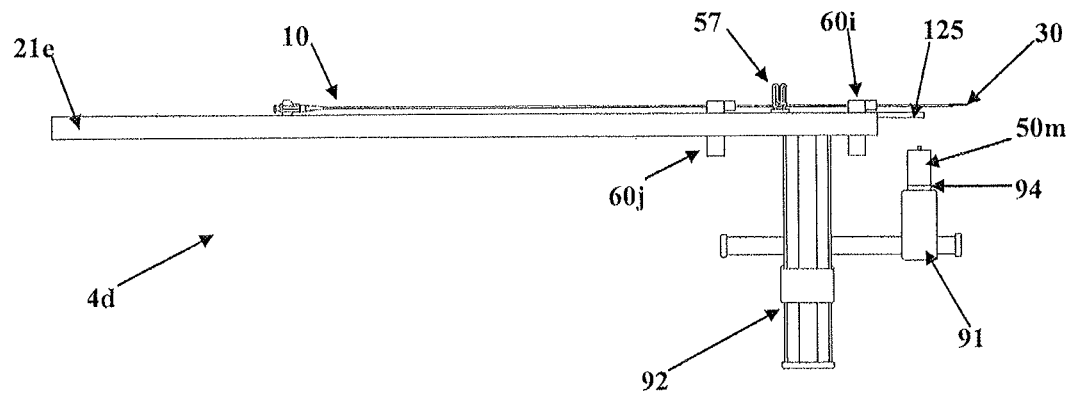
FIG. 51 is a side view illustration of an embodiment of a linearly controlled robotic curving apparatus.
Figure 52:
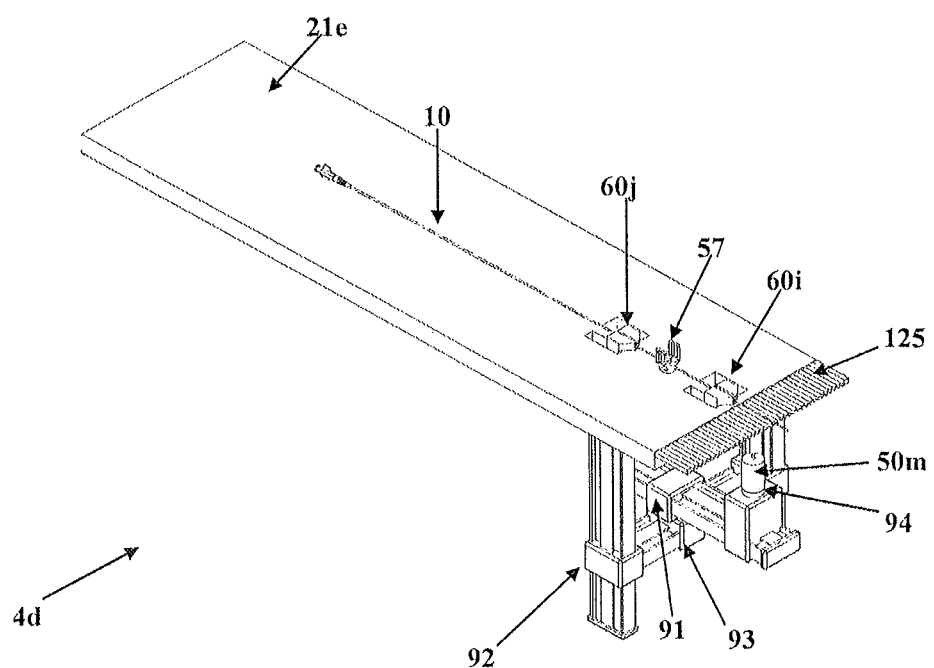
FIG. 52 is an isometric view of the apparatus embodiment of FIG. 51.
Figure 53:
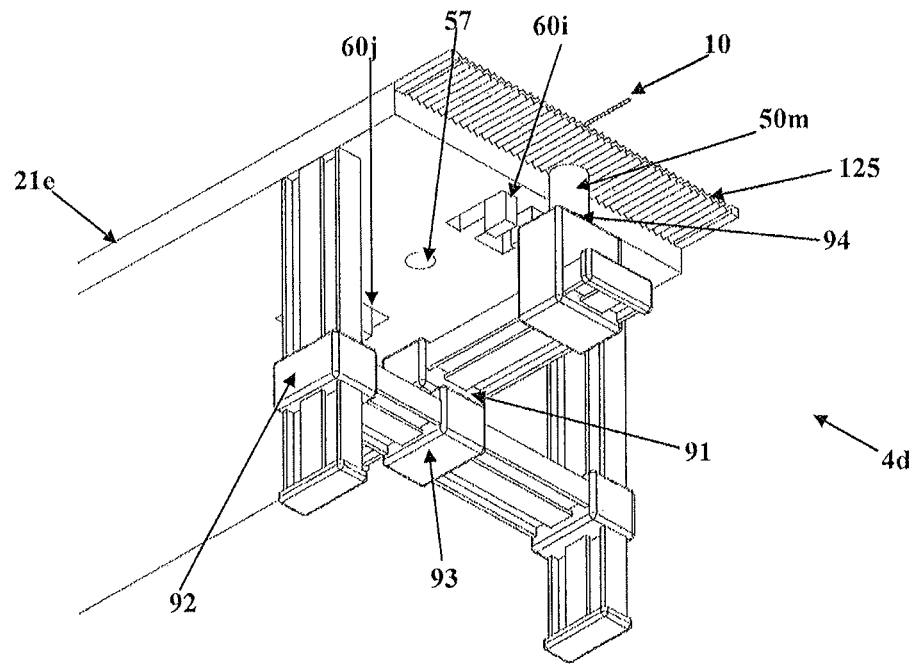
FIG. 53 is a pictorial section view of the apparatus embodiment of FIG. 51.

FIGS. 51 through 53 detail an embodiment of the curving apparatus 4d comprised of a linear robotic curving device. The linear robotic curving apparatus 4d contains a primary base 21e, distal and optionally included proximal grasping fixtures 60i and 60j that may or may not have the ability to move (as previously discussed in FIGS. 11 through 16), a heating unit 57, x-, y-, and z-axis linear actuators 91, 92, and 93, a theta axis motor 94, and a bending tool 50m which can be of any form as previously discussed in FIGS. 32 through 37. The distal and proximal grasping fixtures 60i and 60j grip the medical device 10 and optionally included mandrel 30 to hold the device in line with the heating unit 57, which could alternatively be incorporated into the grasping fixtures. The grasping fixtures could advance the medical device by any means previously stated, or the medical device could be incrementally advanced by means of the bending tool 50m, which can rotate to grasp the device by virtue of the theta axis motor 94 and advance using any combination of the x-, y-, and z-axis linear actuators 91, 92, and 93 necessary to advance the medical device by the precise amount desired. When the medical device has been advanced past the grasping fixtures, the bending tool will move to a preprogrammed position and begin the bend by moving axially using the, x-, y-, and z-axis linear actuators and rotating with the theta axis motor. The bending tool will move along the length of the medical device while performing the necessary rotations to form the curvature for the given incremental length, and then the medical device will be advanced again.

An alternative embodiment of the use of incremental advancement of the medical device 10 using the bending tool 50m incorporates the use of non-motorized grasping fixtures. The grasping fixtures 60i and 60j would grip the medical device in such a way that the medical device 10 could be held in place but be readily moveable when the medical device 10 is advanced by the bending tool 50m. Alternatively, the grasping fixtures could be opened and closed by the bending tool by means of a screw, clamp, gear, or any similar means. The grasping fixtures could be tightened to grasp the medical device by the bending tool 50m prior to bending, and then the fixtures could be loosened by the same means following bending to allow for advancement of the medical device. An additional embodiment could involve the adjustment of the grasping fixtures 60i and 60j such that the grasping fixtures hold the medical device 10 at a calculated pressure so that the medical device is held firmly but the robotic bender need only overcome the frictional force between the grasping fixtures or sterile barrier and the medical device in order to advance the device. Pressure or force sensors in the grasping fixtures 60i and 60j would keep the medical device 10 from being damaged during a gripping motion.

Alternatively, following heating the portion of the medical device 10 to be curved could be advanced all at once to allow the bending tool 50m to move along the length of the medical device and impart the curvature all at once instead of incrementally advancing the device after each bend. The medical device would be advanced past the heating unit 57 by any means discussed previously but in one segment instead of many small segments.

Because any medical device 10 to be bent in the above mentioned curving apparatus 4d is meant to be utilized in a surgical setting, the sterility of the medical device must be maintained. Sterile flexible bellows 125 are shown in the embodiment of FIGS. 51 through 55. These flexible bellows are composed of silicone, polyurethane, or any other elastomer, rubber, or textile that can be made sterile and have the ability to form to and move with the various elements of the curving apparatus 4d and act as a barrier between the sterile medical device and the bending tool 50m, which may or may not be completely sterile. Another option to maintain sterility would be a disposable or reusable cap of the same material discussed above that would cover the bending tool 50m. Further discussion of the sterile drape system can be seen in FIGS. 62 through 63.

An alternate used of the linear robotic mechanism would be to pull out the mandrel 30 after bending is completed. To accomplish this, the bending tool 50m would instead be a pinch and pull mechanism. The end of the medical device 10 would be pinched after being cooled while a separate part of the unit 50m would linearly pull the mandrel 30 to avoid causing deformation of the final curve. In order to create no deformation of the curve a mechanism could be utilized to press or pinch the entire cooled medical device 10 that was bent. Pulling the mandrel 30 out would then cause virtually no deformation.

Figure 54:
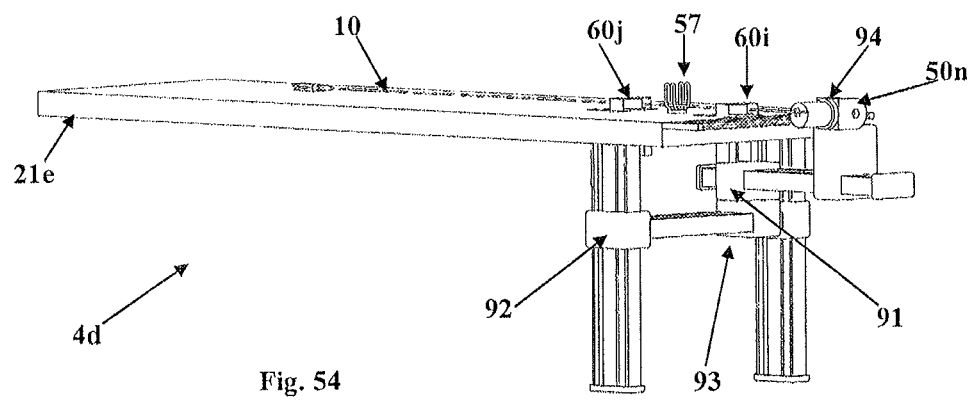
FIG. 54 is an illustration of the apparatus embodiment of FIG. 51 with vertical to horizontal hinged bending tool for 3D curving.
Figure 55:
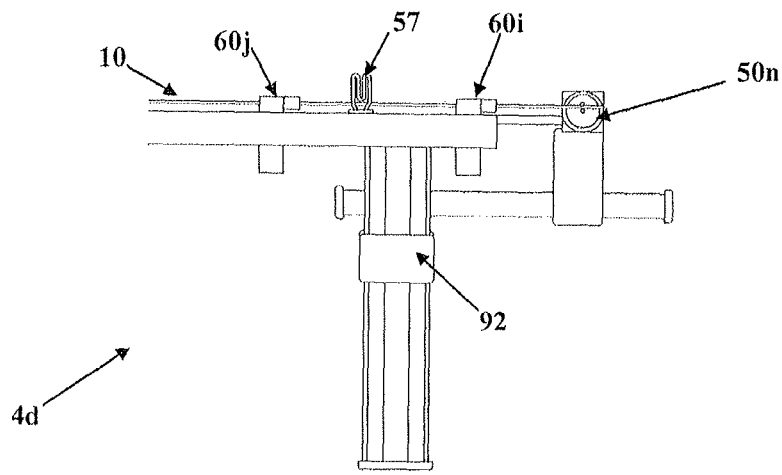
FIG. 55 is a section view illustration of the apparatus of FIG. 54.

FIGS. 54 and 55 detail an embodiment of the linear robotic curving apparatus 4d wherein the bending tool 50n has the ability to pivot, hinge, swivel, or by any means otherwise change its orientation from vertical to horizontal. The ability of the bending tool 50n to change its orientation allows the part to be bent in 2.5D or 3D because the theta axis motor's 94 rotation will cause the curvature to be imparted in an alternate plane from the bending tool's original orientation.

An alternative method of creating a 2.5D or 3D curvature with the curving apparatus 4d would require that the distal grasping fixture 60j be shaped similarly to the holder for the 3D bender 110 from FIG. 42. The grasping fixture would have the necessary radius for bending, and the bending tool 50n would move vertically and laterally by utilizing the x-, y-, and z-axis linear actuators 91, 92, and 93 to push the medical device 10 against the curvature of the grasping fixture to impart the curve. By incrementally advancing the medical device and utilizing both the linear robotic bending tool and the curved grasping fixture, any desired curvature may be imparted.

Figure 56:
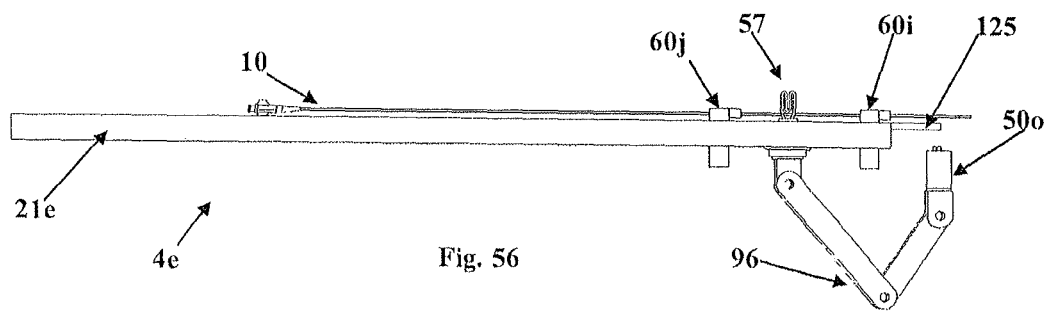
FIG. 56 is a side view illustration of a curving apparatus with a multi-axis robotic bending arm.
Figure 57:
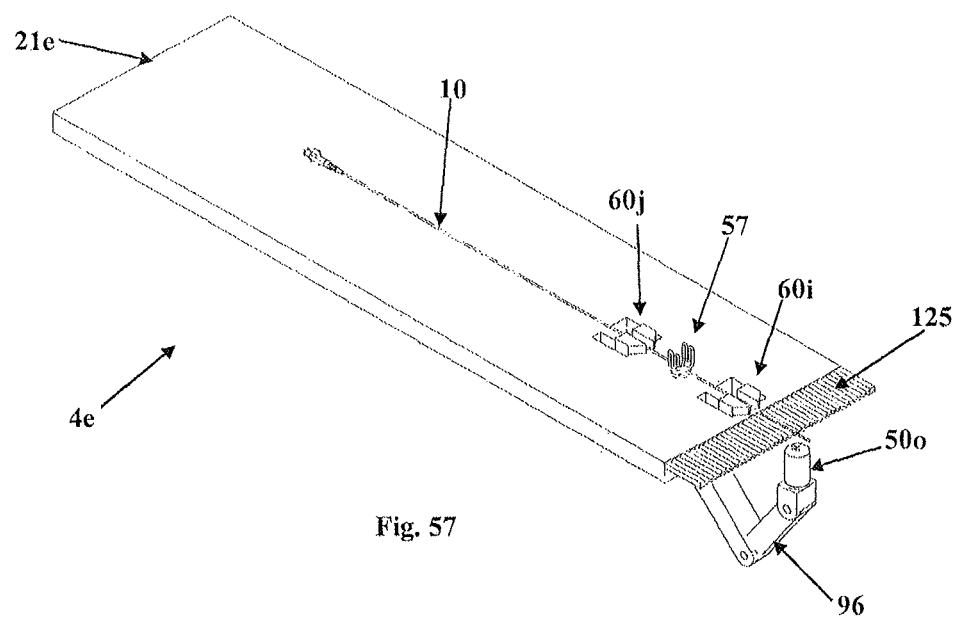
FIG. 57 is a pictorial view illustration of the embodiment of FIG. 56.
Figure 58:
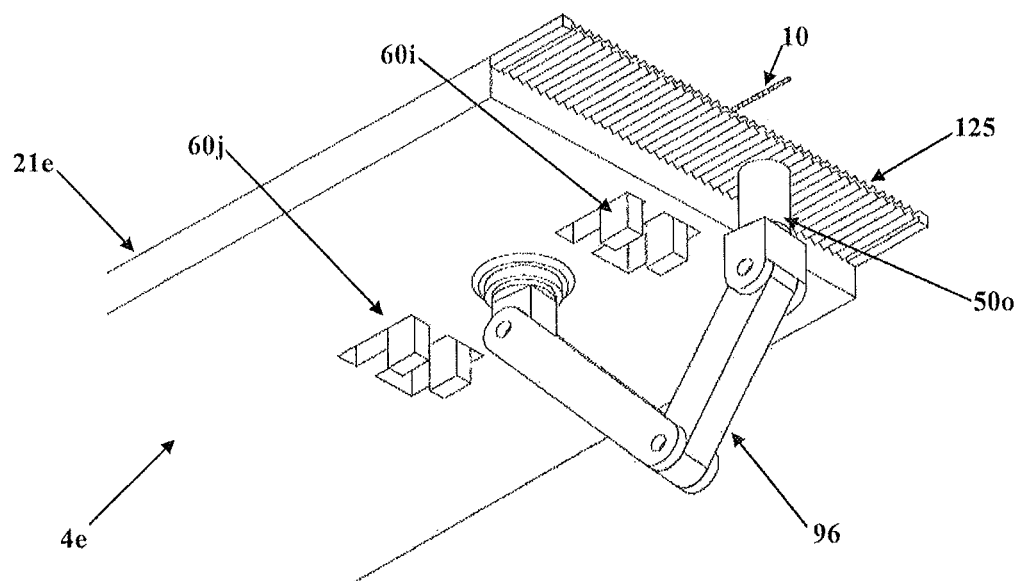
FIG. 58 is a section view illustration of the apparatus of FIG. 56.

FIGS. 56 through 58 detail an embodiment of the curving apparatus 4e wherein a multi-axis robotic bending arm used to impart the curvature. The multi-axis robotic arm curving apparatus 4e contains a primary base 21e, distal and optionally included proximal grasping fixtures 60i and 60j that may or may not have the ability to move, a heating unit 57, a multi-axis robotic arm 96, and a bending tool 50o which can be of any form as previously discussed in FIGS. 32 through 37. The multi-axis robotic arm may be comprised of anywhere between two and ten rotating joints to allow the arm to extend, reach, pivot, grasp, draw back, and in any other way move to perform any number of functions in association with the curving apparatus 4e. The bending tool 50o is attached to the distal end of the robotic arm to allow for a wide range of bending angles and positions. This range of available positions allows the bending tool to impart any desired curvature, whether in 2, 2.5, or 3D. To begin the bending procedure, the distal and proximal grasping fixtures 60i and 60j grip the medical device 10 and optionally included mandrel 30 to hold the device within the heating unit 57, which could alternatively be incorporated into the grasping fixtures. The grasping fixtures could advance the medical device by any means previously stated, or the medical device could be incrementally advanced by means of the bending tool 50o, which can rotate to grasp and advance the device the desired amount by virtue of the rotation of one or more of the axes of the robotic arm 96 When the medical device has been advanced past the grasping fixtures, the bending tool will move to a preprogrammed position and begin the bend by moving axially using the multi-axis robotic arm. The bending tool will move along the length of the medical device while performing the necessary rotations to form the curvature for the given incremental length, and then the medical device will be advanced again.

As previously stated for the linear robotic curving system in FIG. 54, the multi-axis robotic arm curving apparatus 4e will require a sterile drape. Silicone bellows 125 or an alternative sterile cap for the bending tool 50o will help maintain sterility in the bending environment. This cap can be flexible, static and any material previously discussed. Further discussion of sterile barriers follows in FIGS. 62 through 63.

Figure 59:
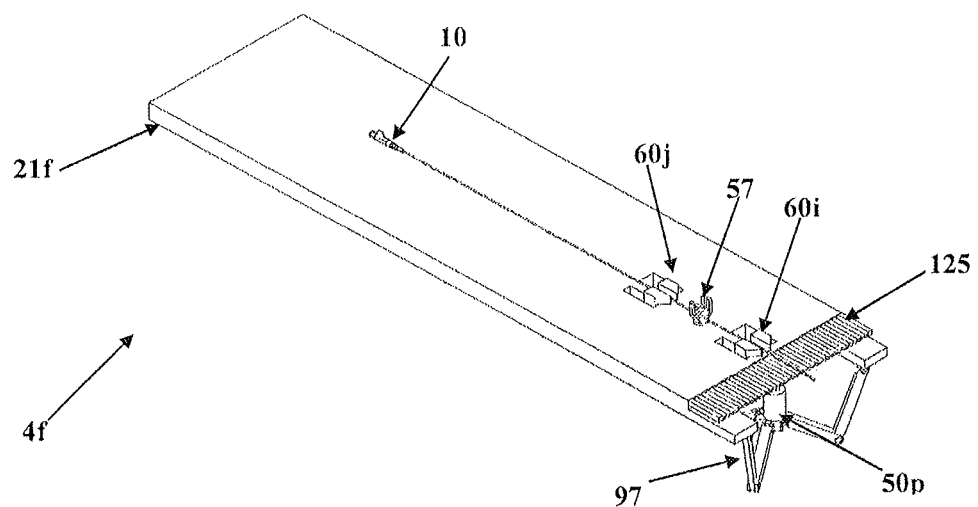
FIG. 59 is an isometric view of a curving apparatus embodiment including a tripedal robotic bending tool.
Figure 60:
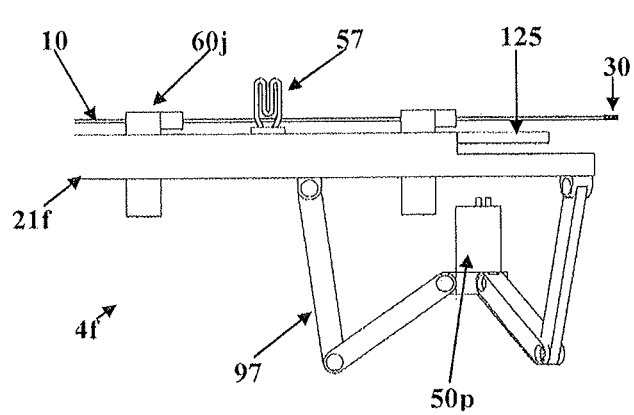
FIG. 60 is a section view illustration of the curving apparatus embodiment of FIG. 59.
Figure 61:
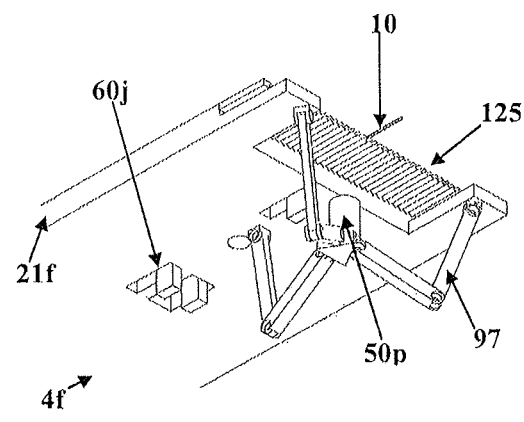
FIG. 61 is a pictorial section view of the curving apparatus embodiment of FIG. 59.

FIGS. 59 through 61 detail an embodiment of the curving apparatus 4f wherein a tripedal robotic bending tool is used to impart the curvature. The tripedal robotic curving apparatus 4f contains a primary base 21f, distal and optionally included proximal grasping fixtures 60i and 60j that may or may not have the ability to move, a heating unit 57, a tripedal robot 97, and a bending tool 50p which can be of any form as previously discussed in FIGS. 32 through 37. The tripedal robot 97 may be comprised of any number of rotating joints in each leg as needed to allow the unit to move laterally, raise, lower, rotate, or have motion in any way required to allow the bending tool 50p to impart the desired curvature in the medical device 10. The medical device will be advanced in the same way as previously discussed for the robotic devices in FIGS. 51 through 58, or in any other way similar to that described earlier. The curvature will be imparted on the medical device 10 in a similar manner to the previously described robotic devices with the exception that the bending tool 50p will rotate and move laterally and vertically by virtue of the motion produced by the various rotating joints of the tripedal robot 97 moving in conjunction with each other. As stated above for the linear and multi-axis robots, the tripedal robotic curving apparatus 4f will require a sterile drape or cover as described in FIGS. 62 through 63.

In order to maintain the sterility of the medical device 10 while it is being curved, the sterile medical device must be isolated from the non-sterile features of the curving apparatus including the bases, grasping fixtures, heating units, and forming units. FIG. 62 shows a sterile fenestrated drape 115 that will cover the entirety of the curving apparatus, such as the apparatus 4f shown in FIG. 59. The fenestrated drape 115 will be a sheet of any fiber, plastic, textile, or other material that can be made sterile and act as a barrier against infectious agents. The drape will cover the entirety of the curving apparatus including all features attached to the base as well as hanging down the sides of the base to the floor. The drape may have perforations, transparent areas, or markings that aid and instruct the user in the placement of the drape on the curving apparatus. Attached to the drape will be barriers of flexible materials that will fit over the protruding features such as the grasping fixtures, forming units and bending tool. Alternately the drape will have sterile covers than are used for any moving part. These covers can be attached to the fenestrated drape 115 or overlap to preserve sterility. The flexible barriers for the distal and proximal grasping fixtures and for the heating unit, 20c, 20d, and 20e, are shown in FIG. 62. The flexible barriers 20c through 20e are made out of a disposable or reusable rubber, silicone rubber, polyurethane, or any other material currently in use or will be used in the future that offers the combination of flexibility, heat conductivity, malleability, and/or any other characteristics necessary to allow the covered features to work as designed, maintain sterility, resist heat deformation caused by the heating unit or heated catheter, and elsewise allow for normal utilization of the curving apparatus. The flexible barriers will have the ability to align with their corresponding features and easily fit over said features when the fenestrated drape is put into place. The flexible barriers may also have corrugated bellows incorporated into the material to allow for easy, tensionless movement of the features of the curving apparatus.

An alternate way of keeping the medical device sterile through the process would be to keep the entire curving apparatus 4 (FIG. 1) always sterile. The apparatus would be housed in a sterile enclosure with two smaller enclosures located where the medical device 10 would enter the apparatus and where it would leave the apparatus. These two enclosures would be sealed off from the sterile main enclosure and only opened after the adjacent enclosure has been sterilized along with the medical device 10.

Another way to make sure the medical device 10 is sterile before use on the patient would be to sterilize the final bent medical device 10. This could be done using any previous or later mentioned way of sterilization. This would eliminate the need to sterilize any components of the curving apparatus.

Figure 62A:
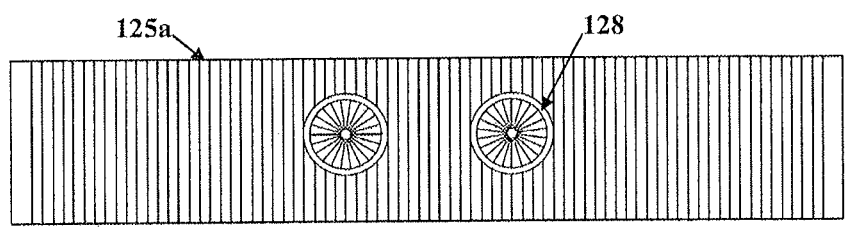
FIG. 62a is a segment of the sterile fenestrated drape of FIG. 62 including flexible bellows with formable segments.
Figure 62B:
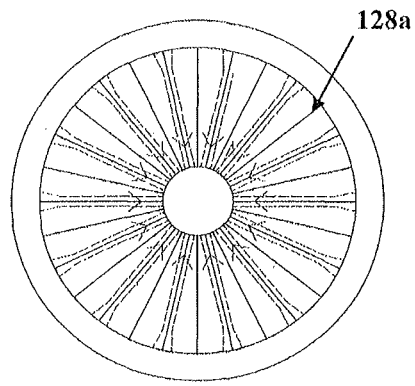
FIG. 62b is a top view of a radially corrugated segment of the fenestrated drape embodiment of FIG. 62.
Figure 62C:
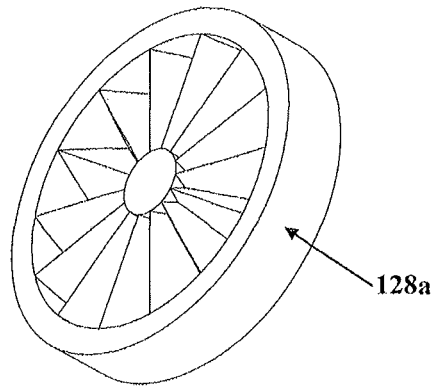
FIG. 62c is an isometric view of a radially corrugated segment of the fenestrated drape embodiment of FIG. 62.
Figure 62D:
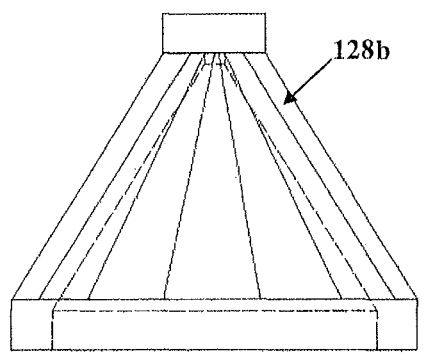
FIG. 62d is a side view illustration of a torroidal formable segment of the fenestrated drape embodiment of FIG. 62.
Figure 62E:
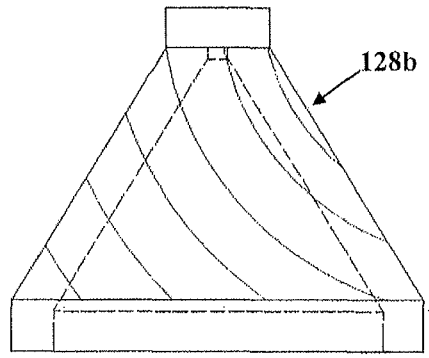
FIG. 62e is a side view illustration of a bent torroidal formable segment of the fenestrated drape embodiment of FIG. 62.
Figure 62F:
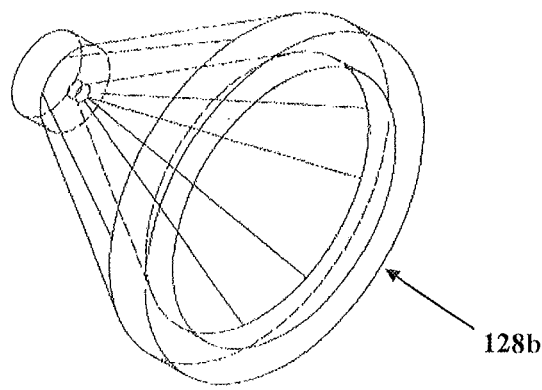
FIG. 62f is an isometric view illustration of the bottom of a torroidal formable segment of the fenestrated drape embodiment of FIG. 62.
Figure 62G:
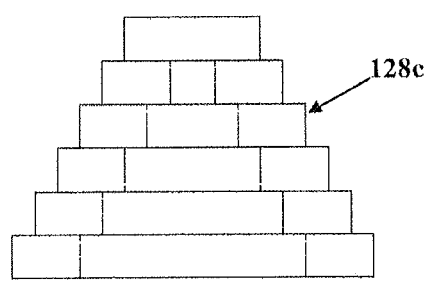
FIG. 62g is a side view illustration of a formable segment with circular corrugation that could be part of the fenestrated drape embodiment of FIG. 62.
Figure 62H:
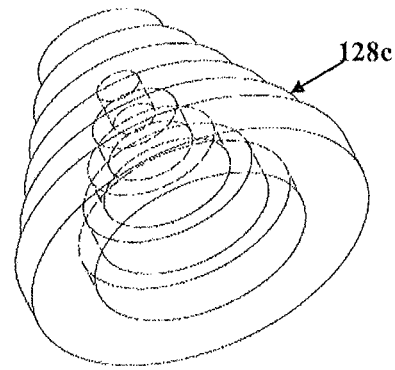
FIG. 62h is an isometric view illustration of the bottom of a formable segment with circular corrugation of FIG. 62h.

FIG. 62*a* details the flexible bellows section 125*a* that will be attached to the distal end of the fenestrated drape 115, immediately following the distal grasping fixture. The flexible bellows 125*a* will be made of the same disposable or reusable and elastomeric material as the flexible barriers 20*c* through 20*e*. The flexible bellows 125*a* will have a corrugation, fold, overlap, or in any other way hold more material than a simply smooth surface. The bending tool will have to impart the curvature upon the medical device through these flexible bellows, which will readily form to the features of the bending tool. The corrugation allows the barrier to form to and move with the bending tool while facing only significantly reduced tensile or compressive stresses.

While the flexible bellows readily move with the motion of the mechanisms on the curving apparatus, the formable segments 128 embedded into the flexible bellows 125*a* or fenestrated drape 115 are designed to fully conform to the head of the bending tool as the bending tool moves to engage with the medical device. The formable segments 128 of the barrier could also be molded specifically to fit the bending tool.

FIGS. 62*b* through 62*h* detail various embodiments of the sterile formable segments of the flexible barrier. The radially corrugated formable segment 128*a* has corrugation running from the center to the outer edge of the circular segment. The excess material allows the barrier to raise, twist, and unfold with the movement and rotation of the bending tool without placing any undue stress on the bending tool or the medical device. The toroidal formable segment 128*b* achieves a similar goal but has a flat, loose structure that easily twists with the bending tool. Alternatively, the formable segment with circular corrugation 128*c* allows for easy change of height of the bending tool while easily twisting around the body of the bending tool.

In the case of the barrier having flexible bellows, the bellows may be a different material than that of the barrier that embodies the portions of the curving apparatus that are stationary. The barrier over the stationary portions may be a standard surgical drape material, where the bellows may be a fabric, polymer, composite, elastomer or rubber material. If the bellows are in contact with a heated forming unit, they must be of a heat resistant such as silicone, or teflon. If there is no heating, or if the heating is created on the inside of the medical device, the material need not be heat resistant, and might consist of polyurethane, polyolefin, polyester, nylon, fiberglass, nitrile, or any combination thereof.

Figure 63:
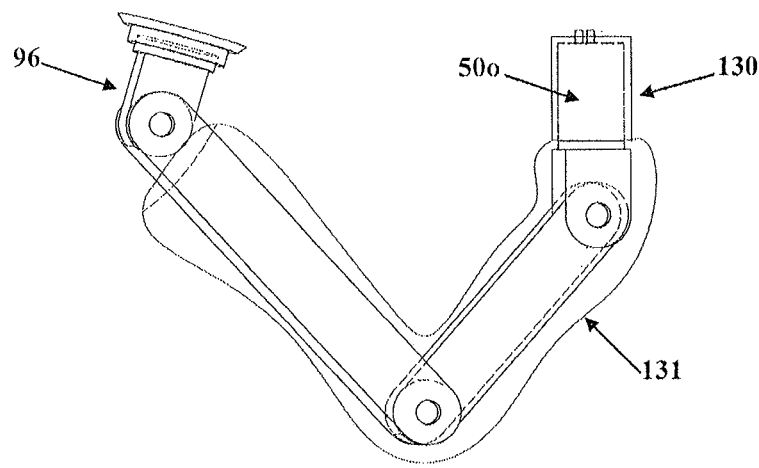
FIG. 63 is an illustration of an embodiment of a sterile covering for a robotic device.

FIG. 63 details an embodiment of the multi-axis robotic arm 96 and its associated bending tool 50*o* covered by a sterile cap 130 and a sterile cover 131. Any feature or mechanism not isolated from the sterile medical device by the sterile drape or barriers must be covered by individual barriers in order to maintain sterility of the medical device. The sterile cap 130 can be molded to the shape of the given bending tool 50*o*, or it can stretch or otherwise form to the shape of the bending tool upon contact. The sterile cover 131 will be any fiber, plastic, textile, or other material that can be made sterile and act as a barrier against infectious agents and will connect to the ends of the sterile cap 130 and completely cover the robotic arm or other mechanisms that connect to and control the bending tool.

If a completely sterile environment is not maintained throughout the curving procedure, a final sterilization step must be included. Any known method of sterilization may be utilized on the medical device 10 (FIG. 8), such as moist or dry heating, chemical sterilization, gas sterilization, or ultraviolet or other radiation sterilization. This ensures that the medical device 10 is free of living microorganisms for the planned surgical procedure.

Figure 64:
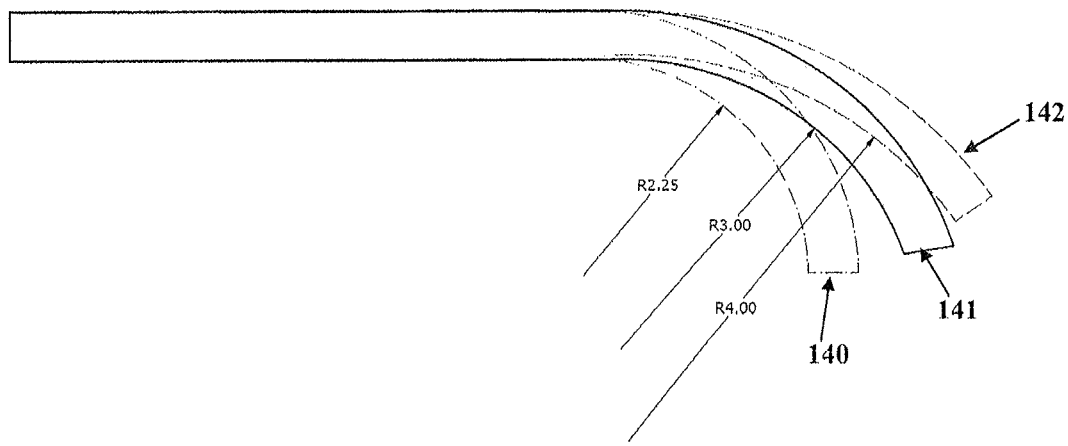
FIG. 64 is a diagram representing the desired curvature versus overbending and underbending.

A source of possible error in the curving system is hysteresis in the imparted curvature. It is possible that the medical device could lose a small percentage of the bend due to elasticity or a simple imprecision in the curving motion. Due to the elasticity inherent in the materials used for these medical devices, especially the plastics, the device will display some inclination to return to its original shape by some degree. It will be required that the medical device be bent by some calculated amount greater than called for by the intended curvature, a method called "overbending," in order to produce the precise radii of curvature. The amount of overbending required for each medical device will be a function of the device's material, its inner and outer diameters, the amount of heat and whether it is being heated from the inside, outside, or both, and the radius of the intended curvature. FIG. 64 illustrates the shape of the desired curvature 141 versus the overbent position 140 and the underbent position 142. In order to impart the precise curvature upon the medical device, the device is bent into the overbent position 140. When the medical device is released, the mechanical properties of the material cause it to rebound towards its original shape, thereby settling with a larger radius of curvature that is the desired size 141. If the medical device is not overbent to the specifications of the material, or if the curving apparatus is programmed to simply bend the device at the desired curving radius, the mechanical properties will cause the radius of curvature to increase past the desired curvature 141, resulting in an underbent curvature 142. The curving apparatus 4 could have many different ways of calculating the overbend for a material. One way is using some type of visual software or artificial intelligence that will quickly test the materials overbend before bending the medical device 10. The curving apparatus 4 could have stored equations, and algorithms for each material and material factor in the curve database 2 (FIG. 1). These equations could be preprogramed into the database or be user inputted.

Figure 65:
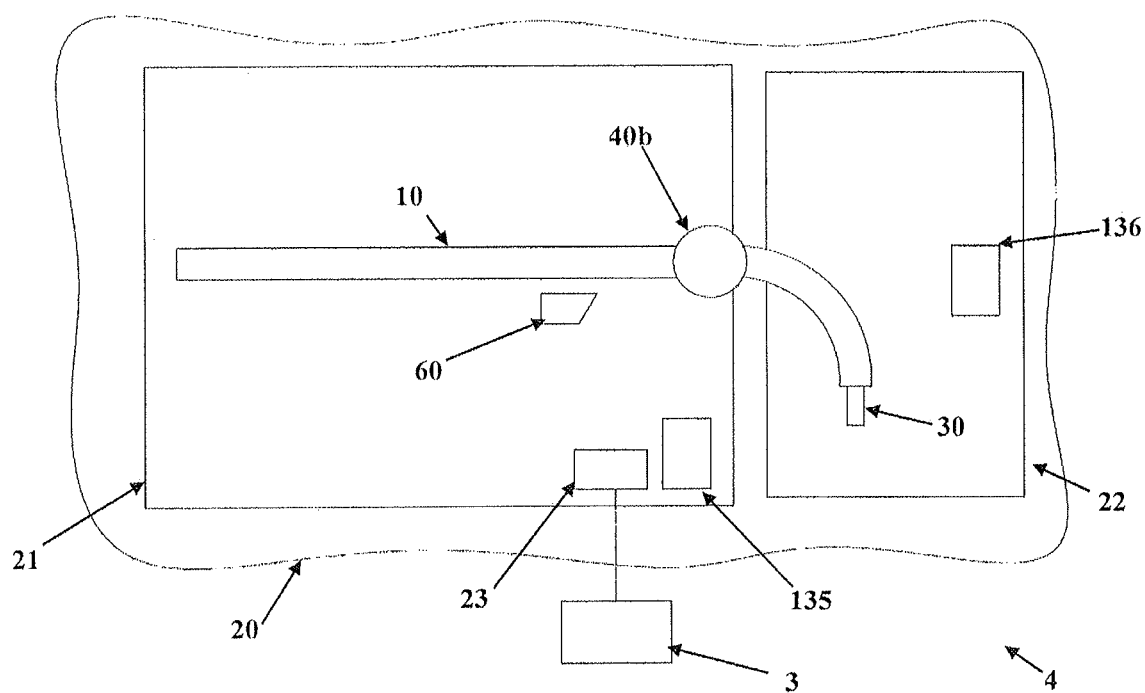
FIG. 65 is a diagram representing the inclusion of a feedback system in the curving apparatus.

FIG. 65 is a pictorial plan view of a curving apparatus 4 embodiment with a medical device 10, a support mandrel 30 extending longitudinally inside the lumen of the medical device 10, a grasping fixture 60, a primary base 21, a secondary base 22, a barrier 20, a controller 23, and a bending tool 40*b*. The curve user interface 3 can be connected to the controller 23 as part of the medical device curving system 1 (not shown) as previously discussed. To counteract the error that may occur in the bending procedure, a feedback control system 135 will be included and will be composed of a variety of feedback sensors 136 and measurement devices along with a regulation system and a connection to the curve database. While the bending tool 40b is imparting the curve on the medical device, the series of sensors will compare the shape of the desired curvature with that of the newly bent medical device. These sensors 136 could be any combination of heat, motion, laser, light, vision, optical, force, pressure, inductive, capacitance, ultrasonic, or any other sensor or measurement device that can accurately determine the size and shape of the imparted curve. The data gathered from the feedback sensors will be used to determine if the bend must be changed, and the feedback control system 135 will be able to alter the bending program to rebend or otherwise alter the bend so that the curvature is precise.

Figure 66:
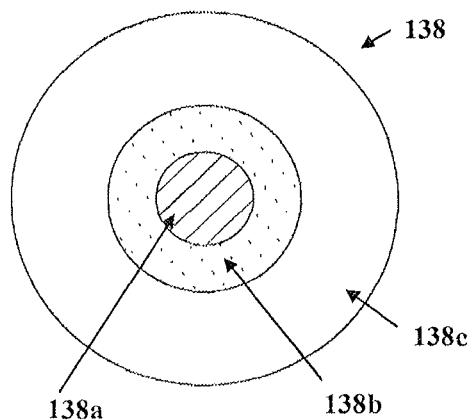
FIG. 66 is a cross section view of an embodiment of a composite mandrel to be used in association with the feedback system.

To aide in the precision measurement of the imparted curvature, a specialized mandrel may be used to determine the position of the medical device prior to and following bending. FIG. 66 depicts a specialized composite mandrel 138 to be utilized with the feedback system including a material that will aide in the position detection of the medical device 138c, a material that will aide in heating 138b, and a malleable core 138a to hold the curve position during cooling. The inner material, 138c, will be composed of any material, such as a ferromagnetic material, that can in some way be detected by the feedback sensor system. Placing a current through the ferromagnetic material 138a will create a magnetic field around the mandrel in the same way as a bar magnet would. The magnetic field weakens as the distance from the ferromagnetic material Sensors about 138a increases which will be recorded by the sensors. The curving apparatus 4 (FIG. 1) will be able to measure the force of the magnetic field at numerous points and use software that can calculate the field strength and shape to render the exact shape of the mandrel 138 which will be the same shape as the medical device 10. This will allow the system to know the precise shape and position of each bend and allow the user or the machine to determine if the curvature is within design specifications. The heating material 138b will be composed of any material mentioned earlier that will aid in the heating and bending of the medical device. The inner material 138a will have the task of holding the shape of the medical device to be bent. A composite mandrel has the benefit of each of the materials making up the composite. Elements such as iron, aluminum, titanium, copper, nickel, tin, barium, bismuth, chromium, manganese, and cobalt all offer unique properties with induction heating and malleability of the mandrel 138. All composite layers must bend with the device while not losing its given shape or expanding or shrinking in any way that affects the lumen. Two types of hysteresis must be looked for in association with the mandrel. First, the feedback system will determine if hysteresis has occurred just following the bending procedure. This will be determined while the mandrel is still in place. Secondly, hysteresis or unwanted bending could occur during the removal of the mandrel from the medical device 10. For this reason, methods for carefully removing the mandrel have been devised to limit the amount of unwanted bending during removal such as the mandrel itself being made to slide more readily from the lumen by any means such as lubricous coatings, softening or dissolution.

Figure 67:
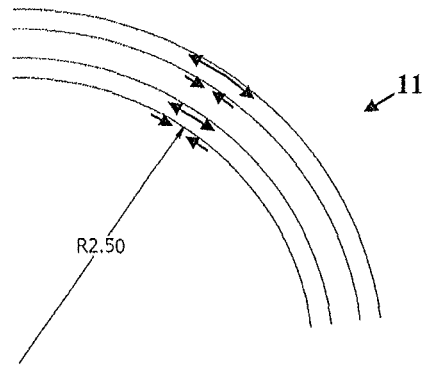
FIG. 67 is a pictorial view of a bent hollow medical device showing the areas of tension and compression in the curve.

Because the medical device is being plastically deformed, it will obviously be exposed to stresses and strains. FIG. 67 depicts a curved hollow medical device 11 with markings to indicate the tensile and compressive forces present on each wall of the device. The arrows point inward to represent compression at the outer diameter of the inner curve and the inner diameter of the outer curve. The tensile stresses, where the material will be stretched, occur where the arrows point away from each other, at the inner diameter of the inner curve and at the outer diameter of the outer curve.

Figure 68:
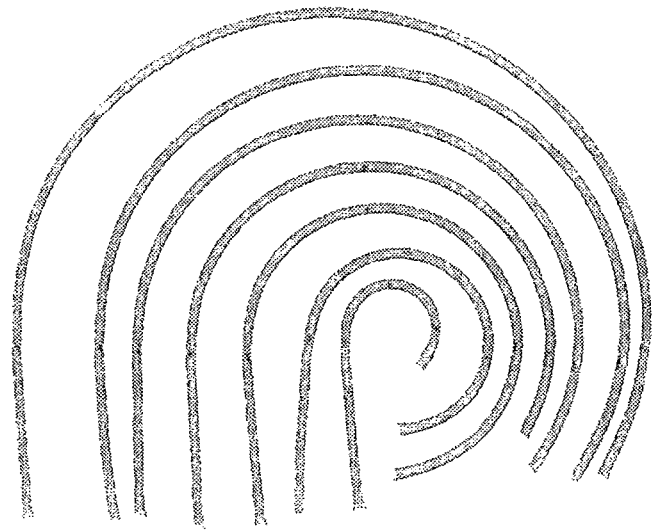
FIG. 68 is a pictorial view of catheters that have been placed in a mold and heated to form the desired curvatures.

To more readily understand the changes that occur during the bending process, an experiment was performed. FIG. 68 depicts a resulting sample of an experiment wherein a 5 French catheter was placed in molds of successively sized radii of 0.25, 0.5, 0.75, 1.0, 1.25, 1.5, and 1.75 inches, heated to a specified temperature, and cooled. It was immediately clear from visual observations that the catheters heated to lower temperatures had a tendency to return more fully toward their original straight orientation, while catheters heated closer to their melting points remained more tightly fitted to their intended curvature.

Figure 69:
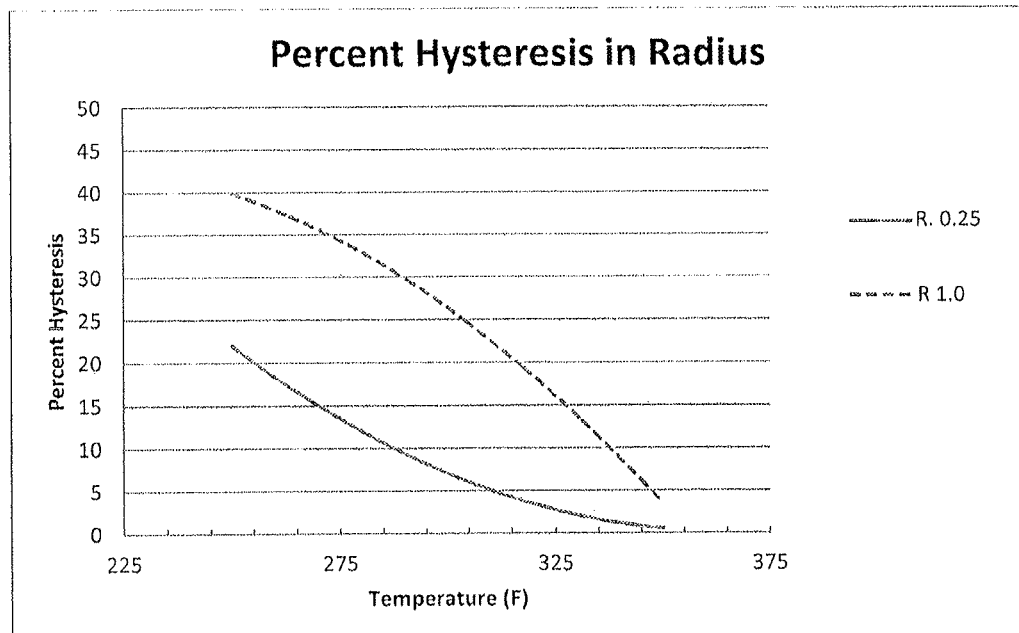
FIG. 69 is a chart illustrating the hysteresis in bend radius at various heating temperatures.

FIG. 69 is a chart depicting the percent hysteresis in radius in the 0.25 inch radius (solid line), and 1.0 inch radius (dotted line) curves at different temperatures. Clearly, the hysteresis, or the catheter's tendency to bounce back toward its original alignment, decreases at higher temperatures. At lower temperatures, around 250° F., the catheters display huge differentiations from the desired radii, while at 350° F., both of the radii show a hysteresis of less than five percent. Clearly, the closer the material is to its melting point, the more likely it is to have a one-to-one relationship between the desired radius and the resulting one.

Figure 70:
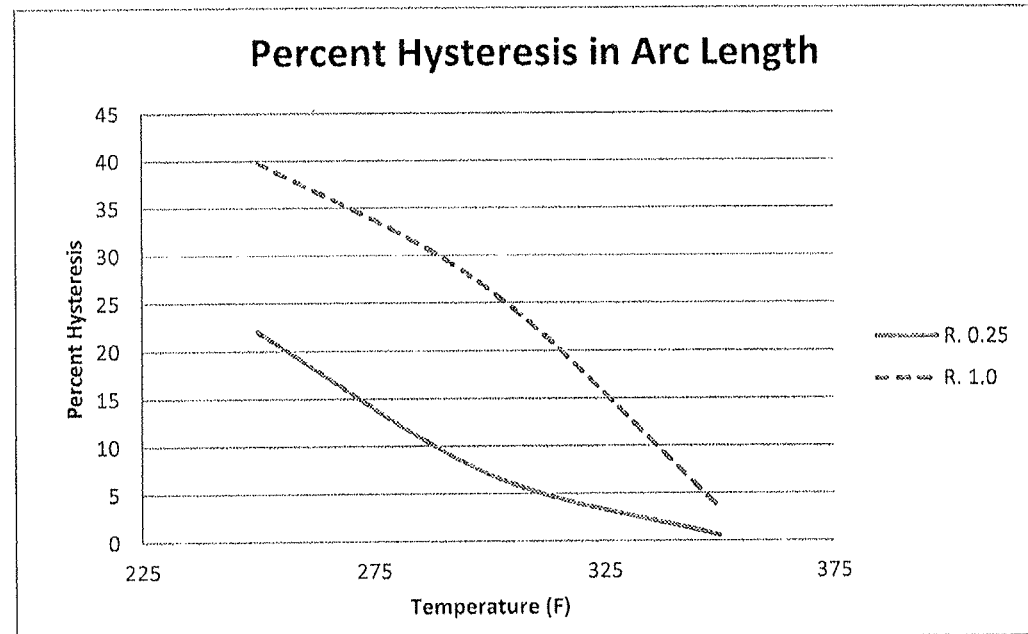
FIG. 70 is a chart illustrating the hysteresis in arc length at various heating temperatures.

FIG. 70 is a chart depicting the percent hysteresis in arc length of the 0.25 inch radius (solid line), and 1.0 inch radius (dotted line) curves at different temperatures Similar to the chart for the hysteresis of the radii, the hysteresis of the arc length significantly decreased with increasing temperature. At lower temperatures, the slight hysteresis in all points combined to make large percent changes in arc length. As the temperature increased towards the material's melting point, however, the percent change decreased significantly. Clearly, higher temperatures produce more precise samples with the mold plate and convection oven technique.

Figures 71, 72, 73:
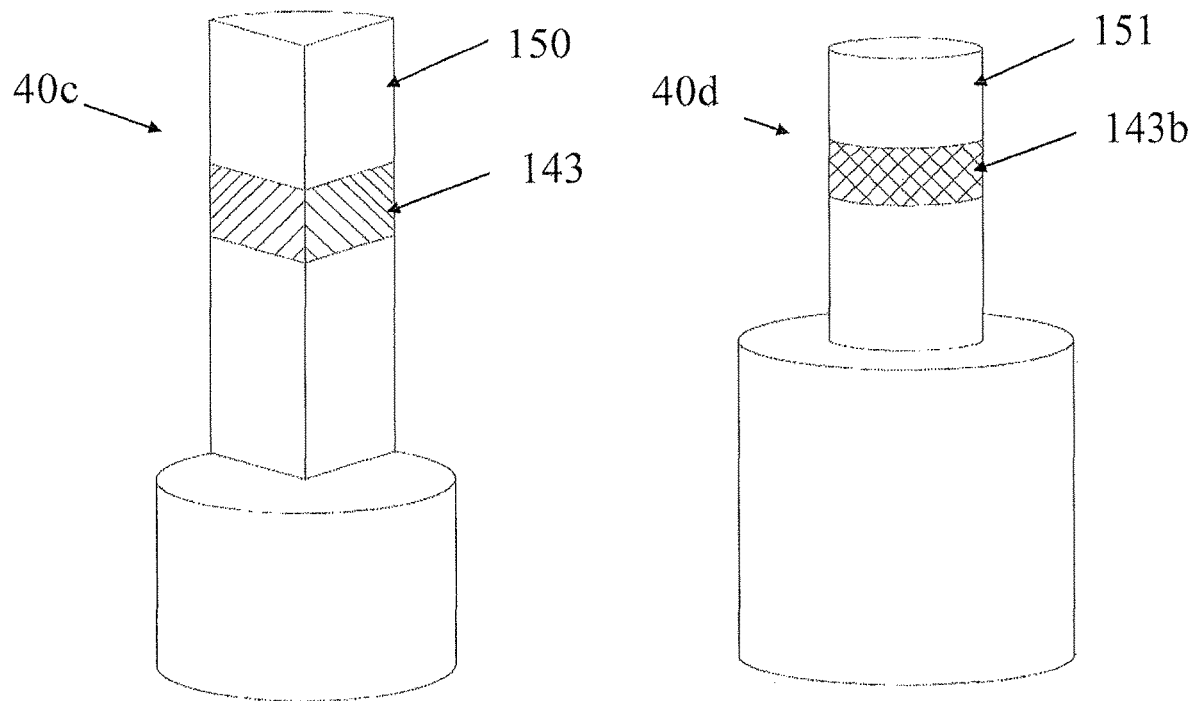
FIG. 71 is a chart listing the various Curie Point temperatures for a range of materials.
FIG. 72 is a pictorial view of an embodiment of a bending tool with proximity sensor.
FIG. 73 is a pictorial view of an embodiment of a bending tool with proximity sensor.

FIG. 71 is a table depicting the Curie Point temperature of a variety of materials. Curie temperature, or Curie point, is the temperature where a material's permanent magnetism changes to induced magnetism. The Curie point is important during induction heating, as induction heating is most effective below the Curie temperature where materials lose their magnetic properties. It is obvious from the limited materials shown that a very wide range of Curie Point temperatures can be achieved. It can also be shown that different alloys, with varying amounts of each element, can produce wildly varied temperatures. In this way, it is possible to hone in on an effective temperature to impart the ideal permanent curve. A mandrel, for example, filled with a combination of Cobalt Oxide and Nickel Oxide can be tuned to a Curie point of 315 degrees F., thereby when heated by induction, could heat the medical device to this temperature.

The curving system may also contain some type of artificial intelligence so that it can utilize the input and experimentally determined data for specific medical devices to calculate the ideal bending conditions or mandrel specification for each device. The database may have input from the user network or be able to calculate any of the necessary mechanical properties of the materials, outer diameter and thickness of the materials, most efficient bending temperature, the degree of overbending needed, etc. Prior to bending, the system will have the ability to determine if a support mandrel is necessary. The system will further be able to save any new knowledge such as preferred heating temperatures, and/or heating time, and degrees of overbending for each device to the network. The system can also compare the new data to the preexisting database to determine the best possible method of curvature. The system will therefore learn from and correct its own errors by altering the programmed heating, incremental movement, and bending procedures. Once the curving procedure is satisfactory, the methods and data can be added to the user network so that any user can benefit from the additional information.

FIG. 72 shows a bending tool 40c with a surface 150 utilizing proximity sensors 143 to track the location of the medical device 10 (not shown). Tracking the medical device 10 between incremental bends will allow the curving apparatus 4 (FIG. 1) to determine whether or not the proper radius bend has been imparted on the medical device 10. The proximity sensors 143 on the bending tool 40b can use many different types of sensors. For example, ultrasonic, radar, laser, force, pressure, magnetic, inductive, and capacitance sensors, or cameras using visual software or any other sensor to determine the precise location of the medical device 10 can be utilized by the bending tool 40c.

It is also contemplated that sensors can be incorporated into other portions of the curving apparatus (not shown), e.g., the grasping fixture (not shown), so as to determine the position or force that the grasping fixtures will converge on the medical device 10; or the forming unit (not shown) so as to establish the curving force or position of the curve throughout the curving process.

FIG. 73 shows the same type of proximity sensor 143b on a cylindrical bending tool 40d with surface 151. The bending tool 40d instead uses a cylindrically shaped proximity sensor 143b. Unlike the previous bending tool 40c a cylindrical shape allows the curving apparatus 4 (FIG. 1) to calculate the position of the medical device 10 (not shown) in any direction.

Figure 74:
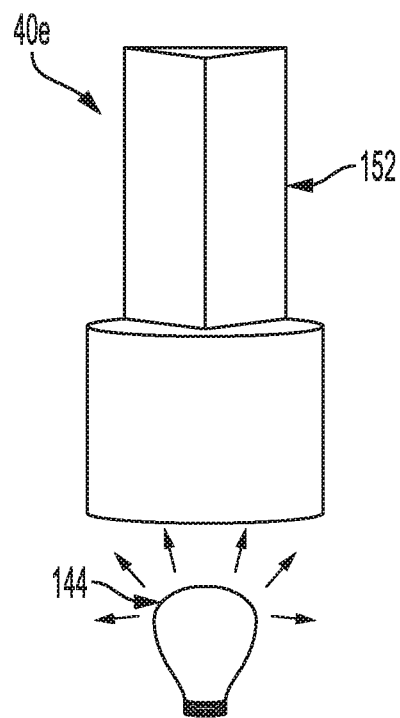
FIG. 74 is a pictorial view of an embodiment of a bending tool with electromagnetic sterilization.

The barrier to maintain sterility of the medical device 10 (FIG. 8) can be active or passive. A passive barrier can be a physical barrier between a non-sterile portion of the apparatus 4 (FIG. 8) and the sterile medical device 10 (FIG. 8). An active barrier makes a non-sterile portion of the apparatus 4 (FIG. 8) sterile by a means of sterilization. FIG. 74 details a bending tool 40e with surface 152 that is maintained sterile by electromagnetic radiation, for example ultraviolet radiation (UVC). UVC can be used for sterilization within the curving apparatus 4 (FIG. 8). UVC light can be creating using a mercury-vapor lamp or a Light Emitting Diode (LED) configured to emit UVC waves at 254 nm, the wavelength which kills microorganisms. There are numerous ways the light can be utilized in the sterilization process. The sterilization source 144 as a UVC source could be housed below the bending tool 40e, or any other part of the curving apparatus 4 (FIG. 8) that comes in contact with the medical device 10 (FIG. 8). For the UVC light to sterilize the outside of the part the body must be transparent to the specific wavelength the UVC light sterilizes at. For example, quartz is a material that is transparent to UVC which will allow the outside layer to be sterilized by UVC light. A textured or etched surface may be used to refract the UVC at the surface 152 to ensure that the surface emits the UVC light.

Figure 75:
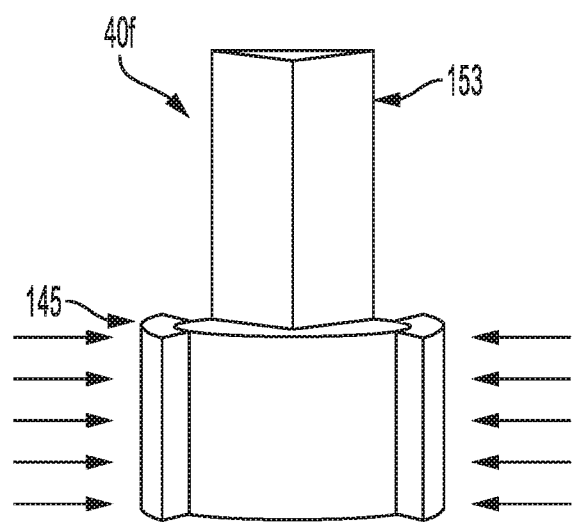
FIG. 75 is a pictorial view of an embodiment of a bending tool with heat sterilization.

FIG. 75 details a separate way of sterilizing a bending unit 40f with surface 153. A heat source 145 is used to transfer heat to the surface 153 by means of conduction, convection, or radiation. The temperature can be varied to reach any heat to kill any type of microorganism on the surface 153.

Figure 76:
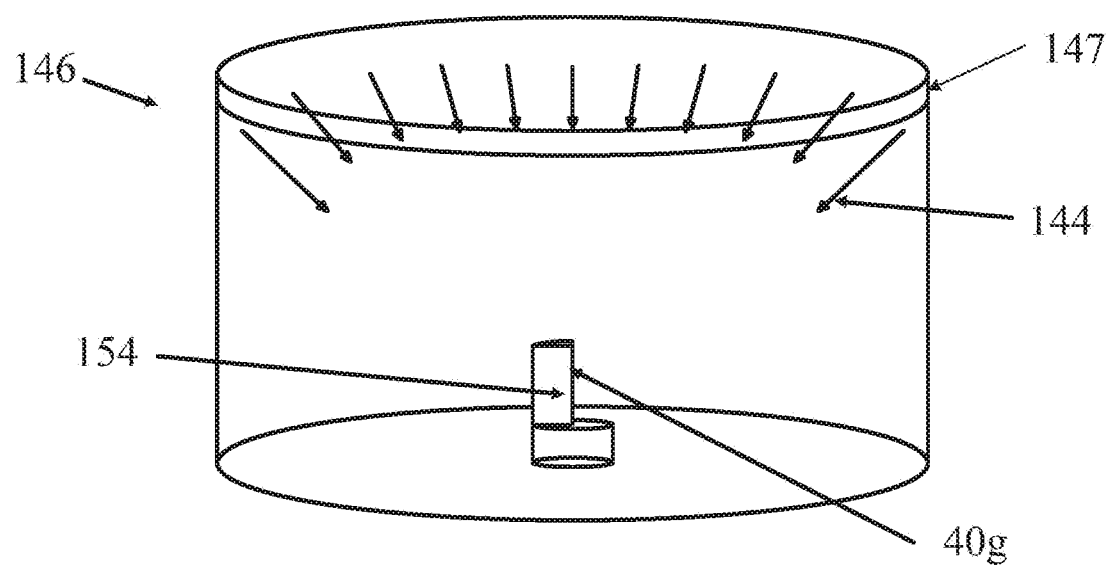
FIG. 76 is a pictorial view of an embodiment of a bending tool with electromagnetic sterilization.

FIG. 76 illustrates a light protective system 146 which includes a guard 147 to block out the UVC rays 144 from coming in contact with the user and a bending tool 40g with surface 154. UVC is used to kill microorganisms on the surface 154 of the bending tool 40g, so a guard 147 may be utilized to protect the user from the electromagnetic radiation. The guard 147 may encompass the entire curving apparatus 4 (FIG. 8) or just the specific parts with UVC light sources 144 (FIG. 74) beneath them. The guard 147 may be made out of a material that is opaque to the UVC wavelength. For example, a glass guard would block enough UVC light to make it safe for the user, as glass absorbs 90% of UVC.

Utilizing a guard 147, also enables the bending tool 40g to be sterilized with electromagnetic radiation, or a UVC light sterile source 144 from above. The sterile source 144 can be located under the guard 147 and project a blanket of UVC over the portions of the curving apparatus (not shown) that could come in contact with the medical device (not shown). The sterile source 144 could cycle on during startup and ensure that the curving apparatus (not shown) is sterile before use. This would enable the sterile source 144 to be off during use and the guard 147 moved out of the way or removed so as not to obstruct the curving process.

It is also contemplated that the sterile source 144 be another means of sterilizing the curving apparatus, such as plasma, gas, liquid, or other forms of EMR. For example sterile source 144 could be ozone or hydrogen peroxide gas which are both used to sterilize within an enclosure. In this case, the guard 147 would act as a temporary enclosure for the curving apparatus (not shown) for the duration of the sterilization process and be removed or moved out of the way once complete so that the curving apparatus (not shown) can be used and sterility maintained on the medical device (not shown). Any known means of sterilizing the surface of the curving apparatus could be used in this manner, and would allow the curving apparatus to maintain sterility of the medical device without a barrier.

Figure 77:
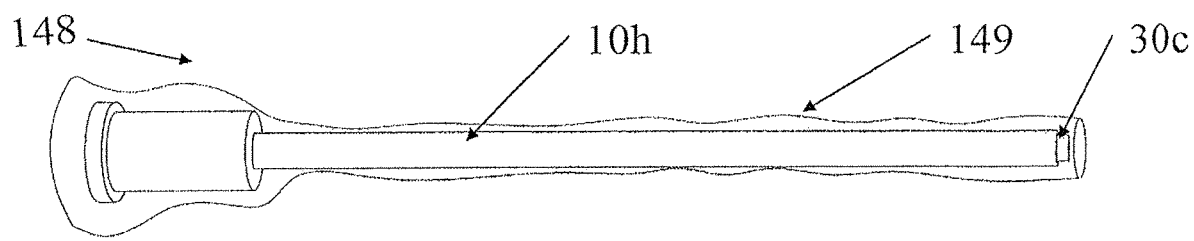
FIG. 77 is a pictorial view of an embodiment of a medical device with a barrier.

FIG. 77 shows another means of maintaining sterility of a medical device 10h by way of a sterile sleeve embodiment 148. A barrier 149 fully or partially envelops the medical device 10h in the areas that come in contact with non-sterile portions of the curving apparatus (not shown). The barrier 149 could also cover the mandrel 30c, or the mandrel 30c could project outside of the barrier 149. The barrier 149 could be a loose fitting material, or could tightly contour the medical device 10h, so long as it does not impede the operation of the curving apparatus. The barrier 149 can be made from any type of flexible polymer or any other material that will not affect the curving process but be sturdy enough to withstand the bending process, both mechanically and physically, e.g., it must withstand any heating, sterilization, bending forces, grasping, etc. It is further contemplated that the barrier 149 contain sensors or materials that work with other sensors within the curving apparatus (not shown) to assist with the feedback system. This can be in conjunction with, or separate to sensors on the grasping fixture, forming units, bending tool and mandrel 30c.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A system for curving a sterile elongated medical device, the system comprising:
   (i) a curving apparatus, (ii) a sterile barrier that is configured to at least partially cover the curving apparatus and is removably positionable at a location directly between the curving apparatus and the sterile elongated medical device, (iii) and a curve database corresponding to at least one curve shape;
   the curving apparatus configured to impart a permanent curve according to the curve shape on a distal portion of the sterile elongated medical device that is greater than that on a proximal portion of the sterile elongated medical device, wherein the sterile barrier prevents the curving apparatus from directly contacting the sterile elongated medical device while the curving apparatus imparts the permanent curve to the sterile elongated medical device in order to maintain sterility of the sterile elongated medical device.

2. The system of claim 1, wherein the sterile barrier is a molded cap, cover, sleeve, bellows or drape.

3. The system of claim 1 further comprising a communication device configured to connect with an imaging unit providing information specific to a patient anatomy to the system.

4. The system of claim 3 further configured for curving the elongated medical device based on data from the imaging unit.

5. The database of claim 1 further comprising information for each curve including an image of the curve, a curve identifier, and characteristics specific to the elongated medical device.

6. The system of claim 1, the curving apparatus comprising a sensor, and the system being configured for curving the elongated medical device based on feedback from the sensor of the curving apparatus.

7. The system of claim 1 further configured to heat the elongated medical device in order to maintain the permanent curve.

8. The system of claim 1 further comprising a user interface configured for selecting information stored in the curve database by a user.

9. The system of claim 8, the user interface being configured for selecting information through hand, voice, or foot gestures.

10. The system of claim 8, the user interface being configured with a sterile cover to be operated by a user wearing sterile attire.

11. The system of claim 8, the user interface being configured to be remotely operated by a user.

12. The system of claim 1, the curve database being remote from the curving apparatus.

13. The system of claim 12, the curve database being cloud based.

14. The system of claim 1 further comprising a user network configured for updating the curve database.

15. The system of claim 1, wherein the curve database further comprises curve overbend information corresponding to the curve.

16. The system of claim 1, wherein the curve database further comprises pathology information corresponding to the curve.

17. The system of claim 1, wherein the curve database further comprises anatomy information corresponding to the curve.

18. The system of claim 1, wherein the curve database further comprises procedure information corresponding to the curve.

19. The system of claim 1, wherein the curve database further comprises patient characteristics corresponding to the curve.

20. The system of claim 1 further configured to curve the elongated medical device with a 3-dimensional curve.

21. The system of claim 1, the elongated medical device comprising an intravascular catheter.

22. The system of claim 21, the intravascular catheter being selected from a group consisting of a guiding catheter, a diagnostic catheter, and a microcatheter.

23. A system for curving a sterile elongated medical device, the system comprising:
   a curve database storing information corresponding to one or more curvatures that can be applied to the sterile elongated medical device;
   a user interface configured for selecting characteristics specific to the sterile elongated medical device stored in the curve database;
   a curving apparatus configured for curving the sterile elongated medical device based on information stored in the curve database and selected by a user; and
   a sterile barrier that is configured to at least partially cover the curving apparatus and is removably positionable at a location directly between the curving apparatus and the sterile elongated medical device to prevent the curving apparatus from directly contacting the sterile elongated medical device while the curving apparatus imparts a curve to the sterile elongated medical device in order to maintain sterility of the sterile elongated medical device.

24. The system of claim 23 further comprising a heat source.

25. The system of claim 23 further comprising a mandrel to support the elongated medical device.

26. The system of claim 23, wherein the curving apparatus is configured for curving multiple elongated medical devices at one time.

27. The system of claim 23 further comprising a user network configured for updating the curve database.

28. The system of claim 27, wherein the network is cloud based.

29. The system of claim 23, wherein the curving apparatus is further configured to overbend the elongated medical device in order for the curve on the elongated medical device to approximate the curve in the curve database.

30. The system of claim 23, wherein the sterile barrier is a molded cap, cover, sleeve, bellows or drape.

31. The system of claim 23, further comprising a robot or automatic insertion system for the elongated medical device.

32. A system for curving a sterile elongated medical device, the system comprising:
    a curve database that is configured to store information corresponding to at least one curvature that can be applied to the elongated medical device;
    a curving apparatus comprising a heater configured to impart a permanent curve according to the at least one curvature on a distal portion of the elongated medical device that is greater than that on a proximal portion; and
    a sterile barrier that is configured to at least partially cover the curving apparatus and is removably positionable at a location directly between the curving apparatus and the sterile elongated medical device to prevent the curving apparatus from directly contacting the sterile elongated medical device while the curving apparatus imparts a curve to the sterile elongated medical device in order to maintain sterility of the sterile elongated medical device.

33. The system of claim 32 further comprising a mandrel.

34. The system of claim 32, wherein the curving apparatus is configured for curving multiple elongated medical devices at one time.

35. The system of claim 32 further comprising information for each curve including an image of the curve, a curve identifier, and characteristics specific to the elongated medical device.

36. The system of claim 32 further comprising a user network configured for updating the curve database.

37. The system of claim 36, wherein the user network is cloud based.

38. The system of claim 32, wherein the curving apparatus is further configured to overbend the elongated medical device in order for the curve on the elongated medical device to approximate the curve in the curve database.

39. The system of claim 32, further comprising a robot or automatic insertion system for the elongated medical device.

40. The system of claim 32, wherein the sterile barrier is a molded cap, cover, sleeve, bellows or drape.

* * * * *